(12) United States Patent
Ando

(10) Patent No.: US 10,591,285 B2
(45) Date of Patent: Mar. 17, 2020

(54) IMAGE INSPECTION APPARATUS

(71) Applicant: Keyence Corporation, Osaka (JP)

(72) Inventor: Daisuke Ando, Osaka (JP)

(73) Assignee: Keyence Corporation, Osaka (JP)

( * ) Notice: Subject to any disclaimer, the term of this patent is extended or adjusted under 35 U.S.C. 154(b) by 72 days.

(21) Appl. No.: 15/955,732

(22) Filed: Apr. 18, 2018

(65) Prior Publication Data

US 2018/0348146 A1    Dec. 6, 2018

(30) Foreign Application Priority Data

May 31, 2017    (JP) ................................ 2017-107354

(51) Int. Cl.
| | |
|---|---|
| *G01B 11/25* | (2006.01) |
| *G01N 21/88* | (2006.01) |
| *G01N 21/55* | (2014.01) |
| *G06T 7/00* | (2017.01) |

(52) U.S. Cl.
CPC ...... *G01B 11/2527* (2013.01); *G01B 11/2513* (2013.01); *G01N 21/55* (2013.01); *G01N 21/8806* (2013.01); *G01N 21/8851* (2013.01); *G06T 7/0004* (2013.01); *G01N 2021/8816* (2013.01); *G01N 2021/8829* (2013.01); *G01N 2021/8887* (2013.01); *G06T 2207/10016* (2013.01); *G06T 2207/10152* (2013.01); *G06T 2207/30108* (2013.01)

(58) Field of Classification Search
CPC ......................................................... G03F 1/84
See application file for complete search history.

(56) References Cited

U.S. PATENT DOCUMENTS

| | | | | |
|---|---|---|---|---|
| 6,100,990 | A | 8/2000 | Ladewski | |
| 2015/0204797 | A1* | 7/2015 | Colle | G01N 21/90 356/239.4 |

OTHER PUBLICATIONS

U.S. Appl. No. 15/957,937, filed Apr. 20, 2018 (129 pages).
U.S. Appl. No. 15/955,735, filed Apr. 18, 2018 (127 pages).
U.S. Appl. No. 15/956,775, filed Apr. 19, 2018 (215 pages).
U.S. Appl. No. 15/957,938, filed Apr. 20, 2018 (217 pages).

* cited by examiner

*Primary Examiner* — Michelle M Iacoletti
(74) *Attorney, Agent, or Firm* — Kilyk & Bowersox, P.L.L.C.

(57) ABSTRACT

To make it possible to set a shift direction of phases of illuminance distributions of pattern lights to an appropriate direction and perform an inspection at high accuracy while improving setting flexibility of an illuminating section and an imaging section. A phase shift direction of pattern light irradiated from a pattern light illuminating section is determined according to moving direction information concerning a moving direction of an inspection target object with respect to an array direction of light receiving elements and positional relation information concerning a positional relation between the light receiving elements and the pattern light illuminating section.

6 Claims, 48 Drawing Sheets

Y DIRECTION

A1~A12

X DIRECTION

X-DIRECTION PATTERN LIGHT
IRRADIATION IN CASE OF 0°

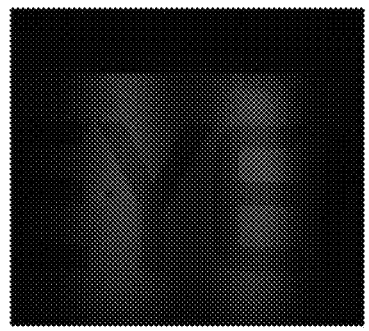

Y-DIRECTION PATTERN LIGHT
IRRADIATION IN CASE OF 0°

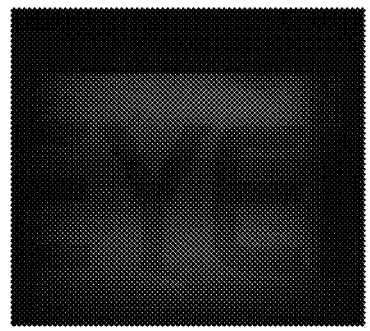

X-DIRECTION PATTERN LIGHT
IRRADIATION IN CASE OF 90°

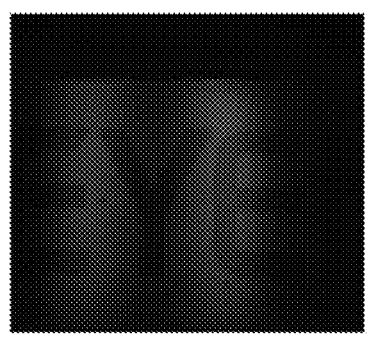

Y-DIRECTION PATTERN LIGHT
IRRADIATION IN CASE OF 90°

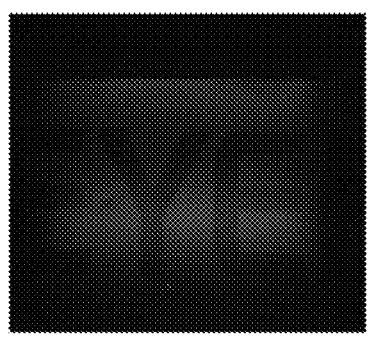

X-DIRECTION PATTERN LIGHT
IRRADIATION IN CASE OF 180°

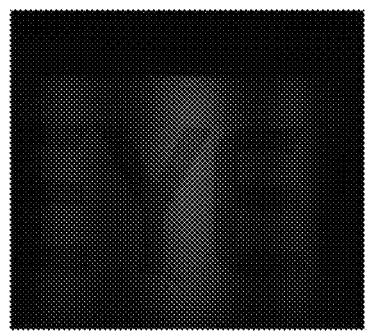

Y-DIRECTION PATTERN LIGHT
IRRADIATION IN CASE OF 180°

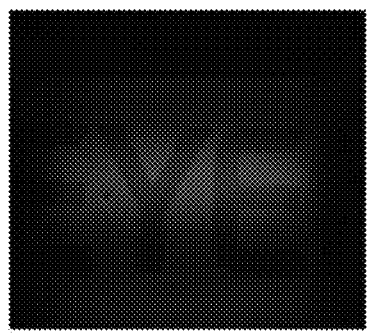

X-DIRECTION PATTERN LIGHT
IRRADIATION IN CASE OF 270°

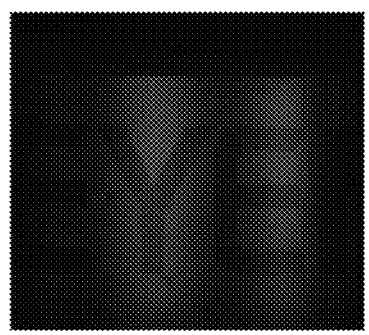

Y-DIRECTION PATTERN LIGHT
IRRADIATION IN CASE OF 270°

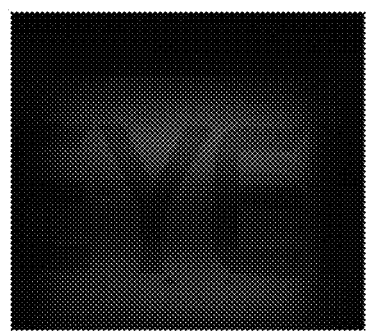

|  | SHADING CORRECTION FILTER | MEDIAN FILTER |
|---|---|---|
| SHAPE IMAGE | × | × |
| GLOSSY RATIO IMAGE | × | ○ |
| DEPTH CONTOUR IMAGE | × | ○ |
| PHASE IMAGE (CORRECTED) | × | ○ |
| SPECULAR REFLECTION COMPONENT IMAGE | ○ | ○ |
| DIFFUSE REFLECTION COMPONENT IMAGE | ○ | ○ |
| NORMAL IMAGE | ○ | ○ |

FIG. 53
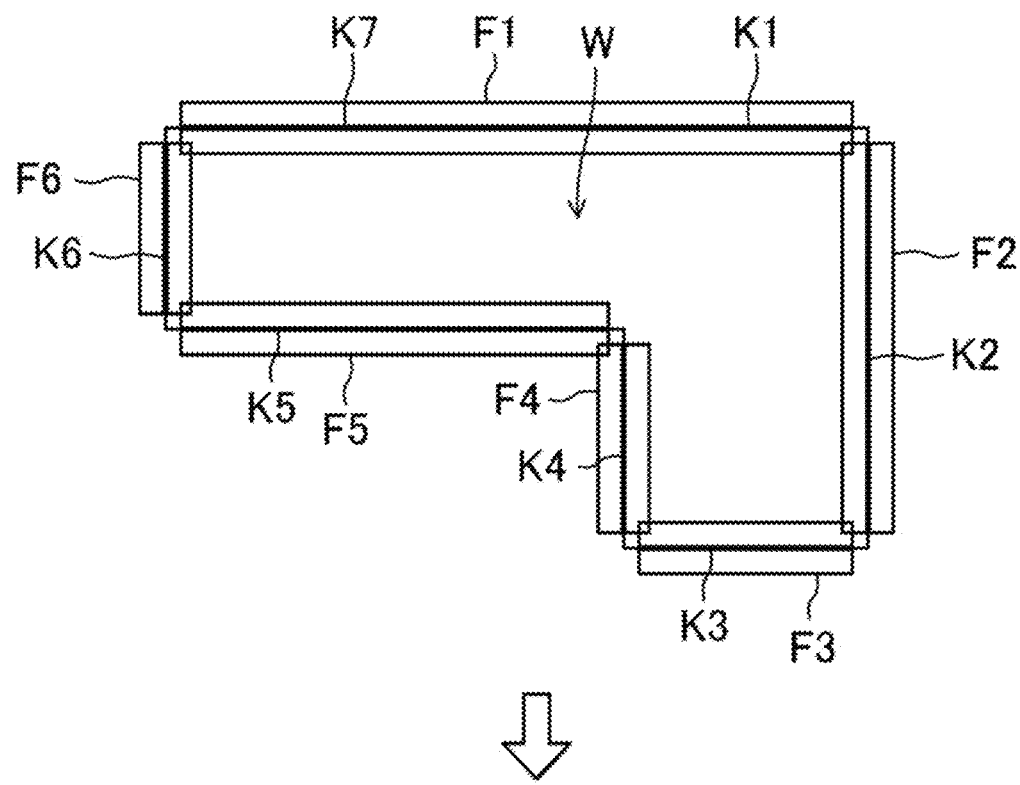
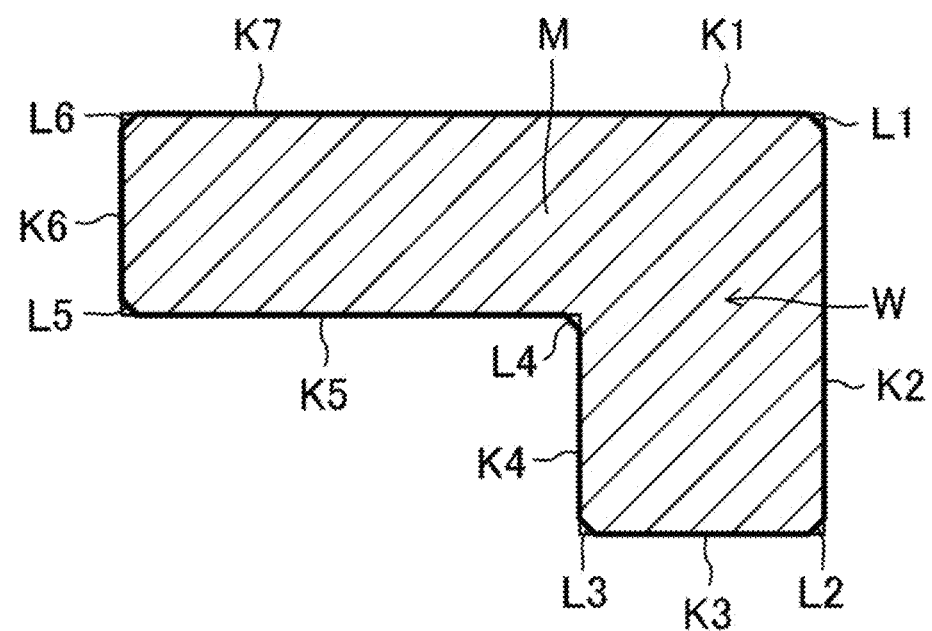

IMAGE INSPECTION APPARATUS

CROSS-REFERENCE TO RELATED APPLICATIONS

The present application claims foreign priority based on Japanese Patent Application No. 2017-107354, filed May 31, 2017, the contents of which is incorporated herein by reference.

BACKGROUND OF THE INVENTION

1. Field of the Invention

The present invention relates to an image inspection apparatus that inspects a defect of an inspection target object using an image obtained by imaging the inspection target object.

2. Description of Related Art

There has been known an image inspection apparatus that irradiates light on the surface of an inspection target object from an illuminating section, receives reflected light in an imaging section, analyzes a luminance distribution of the received light, and inspects a defect such as a flaw present in the inspection target object. In this image inspection apparatus, it is necessary to adjust the positions and the like of the illuminating section and the imaging section to be appropriate positions during setting such that an image of the inspection target object can be correctly captured.

U.S. Pat. No. 6,100,990 (Patent Literature 1) discloses an image inspection apparatus applied with a so-called deflectometry principle.

The image inspection apparatus includes an illuminating section configured to irradiate pattern light, the illuminance of which periodically changes, on an inspection target object and an imaging section configured to image the inspection target object on which the pattern light is irradiated. The illuminating section sequentially irradiates a plurality of pattern lights, phases of illuminance distributions of which are shifted. Every time the pattern light is irradiated, the imaging section images the inspection target object and generates, on the basis of an obtained plurality of luminance images, phase data indicating the shape of the inspection target object. By generating an image for inspection on the basis of the phase data and using the image for inspection, it is possible to perform a defect inspection related to the shape of the inspection target object.

Incidentally, in the case of an image inspection applied with the deflectometry principle, a plurality of pattern lights, phases of illuminance distributions of which are shifted, are sequentially irradiated and imaging is performed every time the pattern light is irradiated. For example, when a moving inspection target object is imaged by a line camera in which light receiving elements are arrayed on a line, a shift direction of the phases of the illuminance distributions needs to be set in a moving direction of the inspection target object (referred to as Y direction), a direction orthogonal to the moving direction in plan view of the inspection target object (referred to as X direction), or the like. A reason for this relates to an algorithm for generating an image for inspection and, in general, when the algorithm is configured, image processing is performed assuming that the shift direction of the phases of the illuminance distributions of the pattern lights is the X direction or the Y direction.

That is, although a shift direction of phases of illuminance distributions of pattern lights is assumed as the X direction in an algorithm of an image inspection applied with the deflectometry principle, when a shift direction of the phases of the illuminance distributions of the pattern lights during operation is a direction different from the X direction by 90°, the shift direction of the phases of the illuminance distributions is a direction different from the direction assumed in the algorithm. When illumination and imaging are repeated in this state, although a plurality of luminance images can be obtained, an image for inspection is generated on the basis of luminance images captured under an inappropriate condition. Therefore, in some case, a recess present in an inspection target object less easily appears in the image for inspection, the recess should be displayed in black but is displayed in white to the contrary, or the recess is displayed in a mixed state of white and black. This causes deterioration in inspection accuracy.

In particular, as described in Patent Literature 1, when the illuminating section and the imaging section are separate, a user can freely set the illuminating section and the imaging section. On the other hand, it is assumed that the shift direction of the phases of the illuminance distributions of the pattern lights is easily set to be a direction different from the direction assumed in the algorithm. It is more likely that the image for inspection is generated under the inappropriate condition explained above. Since the illumination and the imaging are executed even under the inappropriate condition, the user sometimes less easily notices the inappropriate condition. It is likely that the inspection is performed while the user does not notice the inappropriate condition.

If the user notices that the illuminating section is set such that the shift direction of the phases of the illuminance distributions of the pattern lights is a direction different from the direction assumed in the algorithm, the user only has to reset the illuminating section such that the shift direction of the phases of the illuminance distributions is an appropriate direction. However, the illuminating section is sometimes set in a place where the user cannot easily reach. Therefore, the resetting of the illuminating section is time-consuming work. It also sometimes takes time to reset the imaging section.

Because of limitation of a setting place and a relation of wiring, the illuminating section and the imaging section sometimes can only be set such that the shift direction of the phases of the illuminance distributions of the pattern lights is a direction different from the direction assumed in the algorithm. In this case, the image inspection itself applied with the deflectometry cannot be performed.

SUMMARY OF THE INVENTION

The present invention has been devised in view of such points, and an object of the present invention is to make it possible to set the shift direction of the phases of the illuminance distributions of the pattern lights to an appropriate direction and perform an inspection at high accuracy while improving setting flexibility of the illuminating section and the imaging section.

In order to achieve the object, the present invention provides an image inspection apparatus that inspects a defect of an inspection target object using an image obtained by imaging the inspection target object moving in one direction. The image inspection apparatus includes: a pattern light illuminating section for irradiating pattern light having a periodic illuminance distribution on the inspection target object; an imaging section configured to be capable of being set independently from the pattern light illuminating section and including a line camera that includes a plurality of image receiving elements arrayed in a line shape and is capable of being set such that an array direction of the light receiving elements is a direction orthogonal to the moving direction of the inspection target object; a control section configured to control the pattern light illuminating section and the imaging section to generate a plurality of pattern lights, phases of illuminance distributions of which are shifted in the array direction of the light receiving elements, and a plurality of pattern lights shifted in the moving direction of the inspection target object, sequentially irradiate the pattern lights on the inspection target object, image the inspection target object at timings when the pattern lights are irradiated, and obtain a plurality of luminance images; an image generating section configured to generate, on the basis of a deflectometry principle, phase data of a surface of the inspection target object from the plurality of luminance images captured by the imaging section and generate, on the basis of the phase data, an image for inspection indicating a shape of the inspection target object; and an information acquiring section configured to acquire moving direction information concerning the moving direction of the inspection target object with respect to the array direction of the light receiving elements of the line camera and positional relation information concerning a positional relation between the light receiving elements of the line camera and the pattern light illuminating section. The control section is configured to determine, according to the moving direction information and the positional relation information acquired by the information acquiring section, a phase shift direction of the pattern lights irradiated by the pattern light illuminating section.

With this configuration, the plurality of pattern lights shifted in one direction are sequentially irradiated on the inspection target object. Every time the pattern light is irradiated, the inspection target object is imaged to generate the plurality of luminance images. The phase data of the surface of the inspection target object is generated on the basis of the plurality of luminance images. The image for inspection indicating the shape of the inspection target object is generated. Therefore, it is possible to perform an image inspection applied with the deflectometry principle.

Even if the pattern light illuminating section and the imaging section are set such that the shift direction of the phases of the illuminance distributions is a direction different from the direction assumed in the algorithm, it is possible to set the phase shift direction of the pattern lights irradiated by the pattern light illuminating section to an appropriate direction according to the moving direction information concerning the moving direction of the inspection target object with respect to the array direction of the light receiving elements of the line camera and the positional relation information concerning the positional relation between the light receiving elements of the line camera and the pattern light illuminating section. Therefore, it is unnecessary to reset the pattern light illuminating section and the imaging section. Even if the pattern light illuminating section can only be set because of limitation of a setting place and a relation of wiring such that the shift direction of the phases of the illuminance distributions is a direction different from the direction assumed in the algorithm, it is possible to perform the image inspection applied with the deflectometry principle.

The present invention provides an image inspection apparatus that inspects a defect of an inspection target object using an image obtained by imaging the inspection target object moving in one direction. The image inspection apparatus includes: a pattern light illuminating section for irradiating pattern light having a periodic illuminance distribution on the inspection target object; an imaging section configured to be capable of being set independently from the pattern light illuminating section and including a line camera that includes a plurality of image receiving elements arrayed in a line shape and is capable of being set such that an array direction of the light receiving elements is a direction orthogonal to the moving direction of the inspection target object; a control section configured to control the pattern light illuminating section and the imaging section to generate a plurality of pattern lights, phases of illuminance distributions of which are shifted in the array direction of the light receiving elements and the moving direction of the inspection target object, sequentially irradiate the pattern lights on the inspection target object, image the inspection target object at timings when the pattern lights are irradiated, and obtain a plurality of luminance images; an image generating section configured to generate, on the basis of a deflectometry principle, phase data of a surface of the inspection target object from the plurality of luminance images captured by the imaging section and generate, on the basis of the phase data, an image for inspection indicating a shape of the inspection target object; and an information acquiring section configured to acquire moving direction information concerning the moving direction of the inspection target object with respect to the array direction of the light receiving elements of the line camera and positional relation information concerning a positional relation between the light receiving elements of the line camera and the pattern light illuminating section. The image generating section is configured to generate, according to the moving direction information and the positional relation information acquired by the information acquiring section, the image for inspection related to the shape of the inspection target object.

With this configuration, even if the pattern light illuminating section and the imaging section are set such that the shift direction of the phases of the illuminance distributions is a direction different from the direction assumed in the algorithm, it is possible to generate the image for inspection related to the shape of the inspection target object according to the moving direction information concerning the moving direction of the inspection target object with respect to the array direction of the light receiving elements of the line camera and the positional relation information concerning the positional relation between the light receiving elements of the line camera and the pattern light illuminating section. Therefore, it is unnecessary to reset the pattern light illuminating section and the imaging section. Even if the pattern light illuminating section can only be set because of limitation of a setting place and a relation of wiring such that the shift direction of the phases of the illuminance distributions is a direction different from the direction assumed in the algorithm, it is possible to perform the image inspection applied with the deflectometry principle.

The positional relation information can include a positional relation of reflected light reception in which the light receiving elements receive the pattern lights irradiated from the pattern light illuminating section and reflected on the inspection target object and a positional relation of transmitted light reception in which the light receiving elements receive the pattern lights irradiated from the pattern light illuminating section and transmitted through the inspection target object.

When a direction orthogonal to the array direction of the light receiving elements when viewed from a light reception side of the line camera is set as an up-down direction of the line camera, the moving direction information can include the up-down direction of the line camera and the moving direction of the inspection target object.

The information acquiring section can be configured to control, during setting of the image inspection apparatus performed before the image inspection apparatus is operated, the pattern light illuminating section and the imaging section to generate a first image obtained by imaging an irradiation surface on which first pattern light having a periodic illuminance distribution in one direction is irradiated and a second image obtained by imaging an irradiation surface on which second pattern light having a periodic illuminance distribution in a direction orthogonal to the one direction is irradiated. The information acquiring section can be configured to analyze the first image and the second image to thereby acquire positional relation information concerning a positional relation between the light receiving elements of the line camera and the pattern light illuminating section.

The control section can be configured to control the pattern light illuminating section and the imaging section to generate a plurality of pattern lights, phases of illuminance distributions of which are shifted in both directions of the array direction of the light receiving elements and the moving direction of the inspection target object, and sequentially irradiate the pattern lights on the inspection target object and, every time the pattern light is irradiated, image the inspection target object to generate a plurality of luminance images.

According to the present invention, it is possible to freely set the pattern light illuminating section and the imaging section without worrying about a phase shift direction of pattern light. Consequently, it is possible to perform an inspection at high accuracy while improving setting flexibility of the pattern light illuminating section and the imaging section.

BRIEF DESCRIPTION OF THE DRAWINGS

FIG. 23 is a diagram showing an example of an actual luminance image;

FIG. 47 is a diagram showing processing performed when an inspection target object is a bead or the like;

FIG. 53 is a diagram for explaining a procedure for setting substantially the entire work as the inspection target region;

DESCRIPTION OF EMBODIMENTS

Embodiments of the present invention are explained in detail below with reference to the drawings. Note that the following explanation of preferred embodiments is essentially only illustration and is not meant to limit the present invention, objects to which the present invention is applied, or uses of the present invention.

First Embodiment

Overall Configuration of an Image Inspection Apparatus 1

Figure 1:
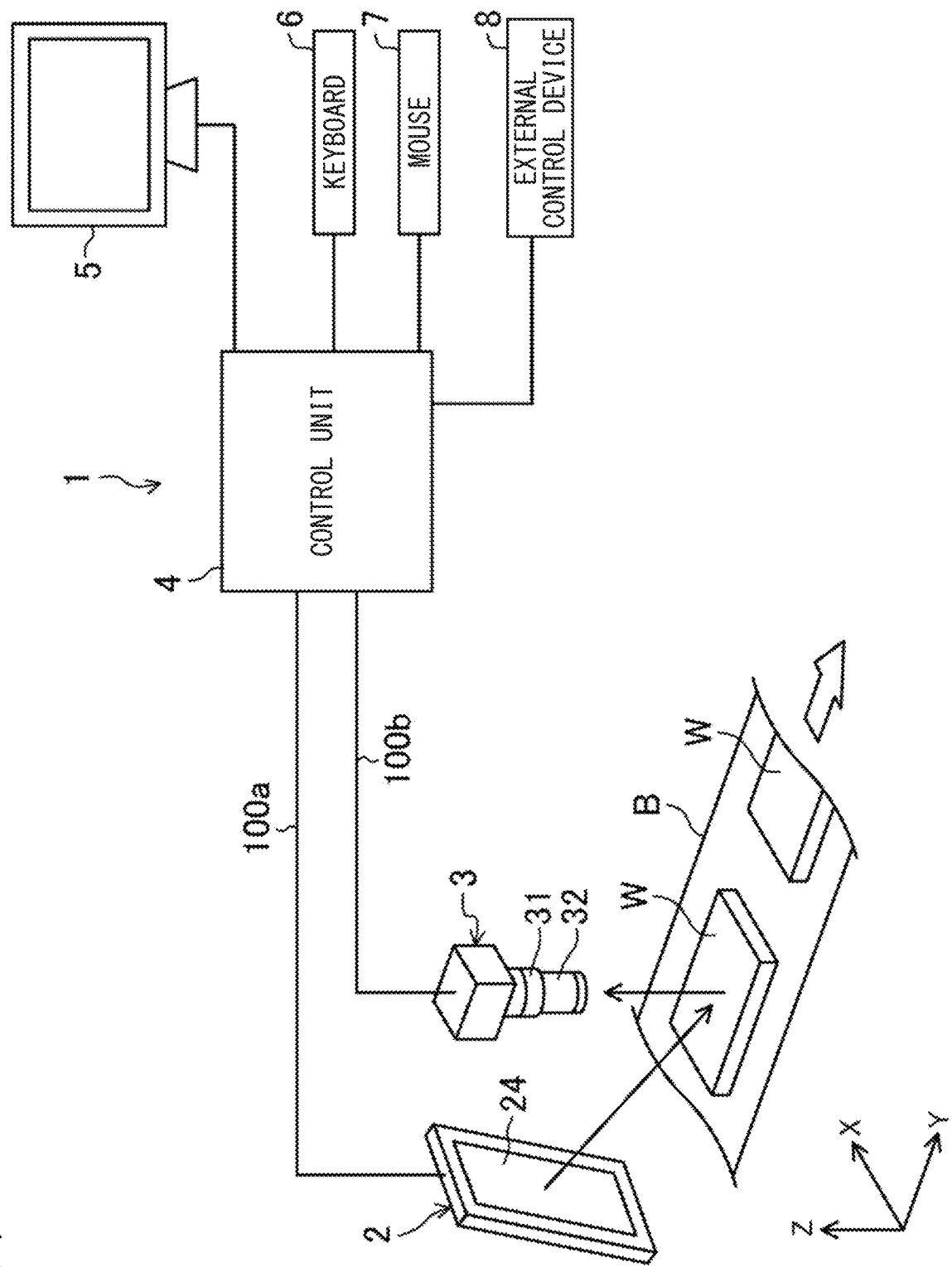
FIG. 1 is a diagram schematically showing an operation state of an image inspection apparatus according to a first embodiment.

FIG. 1 is a diagram schematically showing an operation state of an image inspection apparatus 1 according to an embodiment of the present invention. The image inspection apparatus 1 is configured to inspect a defect of work W using an image obtained by imaging the work W (an inspection target object) moving in one direction. Specifically, the image inspection apparatus 1 includes at least a pattern light illuminating section 2 that executes pattern light illumination for irradiating a plurality of pattern lights on the work W, an imaging section 3, a control unit 4, a display section 5, a keyboard 6, and a mouse 7. The image inspection apparatus 1 can include devices other than these devices. For example, an external control device 8 configured from a programmable logic controller (PLC) or the like is connected to the control unit 4. The external control device 8 may configure a part of the image inspection apparatus 1. The external control device 8 does not have to be a component of the image inspection apparatus 1.

In FIG. 1, a plurality of works W are conveyed in a direction indicated by a white arrow in FIG. 1 in a state in which the plurality of works W are placed on the upper surface of a belt conveyor for conveyance B. The work W is an inspection target object. The external control device 8 is a device for performing sequence control of the belt conveyor for conveyance B and the image inspection apparatus 1. A general-purpose PLC can be used as the external control device 8.

Note that, in the explanation of this embodiment, a conveying direction of the work W by the belt conveyor for conveyance B (a moving direction of the work W) is defined as a Y direction, a direction orthogonal to the Y direction in plan view of the belt conveyor for conveyance B is defined as an X direction, and a direction orthogonal to the X direction and the Y direction (a direction orthogonal to the upper surface of the belt conveyor for conveyance B) is defined as a Z direction. However, this is only definition for achieving convenience of explanation.

The image inspection apparatus 1 can be used when an exterior inspection of the work W is performed, that is, presence or absence of a defect such as a scratch, a stain, or a dent on the surface of the work W is inspected. During the operation of the image inspection apparatus 1, the image inspection apparatus 1 receives, from the external control device 8, via a signal line, an inspection start trigger signal for specifying start timing of a defect inspection. The image inspection apparatus 1 performs imaging, illumination, and the like of the work W on the basis of the inspection start trigger signal and obtains an image for inspection after predetermined processing. Thereafter, an inspection result is transmitted to the external control device 8 via the signal line. In this way, during the operation of the image inspection apparatus 1, input of an inspection start trigger signal and output of an inspection result are repeatedly performed via the signal line between the image inspection apparatus 1 and the external control device 8. Note that the input of the inspection start trigger signal and the output of the inspection result may be performed via the signal line between the image inspection apparatus 1 and the external control device 8 as explained above or may be performed via a not-shown signal line other than the signal line. For example, a sensor for detecting arrival of the work W and the image inspection apparatus 1 may be directly connected to input the inspection start trigger signal from the sensor to the image inspection apparatus 1.

Besides being configured by exclusive hardware, the image inspection apparatus 1 may be configured by a general-purpose apparatus in which software is installed, for example, a general-purpose or exclusive computer in which an image inspection program is installed. In the following example, the image inspection program is installed in an exclusive computer in which hardware such as a graphic board is specialized for image inspection processing.

Configuration of the Pattern Light Illuminating Section 2

The pattern light illuminating section 2 is a section for irradiating pattern light having a periodic illuminance distribution on the work W. The pattern light illuminating section 2 can be configured by, for example, a plurality of light emitting diodes, a liquid crystal panel, an organic EL panel, or a digital micro mirror device (DMD). The pattern light illuminating section 2 can be simply referred to as illuminating section. The liquid crystal panel, the organic EL panel, or the DMD is not shown in the figure. However, a liquid crystal panel, an organic EL panel, or a DMD having structure well-known in the past can be used. The pattern light illuminating section 2 is connected to the control unit 4 via a signal line 100a. The pattern light illuminating section 2 can be set apart from the imaging section 3 and the control unit 4.

When the plurality of light emitting diodes are used in the pattern light illuminating section 2, the plurality of light emitting diodes are arranged in a dot matrix shape. Pattern light having a periodic illuminance distribution can be generated by current value control. In the case of the liquid crystal panel and the organic EL panel, lights irradiated from the panels can be formed as pattern lights having a periodic illuminance distribution by controlling the panels. In the case of the digital micro mirror device, pattern light having a periodic illuminance distribution can be generated and irradiated by controlling a micro mirror surface incorporated in the digital micro mirror device. Note that the configuration of the pattern light illuminating section 2 is not limited to the configurations explained above. A device, an apparatus, and the like that can generate pattern light having a periodic illuminance distribution can be used.

In the following explanation, the pattern light illuminating section 2 including the plurality of light emitting diodes is explained in detail. In this case, the pattern light illuminating section 2 includes a light emitting section 23 (shown in FIG. 3) configured by mounting a two-dimensionally arranged plurality of light emitting diodes 20 and 21 on a substrate 23a and a diffusing member 24 (shown in FIGS. 1, 5A, and 5B) that diffuses lights irradiated from the light emitting diodes 20 and 21. The light emitting section 23 is formed in a substantially rectangular shape as a whole. A light emitting surface of the light emitting section 23 can be imaginarily divided into first to fourth regions S1 to S4 by an imaginary section line J1 extending in the Y direction passing the center in the X direction of the light emitting section 23 and an imaginary section line J2 extending in the X direction passing the center in the Y direction of the light emitting section 23. All of the first to fourth regions S1 to S4 are formed in a substantially rectangular shape having the same size. The regions S1 to S4 can also be referred to as blocks. One block includes 12 (pieces)×12 (rows)×12 (directions) LEDS.

Figure 3:
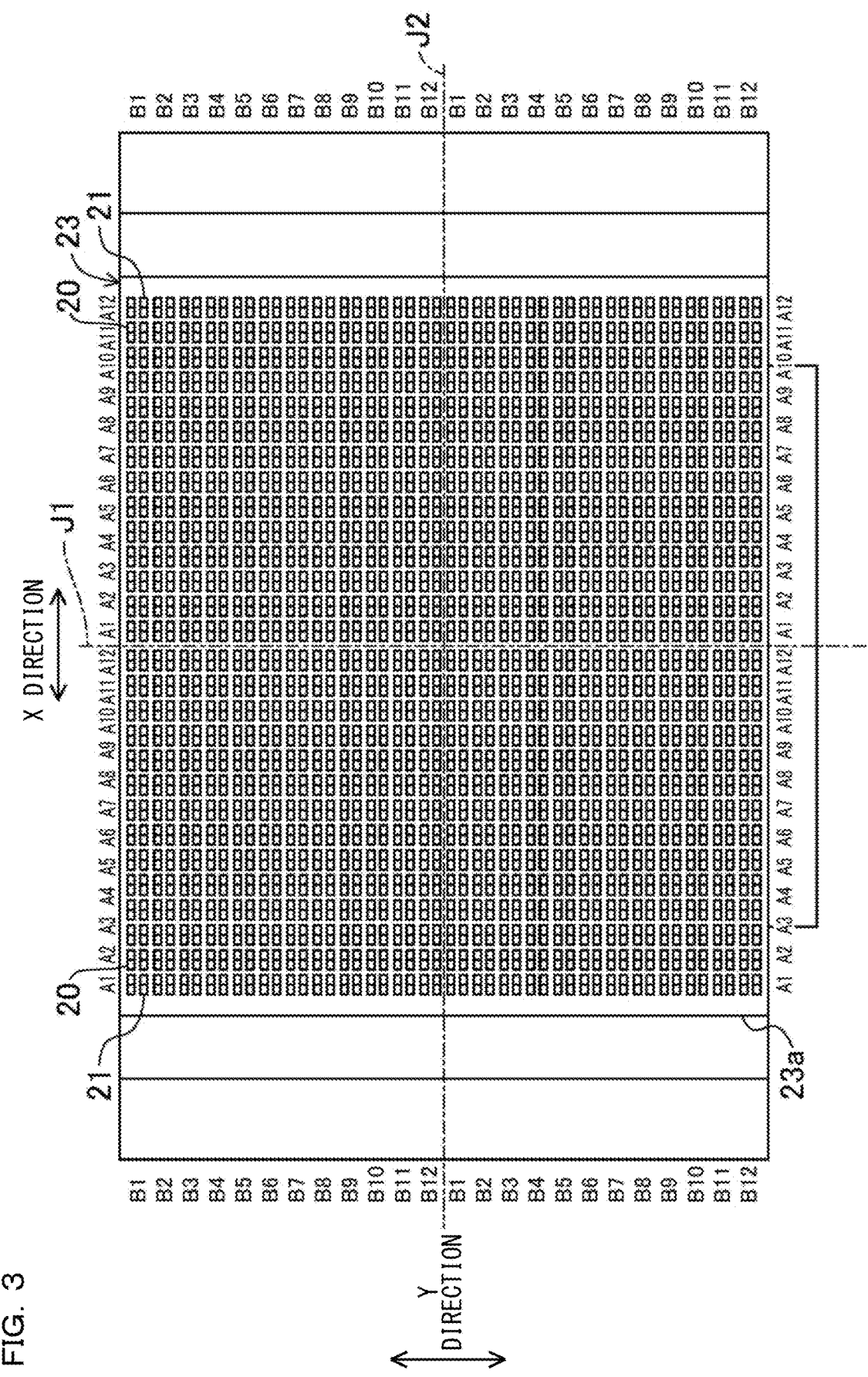
FIG. 3 is a front view of a light emitting section of a pattern light illuminating section.
Figure 4A:
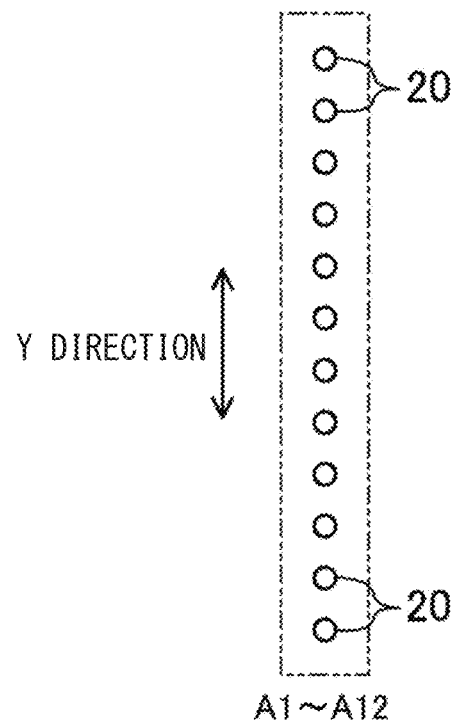
FIG. 4A is a diagram showing a first light emitting diode row.
Figure 4B:
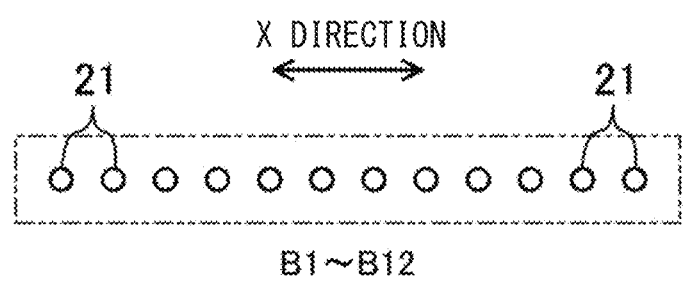
FIG. 4B is a diagram showing a second light emitting diode row.

In the first region S1, first light emitting diode rows A1 to A12 in twelve rows including a plurality of light emitting diodes 20 disposed to be arranged at an equal interval in the Y direction and connected in series as shown in FIG. 4A and second light emitting diode rows B1 to B12 in twelve rows including a plurality of light emitting diodes 21 disposed to be arranged at an equal interval in the X direction and connected in series as shown in FIG. 4B are formed. As shown in FIG. 3, an arranging direction of the first light emitting diode rows A1 to A12 in the first region S1 is the X direction. The first light emitting diode rows A1 to A12 are disposed in parallel to one another. Electric power is individually supplied to the respective first light emitting diode rows A1 to A12.

As shown in FIG. 3, an arranging direction of the second light emitting diode rows B1 to B12 in the first region S1 is the Y direction. The second light emitting diode rows B1 to B12 are disposed in parallel to one another. Electric power is individually supplied to the respective second light emitting diode rows B1 to B12.

The first light emitting diode rows A1 to A12 and the second light emitting diode rows B1 to B12 are disposed to cross each other in the first region S1. The light emitting diodes 20 configuring the first light emitting diode rows A1 to A12 and the light emitting diodes 21 configuring the second light emitting diode rows B1 to B12 are disposed not to overlap in an irradiating direction of light. Consequently, the plurality of light emitting diodes 20 and 21 are disposed in a dot matrix shape in the first region S1.

Since the twelve each of the light emitting diodes 20 and 21 are connected in series to configure the rows A1 to A12 and the rows B1 to B12, control lines are not provided for each of the light emitting diodes 20 and 21. One set of control lines is enough for the rows. In the respective regions of the second region S2, the third region S3, and the fourth region S4, as in the first region S1, the first light emitting diode rows A1 to A12 and the second light emitting diode rows B1 to B12 are disposed to cross each other. That is, in this embodiment, the number of the light emitting diodes 20 and 21 is increased to densely dispose light sources of the light emitting section 23. On the other hand, light emitting diode rows set as control targets may be only light emitting diode rows in ninety-six rows (12 rows×2×4 regions) in total including the first light emitting diode rows A1 to A12 and the second light emitting diode rows B1 to B12 in the first region S1, the first light emitting diode rows A1 to A12 and the second light emitting diode rows B1 to B12 in the second region S2, the first light emitting diode rows A1 to A12 and the second light emitting diode rows B1 to B12 in the third region S3, and the first light emitting diode rows A1 to A12 and the second light emitting diode rows 31 to B12 in the fourth region S4.

The second light emitting diode rows B1 to 312 in the first region S1 and the second light emitting diode rows B1 to B12 in the second region S2 are respectively disposed to be arranged on the same straight line extending in the X direction. The second light emitting diode rows B1 to B12 in the third region S3 and the second light emitting diode rows B1 to B12 in the fourth region S4 are respectively disposed to be arranged on the same straight line extending in the X direction.

The first light emitting diode rows A1 to A12 in the first region S1 and the first light emitting diode rows A1 to A12 in the third region S2 are respectively disposed to be arranged on the same straight line extending in the Y direction. The first light emitting diode rows A1 to A12 in the second region S2 and the first light emitting diode rows A1 to A12 in the fourth region S4 are respectively disposed to be arranged on the same straight line extending in the Y direction.

Figure 5A:
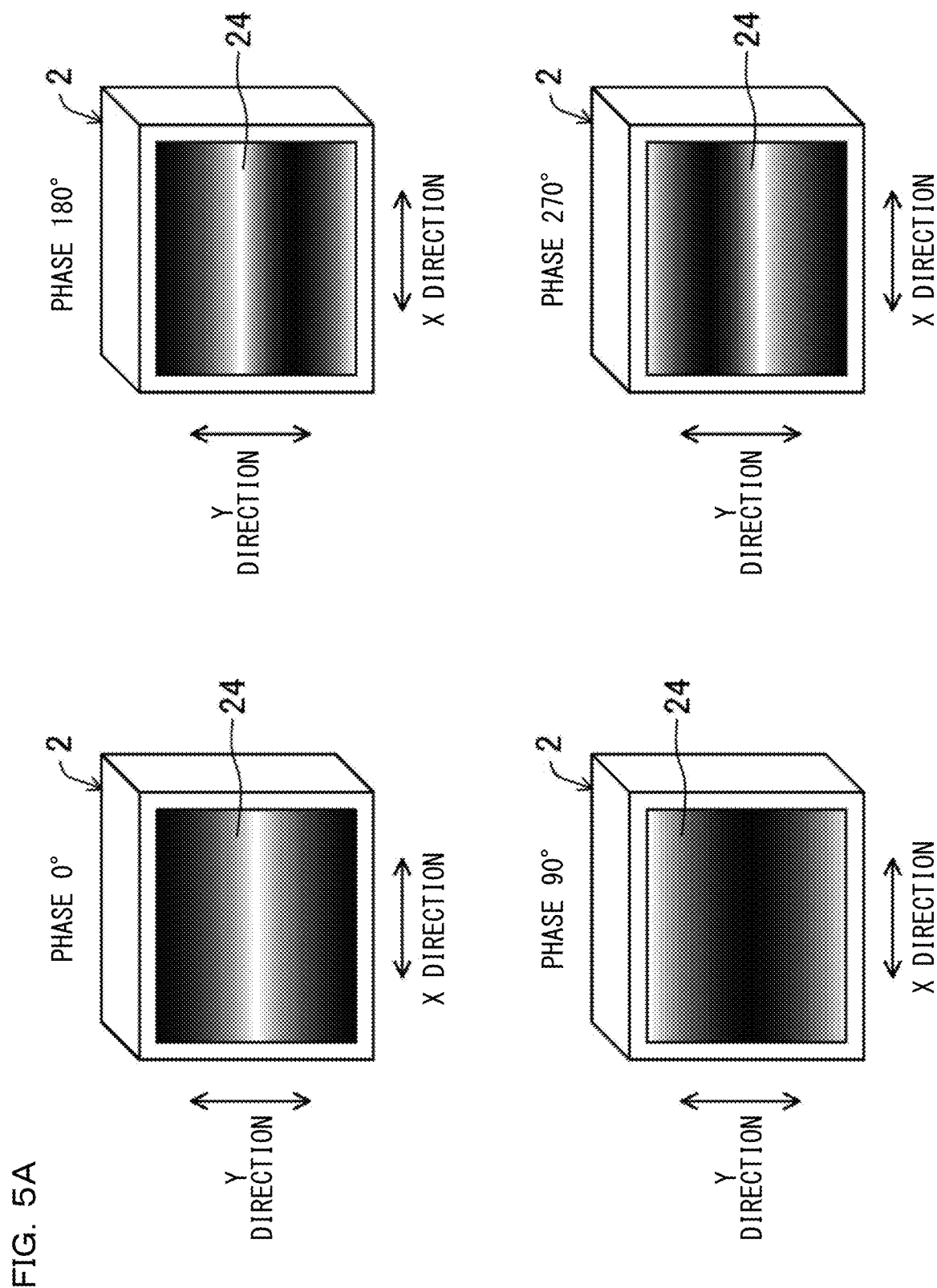
FIG. 5A is a diagram showing an irradiation state of four kinds of Y-direction pattern lights, for each of which a phase of an illuminance distribution is changed by 90°.
Figure 5B:
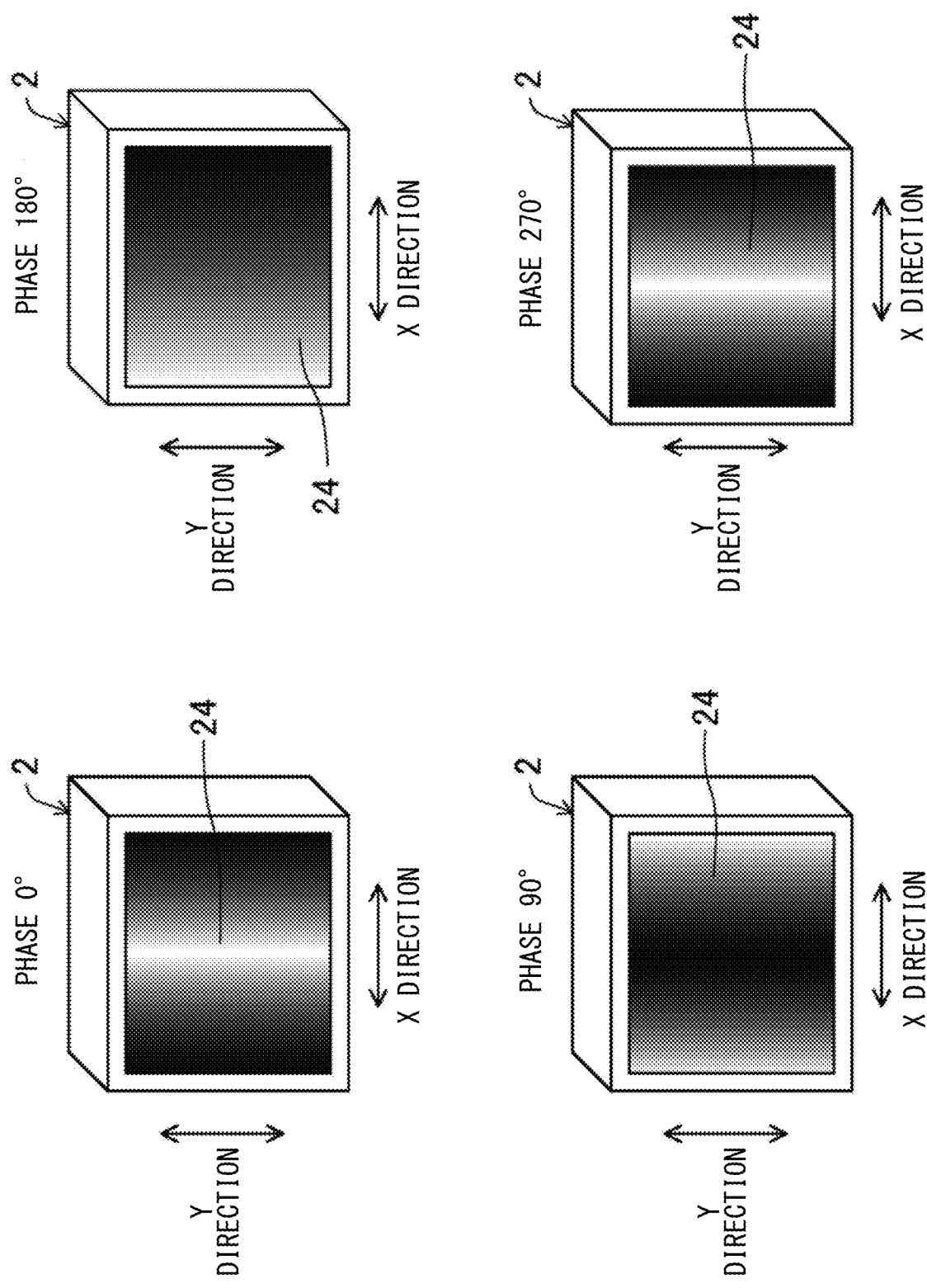
FIG. 5B is a diagram showing an irradiation state of four kinds of X-direction pattern lights, for each of which a phase of an illuminance distribution is changed by 90°.

The diffusing member 24 shown in FIGS. 5A and 5B and the like is configured by a light transmissive plate material disposed to be capable of covering all of the light emitting diodes 20 and 21 in the first to fourth regions S1 to S4. As the plate material configuring the diffusing member 24, a well-known plate material can be used. The diffusing member 24 can diffuse and emit incident light.

By individually controlling values of electric currents fed to the first light emitting diode rows A1 to A12 and the second light emitting diode rows B1 to B12 in the first to fourth regions S1 to S4, it is possible to generate a Y-direction pattern light, the illuminance of which changes in the Y direction and is uniform in the X direction as shown in FIG. 5A, and an X-direction pattern light, the illuminance of which changes in the X direction and is uniform in the Y direction as shown in FIG. 5B. Since the light emitting diodes 20 and 21 are disposed in the dot matrix shape as explained above, light sources are disposed in a dot shape in the light emitting section 23. However, since the diffusing member 24 is provided, lights of the light emitting diodes 20 and 21 are diffused and irradiated to the outside. As shown in FIGS. 5A and 5B, the lights can be formed as pattern lights, the illuminance of which gradually changes when viewed from the outside.

As the control of the light emitting diodes 20 and 21, there are, for example, PWM control and control by a current value (current value control). The current value control is particularly desirable. By performing the current value control, it is possible to realize a quick illuminance change sufficiently utilizing high response speed of the light emitting diodes 20 and 21. For example, it is possible to reduce a time interval for switching certain pattern light to another pattern light to a short interval of approximately 2 microseconds.

Note that it is also possible to irradiate light, an illuminance distribution of which is uniform in a plane, by feeding electric currents having the same current value to all the light emitting diodes 20 and 21. When the values of the electric currents fed to all the light emitting diodes 20 and 21 are set the same and changed, it is possible to change a light emission state from a dark surface light emission state to a bright surface light emission state.

In the case of the Y-direction pattern light shown in FIG. 5A, since light and shade changes in the Y direction, the Y-direction pattern light can also be represented as pattern light in which stripe patterns are repeated in the Y direction. When the Y-direction pattern light is generated, by shifting a phase of an illuminance distribution in the Y direction, it is possible to generate a plurality of Y-direction pattern lights, phases of illuminance distributions of which are different. The illuminance distribution of the Y-direction pattern light can also be represented by a waveform approximate to a sine waveform. In this case, for example, by changing the phase by 90° for each of the Y-direction pattern lights, it is possible to generate Y-direction pattern light in the case of 0°, Y-direction pattern light in the case of 90°, Y-direction pattern light in the case of 180°, and Y-direction pattern light in the case of 270°.

In the case of the X-direction pattern light shown in FIG. 5B, since light and shade changes in the X direction, the X-direction pattern light can also be represented as pattern light in which stripe patterns are repeated in the X direction. When the X-direction pattern light is generated, by shifting a phase of an illuminance distribution in the X direction, it is possible to generate a plurality of X-direction pattern lights, phases of illuminance distributions of which are different. The illuminance distribution of the X-direction pattern light can also be represented by a waveform approximate to a sine waveform. In this case, for example, by changing the phase by 90° for each of the X-direction pattern lights, it is possible to generate X-direction pattern light in the case of 0°, X-direction pattern light in the case of 90°, X-direction pattern light in the case of 180°, and X-direction pattern light in the case of 270°. That is, the pattern light illuminating section 2 can illuminate the work W in different illumination forms.

When deflectometry processing explained below is performed, the pattern light irradiated on the work W is not limited to the sine waveform. Pattern light of a triangular wave or the like is also possible.

The length of one side of the light emitting section 23 can be set to, for example, 100 mm. Twenty-four each of the light emitting diodes 20 and 21 are disposed longitudinally and laterally on the inner side of a 10 mm square. By performing current value control of the light emitting diodes 20 and 21, it is possible to generate high-gradation pattern light at high speed. Note that the length of one side of the light emitting section 23, the number of the light emitting diodes 20 and 21, the number of rows, the number of regions of the light emitting section 23 are examples and are not particularly limited. When an illuminance distribution of pattern light can be represented by a waveform approximate to a sine waveform, the length of one side of the light emitting section 23 can be set to one wavelength of the sine waveform.

Configuration of the Imaging Section 3

Figure 2:
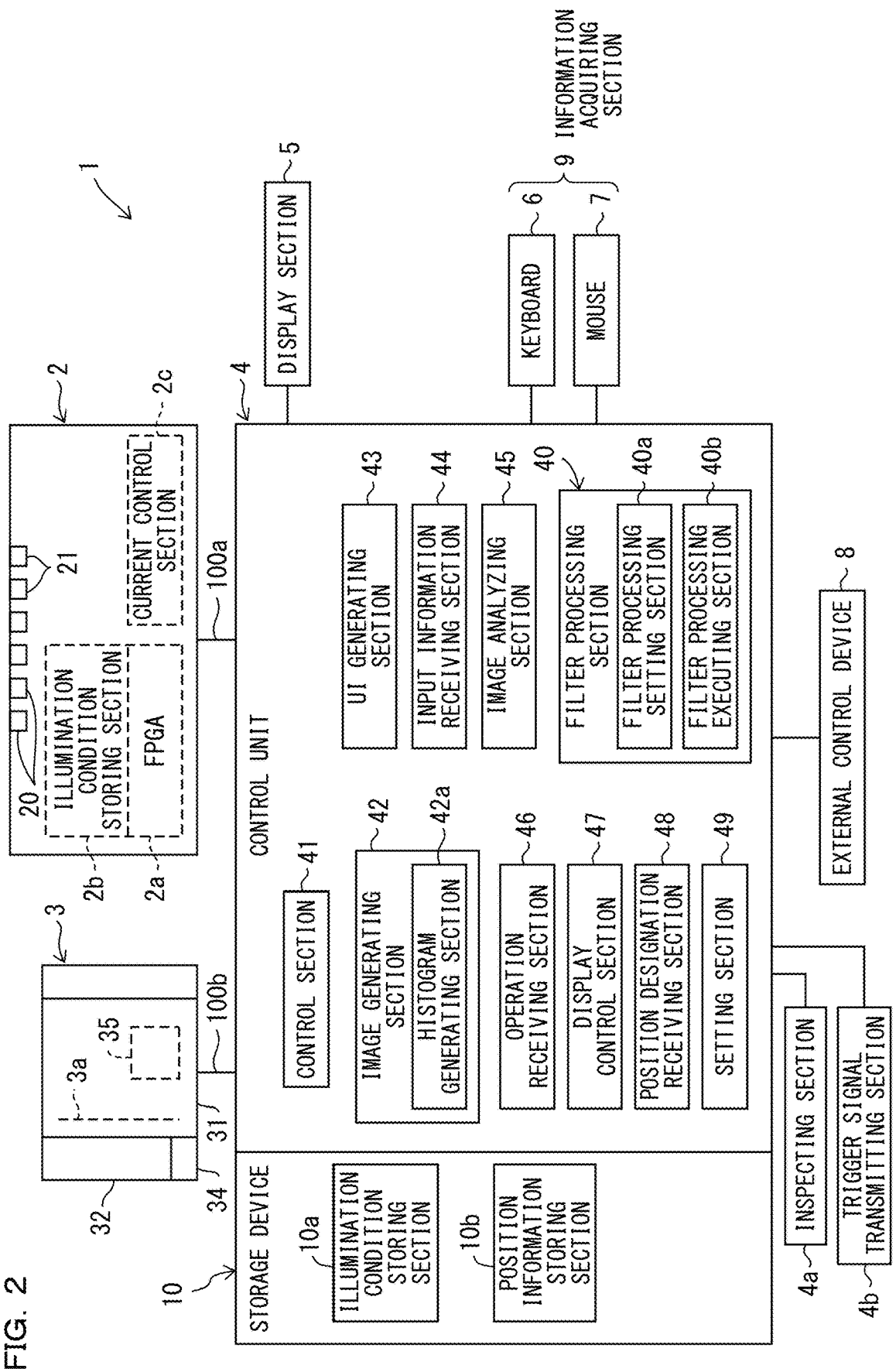
FIG. 2 is a block diagram of the image inspection apparatus according to the first embodiment.

As shown in FIG. 2, the imaging section 3 includes a plurality of light receiving elements 3a arrayed in a line shape and includes a line camera 31 that can be set such that an array direction of the light receiving elements 3a is a direction (the X direction) orthogonal to the moving direction of the work W (the Y direction) and a light-condensing-system optical system 32. The light receiving element 3a is an image sensor configured by an imaging element such as a CCD (charge-coupled device) or a CMOS (complementary metal oxide semiconductor) that converts the intensity of light obtained through the light-condensing-system optical system 32 into an electric signal. The light-condensing-system optical system 32 is an optical system for condensing light made incident from the outside. The light-condensing-system optical system 32 typically includes one or more optical lenses.

The imaging section 3 is connected to the control unit 4 via a signal line 100b separate from the signal line 100a of the pattern light illuminating section 2. The imaging section 3 can be set to be separated from the pattern light illuminating section 2 and the control unit 4. That is, the imaging section 3 is configured to be capable of being set independently from the pattern light illuminating section 2. The signal line 100b of the imaging section 3 may be divided from the signal line 100a of the pattern light illuminating section 2.

An imaging trigger signal transmitted from a control section 41 of the control unit 4 is input to the imaging section 3 via the signal line 100b. The imaging section 3 is configured to execute imaging every time the imaging section 3 receives the imaging trigger signal. The imaging trigger signal is explained below.

As shown in FIG. 1, in the case of the work W having a plane shape, a positional relation between the imaging section 3 and the pattern light illuminating section 2 can be set such that pattern light irradiated from the pattern light illuminating section 2 toward the surface of the work W is reflected on the surface of the work W and made incident on the light-condensing-system optical system 32 of the imaging section 3.

Figure 6A:
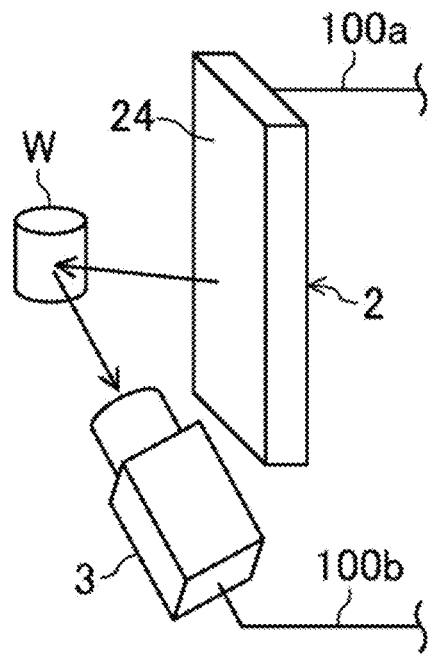
FIG. 6A is a diagram showing a positional relation between an imaging section and the pattern light illuminating section set when work is a cylindrical member.

As shown in FIG. 6A, when the work W is a columnar member, the positional relation between the imaging section 3 and the pattern light illuminating section 2 can also be set such that pattern light irradiated from the pattern light illuminating section 2 toward the surface of the work W is reflected on the surface of the work W and made incident on the light-condensing-system optical system 32 of the imaging section 3.

Figure 6B:
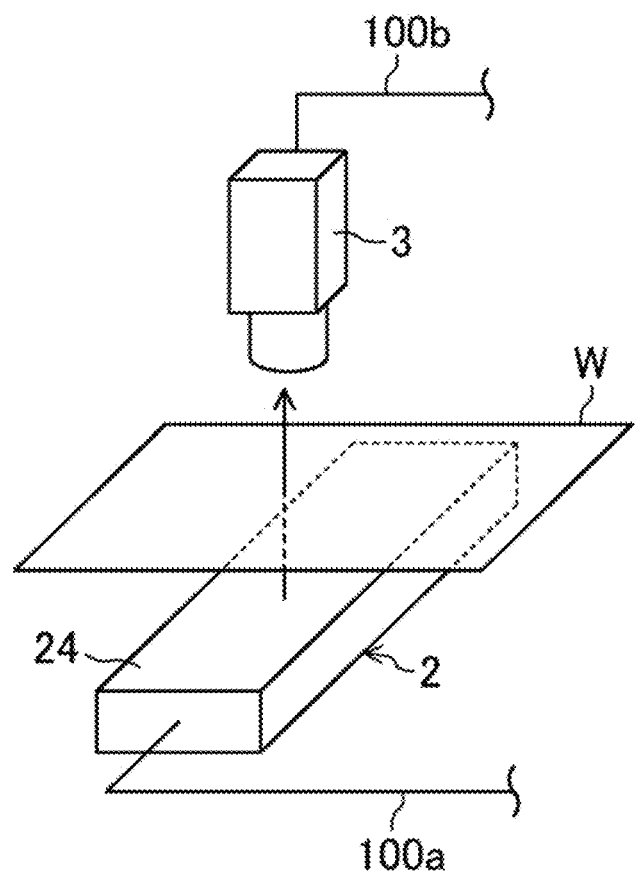
FIG. 6B is a diagram showing a positional relation between the imaging section and the pattern light illuminating section set when work is a member having light transmissivity.

As shown in FIG. 6B, when the work W is a member having light transmittance like a transparent film or sheet, the positional relation between the imaging section 3 and the pattern light illuminating section 2 can be set such that pattern light irradiated from the pattern light illuminating section 2 toward the surface of the work W is transmitted through the work W and made incident on the light-condensing-system optical system 32 of the imaging section 3.

In all the cases explained above, the pattern light illuminating section 2 and the imaging section 3 are disposed such that a specular reflection component reflected on the surface of the work W is made incident on the light-condensing-system optical system 32 of the imaging section 3.

Each of the positional relation between the imaging section 3 and the pattern light illuminating section 2 shown in FIG. 1 and the positional relation between the imaging section 3 and the pattern light illuminating section 2 shown in FIG. 6A is a positional relation of reflected light reception in which the light receiving elements 3a of the line camera 31 receive pattern light irradiated from the pattern light illuminating section 2 and reflected on the work W.

On the other hand, the positional relation between the imaging section 3 and the pattern light illuminating section 2 shown in FIG. 6B is a positional relation of transmitted light reception in which the light receiving elements 3a of the line camera 31 receive pattern light irradiated from the pattern light illuminating section 2 and transmitted through the inspection target object. In this case, the number of times of reflection of the pattern light is zero.

The number of times of reflection of the pattern light is one in the positional relation of the reflected light reception. The number of times of reflection of the pattern light is zero in the positional relation of the transmitted light reception. Instead of the line camera 31, an area camera (a camera in which light receiving elements are disposed side by side in the X direction and the Y direction) can also be used in the imaging section 3. In the case of the area camera, a form of coaxial illumination is also possible. In this case, since reflection on a half mirror is added when reflected light is set, the number of times of reflection is two. By causing a user to input the number of times of reflection of the pattern light, it is possible to determine whether the positional relation is the positional relation of the reflected light reception or the positional relation of the transmitted light reception.

Figure 8:
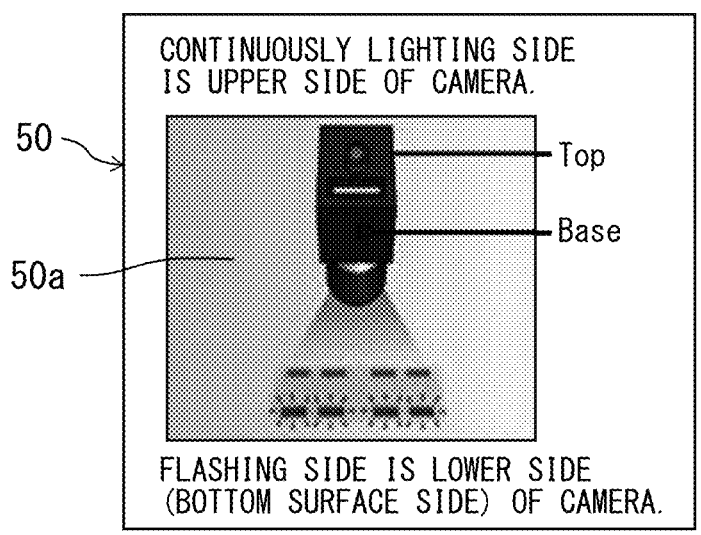
FIG. 8 is a diagram showing an interface for camera up-down confirmation.

As shown in FIG. 2, an LED pointer 34 is provided in the imaging section 3. The LED pointer 34 is a pointer for irradiating pointer light in the axial direction of the light-condensing-system optical system 32. The LED pointer 34 is configured to be capable of switching the pointer light to an irradiation state and a non-irradiation state according to a control signal received from the control unit 4. As an example of an irradiation form of the pointer light, the irradiation form can be set to a form for confirming the up-down direction of the line camera 31 as shown in FIG. 8. In FIG. 8, the pointer light is irradiated respectively on the upper side and the lower side of the line camera 31 to continuously light the upper side and flash the lower side. A form of the pointer light may be any form. For example, characters and the like can be used as the pointer light. A direction orthogonal to the array direction of the light receiving elements 3a when the line camera 31 is viewed from the light reception side can be set as the up-down direction of the line camera 31.

As shown in FIG. 2, a gravitational acceleration sensor 35, which detects gravitational acceleration, is provided in the imaging section 3. The gravitational acceleration sensor 35 is a sensor for grasping a posture of the imaging section 3 (an angle formed by the axial direction of the light-condensing-system optical system 32 and the horizontal plane, an angle formed by the axial direction of the light-condensing-system optical system 32 and the vertical plane, etc.). It is possible to obtain the posture of the imaging section 3 substantially on a real-time basis according to a well-known method in the past making use of an output value of the gravitational acceleration sensor 35.

Configuration of the Display Section 5

The display section 5 is configured from, for example, an organic EL display or a liquid crystal display. The display section 5 is connected to the control unit 4. The display section 5 is configured to be capable of displaying, for example, an image captured by the imaging section 3, various images generated on the basis of the image captured by the imaging section 3, a defect inspection result of the work W, an interface for operation, an interface for various kinds of setting, and a setting value. The display section 5 can also display a plurality of images for inspection or the like at a time.

By configuring the display section 5 as a touch panel, it is possible to impart an input function for various kinds of information to the display section 5.

Configurations of the Keyboard 6 and the Mouse 7

The keyboard 6 and the mouse 7 are devices for computer operation well-known in the past. The keyboard 6 and the mouse 7 are connected to an input information receiving section 44 (shown in FIG. 2) included in the control unit 4. By operating the keyboard 6 or the mouse 7, it is possible to input various kinds of information to the control unit 4. It is possible to select an image or the like displayed on the display section 5.

Specifically, when moving direction information concerning a moving direction of the work W with respect to the array direction of the light receiving elements 3a of the line camera 31 and positional relation information concerning a positional relation between the light receiving elements 3a of the line camera 31 and the pattern light illuminating section 2 are input to the input information receiving section 44 by the operation of the keyboard 6 or the mouse 7, the input information receiving section 44 can receive the moving direction information and the positional relation information input to the input information receiving section 44. The keyboard 6, the mouse 7, and the input information receiving section 44 are the information acquiring section 9 of the present invention.

The moving direction information is the moving direction of the work W illustrated in FIG. 1. The moving direction information can be set to either one of a direction of a white arrow and an opposite direction of the white arrow. When a direction orthogonal to the array direction of the light receiving elements 3a when the line camera 31 is viewed from the light reception side is set as the up-down direction of the line camera 31, the moving direction information can include the up-down direction of the line camera 31 and the moving direction of the work W. The positional relation information includes the positional relation of the reflected light reception and the positional relation of the transmitted light reception.

Note that a device for computer operation such as a voice input device or a touch operation panel can also be used instead of or in addition to the keyboard 6 and the mouse 7.

Configuration of the Control Unit 4

The control unit 4 is a unit for controlling the sections of the image inspection apparatus 1. The control unit 4 can be configured by a CPU, an MPU, a system SLI, a DSP, exclusive hardware, or the like. The control unit 4 is implemented with various functions as explained below. The functions may be realized by a logic circuit or may be realized by executing software.

As shown in FIG. 2, the control unit 4 includes a filter processing section 40, the control section 41, an image generating section 42, a UI generating section 43, an input information receiving section 44, an image analyzing section 45, an operation receiving section 46, a display control section 47, a position designation receiving section 48, and a setting section 49. A storage device 10 is connected to the control unit 4. The storage device 10 can be a part of components of the image inspection apparatus 1 or can be a device separate from the image inspection apparatus 1. The storage device 10 can be configured by a semiconductor memory, a hard disk, or the like. A reading device capable of reading information stored in various storage media such as a CD-ROM and a DVD-ROM can also be provided in the storage device 10.

Configuration of the UI Generating Section 43

The UI generating section 43 is a section for generating various interfaces displayed on the display section 5. Various interfaces generated by the UI generating section 43 are output from the control unit 4 to the display section 5 and displayed on the display section 5.

Figure 7:
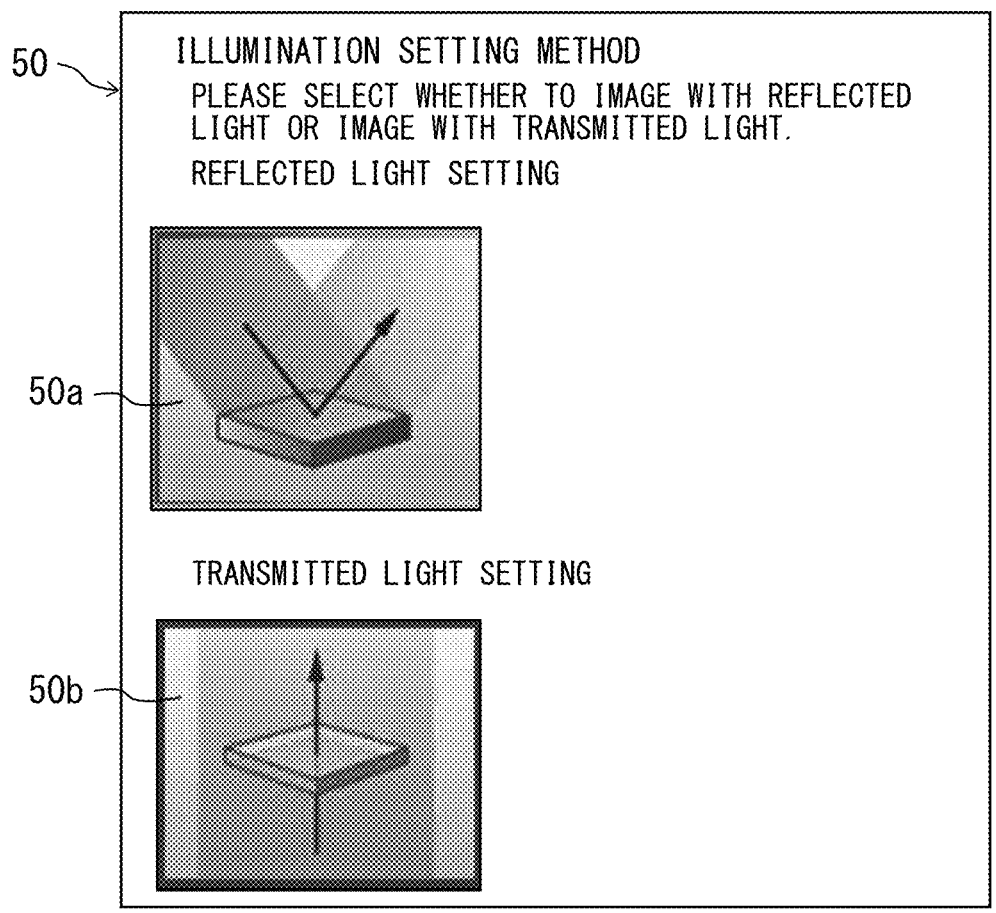
FIG. 7 is a diagram showing an interface for illumination setting method selection.
Figure 9:
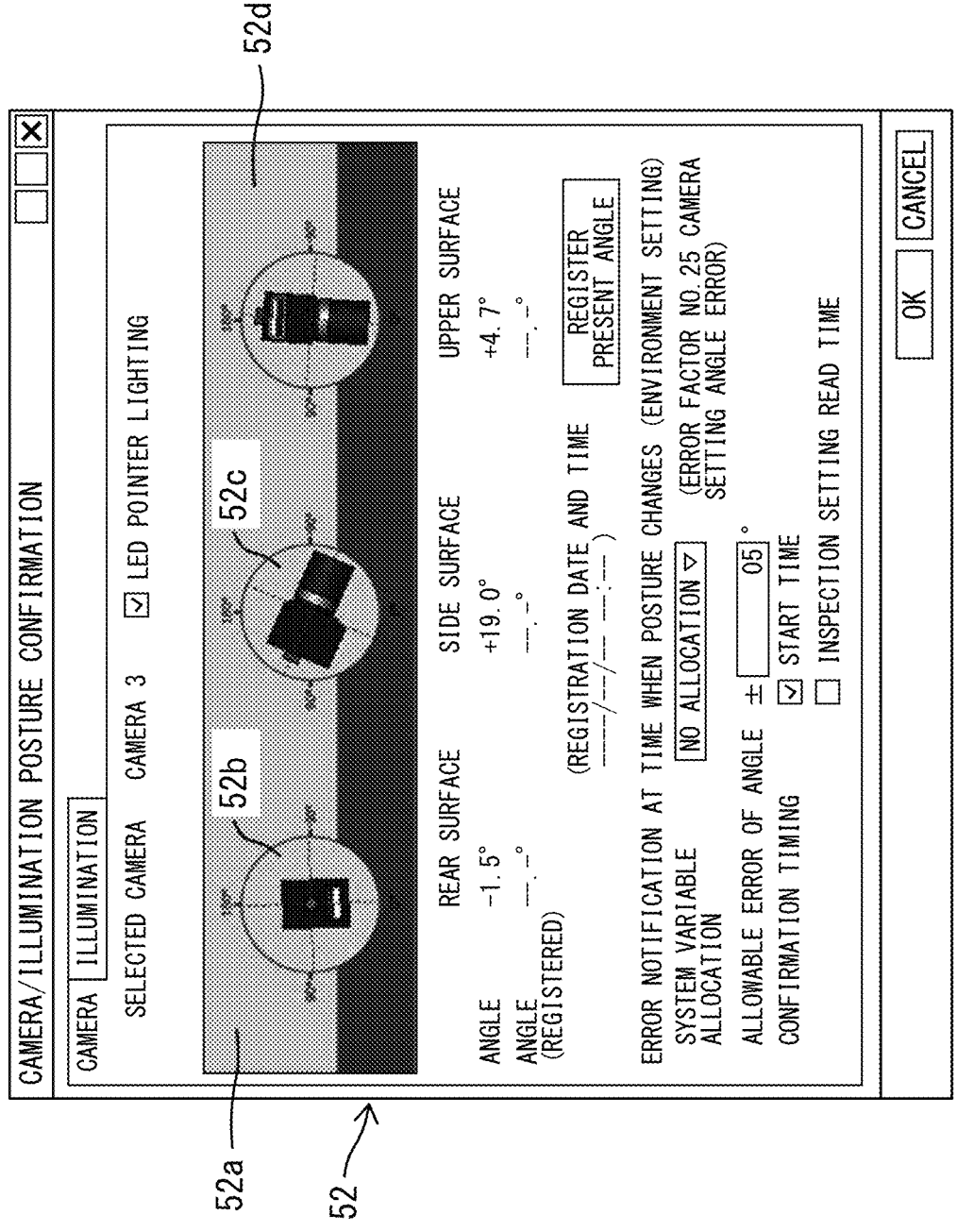
FIG. 9 is a diagram showing an interface for camera posture confirmation.
Figure 10:
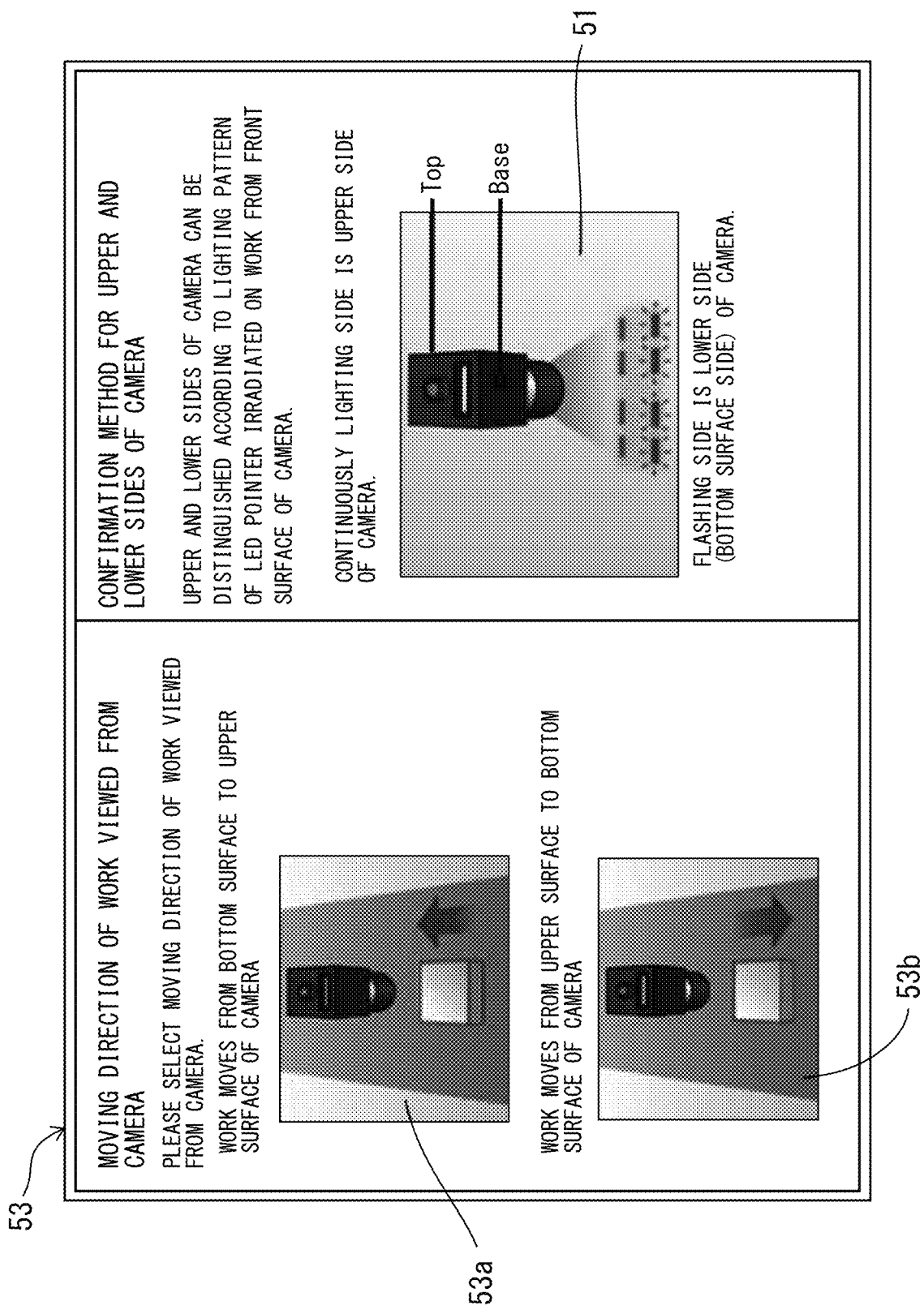
FIG. 10 is a diagram showing an interface for work moving direction selection.
Figure 11:
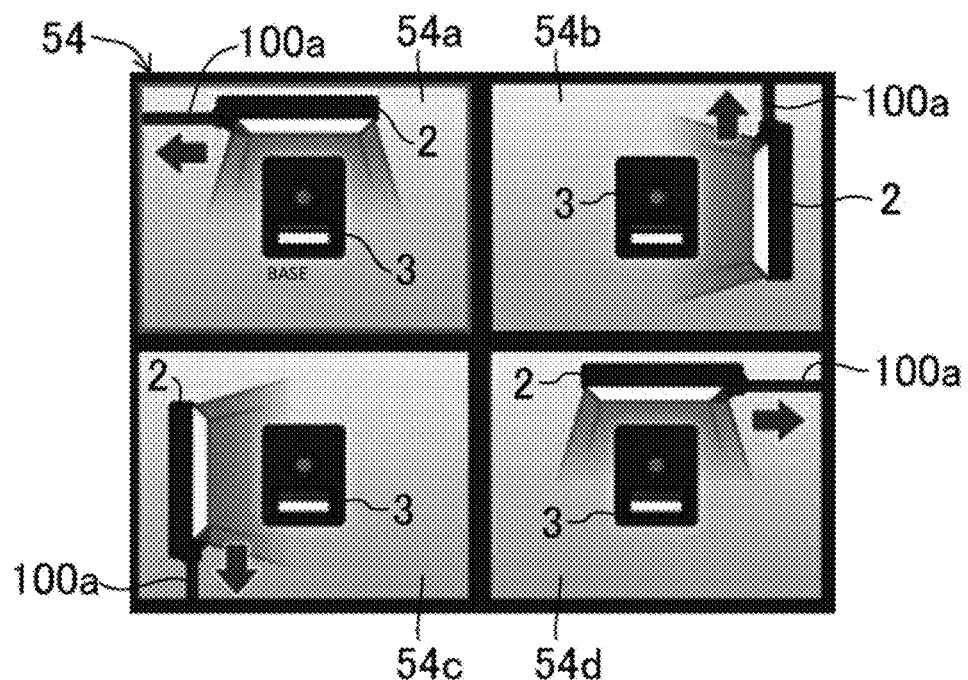
FIG. 11 is a diagram showing an interface for illumination direction selection.

Examples of the interfaces generated by the UI generating section 43 include an interface for illumination setting method selection 50 shown in FIG. 7, an interface for camera up-down confirmation 51 shown in FIG. 8, an interface for camera posture confirmation 52 shown in FIG. 9, an interface for work moving direction selection 53 shown in FIG. 10, and an interface for illumination direction selection 54 shown in FIG. 11. The interfaces 50 to 54 are displayed on the display section 5 during setting of the image inspection apparatus 1 performed before the image inspection apparatus 1 is operated.

The interface for illumination setting method selection 50 shown in FIG. 7 is an interface for inputting positional relation information between the light receiving elements 3a of the line camera 31 and the pattern light illuminating section 2. The interface for illumination setting method selection 50 is configured to be capable of inputting which of the positional relation of the reflected light reception and the positional relation of the transmitted light reception the positional relation between the light receiving elements 3a and the pattern light illuminating section 2 is. Displayed on the interface for illumination setting method selection 50 are a reflected light setting illustration 50a for schematically showing the positional relation of the reflected light reception and a transmitted light setting illustration 50b for schematically showing the positional relation of the transmitted light reception. The user only has to view the reflected light setting illustration 50a and the transmitted light setting illustration 50b displayed on the display section 5 and select, with the mouse 7 or the like, an illustration showing the same positional relation as a positional relation between the light receiving elements 3a and the pattern light illuminating section 2 set in an actual site. Therefore, an input error less easily occurs. Input content of the input operation of the user is received by the input information receiving section 44. Consequently, it is possible to easily perform input without erring in positional relation information.

The interface for camera up-down confirmation 51 shown in FIG. 8 is an interface for confirming the up-down direction of the line camera 31. When pointer light is irradiated from the LED pointer 34 of the imaging section 3, the illustration 50a including the pointer light is displayed such that the user can see that a flashing side is the lower side of the line camera 31. It is indicated by a sentence which side is the lower side of the line camera 31.

The interface for camera posture confirmation 52 shown in FIG. 9 is also an interface for confirming the up-down direction of the line camera 31. A posture display region 52a for schematically displaying a present posture of the imaging section 3 obtained by the gravitational acceleration sensor 35 of the imaging section 3 is incorporated in the interface for camera posture confirmation 52. Displayed in the posture display region 52a are a rear view 52b indicating a tilt with respect to the horizontal plane at the time when the imaging section 3 is viewed from the rear, a side view 52c indicating a tilt with respect to the vertical plane at the time when the imaging section 3 is viewed from the side, and a top view 52d showing a posture at the time when the imaging section 3 is viewed from the top. The user can confirm the up-down direction of the line camera 31 by viewing the FIGS. 52b, 52c, and 52d displayed in the posture display region 52a.

The interface for work moving direction selection 53 shown in FIG. 10 is an interface for selecting and inputting a moving direction of the work W. The interface for camera up-down confirmation 51 shown in FIG. 8 can be incorporated in the interface for work moving direction selection 53. Displayed on the interface for work moving direction selection 53 are an upward direction movement illustration 53a showing a state in which the work W moves from the lower side (the bottom surface side) toward the upper side of the line camera 31 and a downward direction movement illustration 53b showing a state in which the work W moves from the upper side to the lower side of the line camera 31. The user can grasp the up-down direction of the line camera 31 viewing the interface for camera up-down confirmation 51 displayed on the display section 5. Then, the user can select and input a moving direction with respect to the line camera 31 of the work W viewing the upward direction movement illustration 53a and the downward direction movement illustration 53b.

The interface for illumination direction selection 54 shown in FIG. 11 is an interface for selecting and inputting a positional relation between the line camera 31 and the pattern light illuminating section 2. The interface for illumination direction selection 54 can be displayed on the premise that the user knows the direction of the line camera 31 (the upper side or the lower side). The interface for illumination direction selection 54 is configured such that a direction of the pattern light illuminating section 2 with respect to the line camera 31 can be selected out of a plurality of illustrations.

That is, displayed on the interface for illumination direction selection 54 are a first illustration 54a showing a state in which the pattern light illuminating section 2 is disposed such that the signal line 100a extends to the left side with respect to the line camera 31, a second illustration 54b showing a state in which the pattern light illuminating section 2 is disposed such that the signal line 100*a* extends to the upper side with respect to the line camera 31, a third illustration 54*c* showing a state in which the pattern light illuminating section 2 is disposed such that the signal line 100*a* extends to the lower side with respect to the line camera 31, and a fourth illustration 54*d* showing a state in which the pattern light illuminating section 2 is disposed such that the signal line 100*a* extends to the right side with respect to the line camera 31. The user can select and input a positional relation between the line camera 31 and the pattern light illuminating section 2 set in the actual site viewing the first to fourth illustrations 54*a* to 54*d* displayed on the display section 5.

Figure 12:
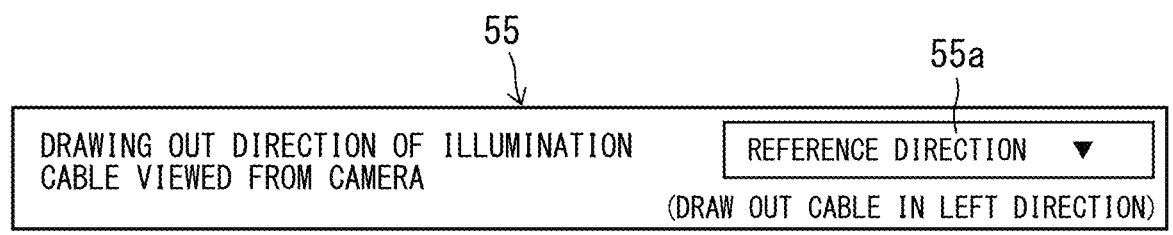
FIG. 12 is a diagram showing an interface for cable draw-out direction selection.

The interfaces generated by the UI generating section 43 can include an interface for cable draw-out direction selection 55 shown in FIG. 12. A "cable" means the signal line 100*a* connected to the pattern light illuminating section 2. The interface for cable draw-out direction selection 55 can be configured as a form including a so-called pulldown menu. The interface for cable draw-out direction selection 55 can be displayed on the premise that the user knows the direction of the line camera 31 (the upper side or the lower side). The interface for cable draw-out direction selection 55 is configured such that a direction of the pattern light illuminating section 2 with respect to the line camera 31 can be selected out of a plurality of choices.

That is, a pulldown menu 55*a* of the interface for cable draw-out direction selection 55 includes four choices, that is, a "reference direction", "90° clockwise", "180° clockwise", and "270° clockwise" (in FIG. 12, only the "reference direction" is displayed). The "reference direction" is a choice selected when the pattern light illuminating section 2 is disposed such that the signal line 100*a* extends in the direction (the left direction) indicated by the first illustration 54*a* of the interface for illumination direction selection 54 shown in FIG. 11. The "90° clockwise" is a choice selected when the pattern light illuminating section 2 is disposed such that the signal line 100*a* extends in the upward direction. The "180° clockwise" is a choice selected when the pattern light illuminating section 2 is disposed such that the signal line 100*a* extends in the right direction. The "270° clockwise" is a choice selected when the pattern light illuminating section 2 is disposed such that the signal line 100*a* extends in the downward direction. The representations of the choices are examples and are not limited to the representations described above.

Configuration of the Image Analyzing Section 45

The image analyzing section 45 shown in FIG. 2 is a section for analyzing a plurality of images captured by the imaging section 3 to thereby acquire positional relation information concerning a positional relation between the light receiving elements 3*a* of the line camera 31 and the pattern light illuminating section 2. The image analyzing section 45 can be a part of the information acquiring section 9.

Specifically, during the setting of the image inspection apparatus 1 performed before the image inspection apparatus 1 is operated, as a first step, the image analyzing section 45 controls the pattern light illuminating section 2 and the imaging section 3 to generate a first image obtained by imaging an irradiation surface on which first pattern light having a periodic illuminance distribution in one direction is irradiated and a second image obtained by imaging an irradiation surface on which second pattern light having a periodic illuminance distribution in a direction orthogonal to the one direction is irradiated. The irradiation surfaces may be the work W or may be other members.

Figure 13:
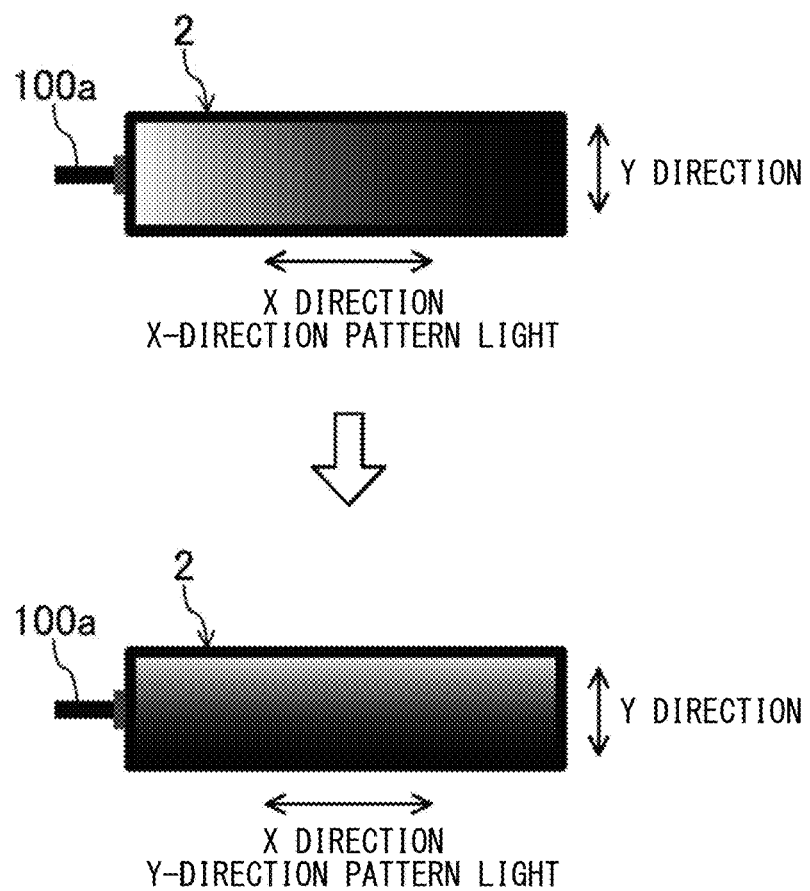
FIG. 13 is a diagram showing first pattern light and second pattern light irradiated when positional relation information between light receiving elements and the pattern light illuminating section is acquired.

The first pattern light in the first step can be X-direction pattern light, the illuminance of which changes in the X direction as shown on the left side of FIG. 13. The first pattern light is set as pattern light that becomes darker toward the right side of FIG. 13. The second pattern light can be Y-direction pattern light, the illuminance of which changes in the Y-direction as shown on the right side of FIG. 13. The second pattern light is set as pattern light that becomes darker toward the lower side of FIG. 13.

Figure 14:
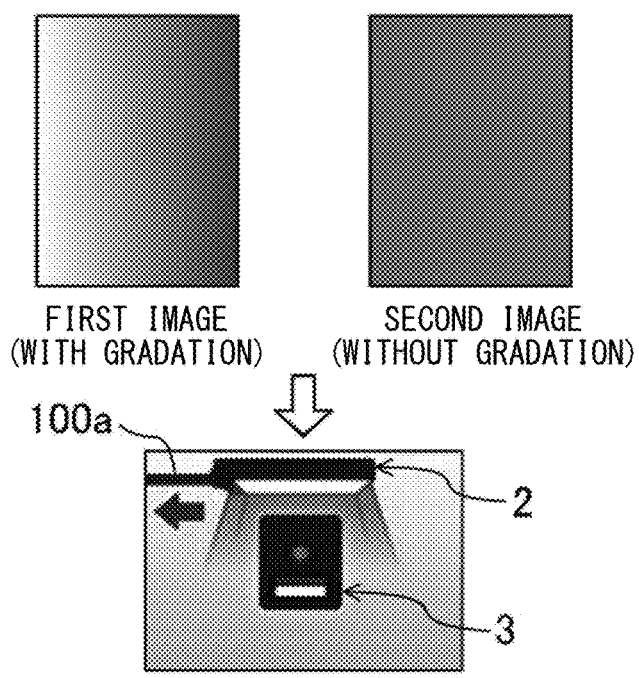
FIG. 14 is a diagram showing a first image and a second image obtained when the pattern light illuminating section is disposed such that a signal line extends in the left direction.

First, the X-direction pattern light on the left side of FIG. 13 is irradiated on any irradiation surface. The irradiation surface, on which the X-direction pattern light is irradiated, is imaged by the imaging section 3 to obtain a first image. It is assumed that the first image is an image with gradation that becomes darker toward the right side as shown in FIG. 14. Thereafter, the Y-direction pattern light on the right side of FIG. 13 is irradiated on any irradiation surface. The irradiation surface, on which the Y-direction pattern light is irradiated, is imaged by the imaging section 3 to obtain a second image. It is assumed that the second image is an image without gradation as shown in FIG. 14. Since the array direction of the light receiving elements 3*a* is the X direction, when the first image and the second image shown in FIG. 14 are obtained, it can be estimated that the pattern light illuminating section 2 is disposed such that the signal line 100*a* extends in the left direction as shown on the lower side of FIG. 14. Note that this relation only has to be defined beforehand.

Figure 15:
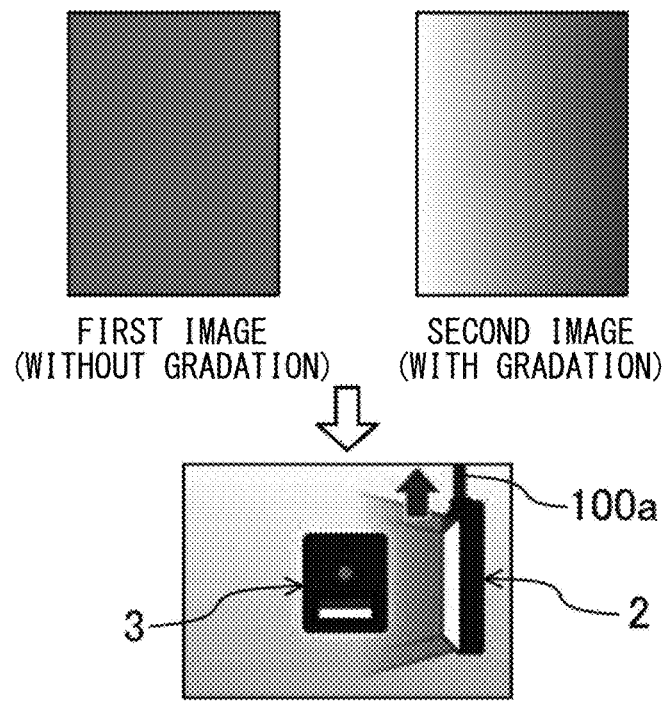
FIG. 15 is a diagram showing a first image and a second image obtained when the pattern light illuminating section is disposed such that the signal line extends in the upward direction.

When the first image is an image without gradation and the second image is an image with gradation that becomes darker toward the right side as shown in FIG. 15, it can be estimated that the pattern light illuminating section 2 is disposed such that the signal line 100*a* extends in the upward direction as shown on the lower side of FIG. 15.

Figure 16:
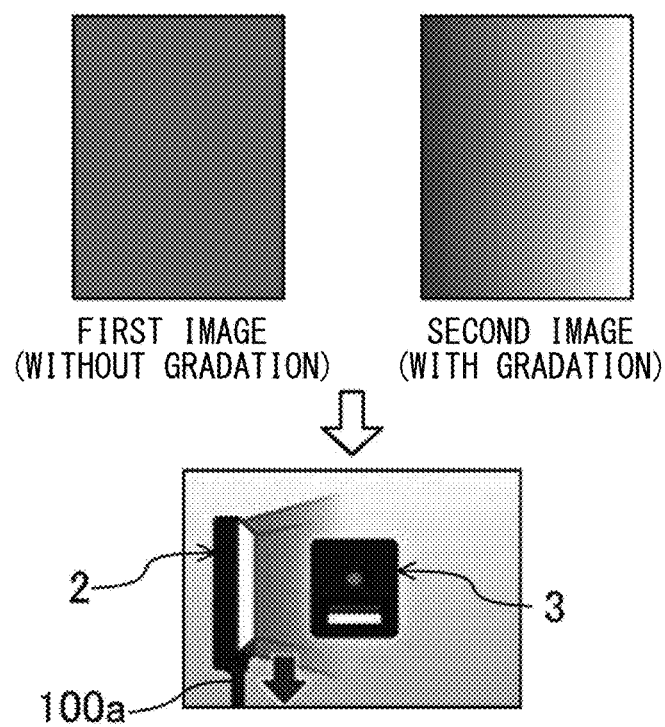
FIG. 16 is a diagram showing a first image and a second image obtained when the pattern light illuminating section is disposed such that the signal line extends in the downward direction.

When the first image is an image without gradation and the second image is an image with gradation that becomes darker toward the left side as shown in FIG. 16, it can be estimated that the pattern light illuminating section 2 is disposed such that the signal line 100*a* extends in the downward direction as shown on the lower side of FIG. 16.

Figure 17:
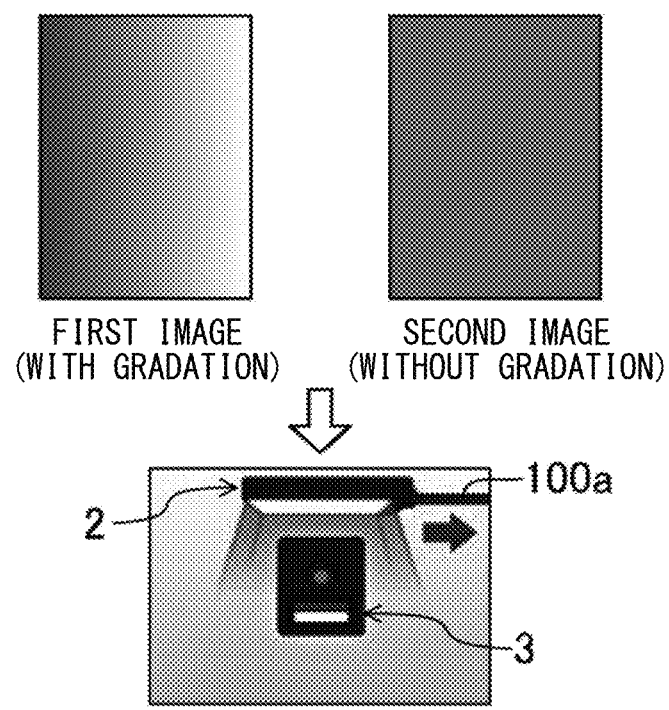
FIG. 17 is a block diagram showing a first image and a second image obtained the pattern light illuminating section is disposed such that the signal line extends in the right direction.

When the first image is an image with gradation that becomes darker toward the left side and the second image is an image without gradation as shown in FIG. 17, it can be estimated that the pattern light illuminating section 2 is disposed such that the signal line 100*a* extends in the right direction as shown in the lower side of FIG. 17.

That is, the image analyzing section 45 executes a step of analyzing the first image and the second image captured by the imaging section 3. As a result, the image analyzing section 45 can acquire positional relation information between the light receiving elements 3*a* and the pattern light illuminating section 2 by obtaining whether the first image and the second image are images with gradation or images without gradation and, when the first image and the second image are the images with gradation, obtaining toward which side the images become dark (or bright).

An area camera (a camera in which light receiving elements are disposed to be arranged in the X direction and the Y direction) can be used in the imaging section 3 rather than the line camera 31. In the case of the area camera, the image analyzing section 45 can acquire positional relation information between the area camera and the pattern light illuminating section 2 by analyzing one image captured by the imaging section 3.

Figure 18:
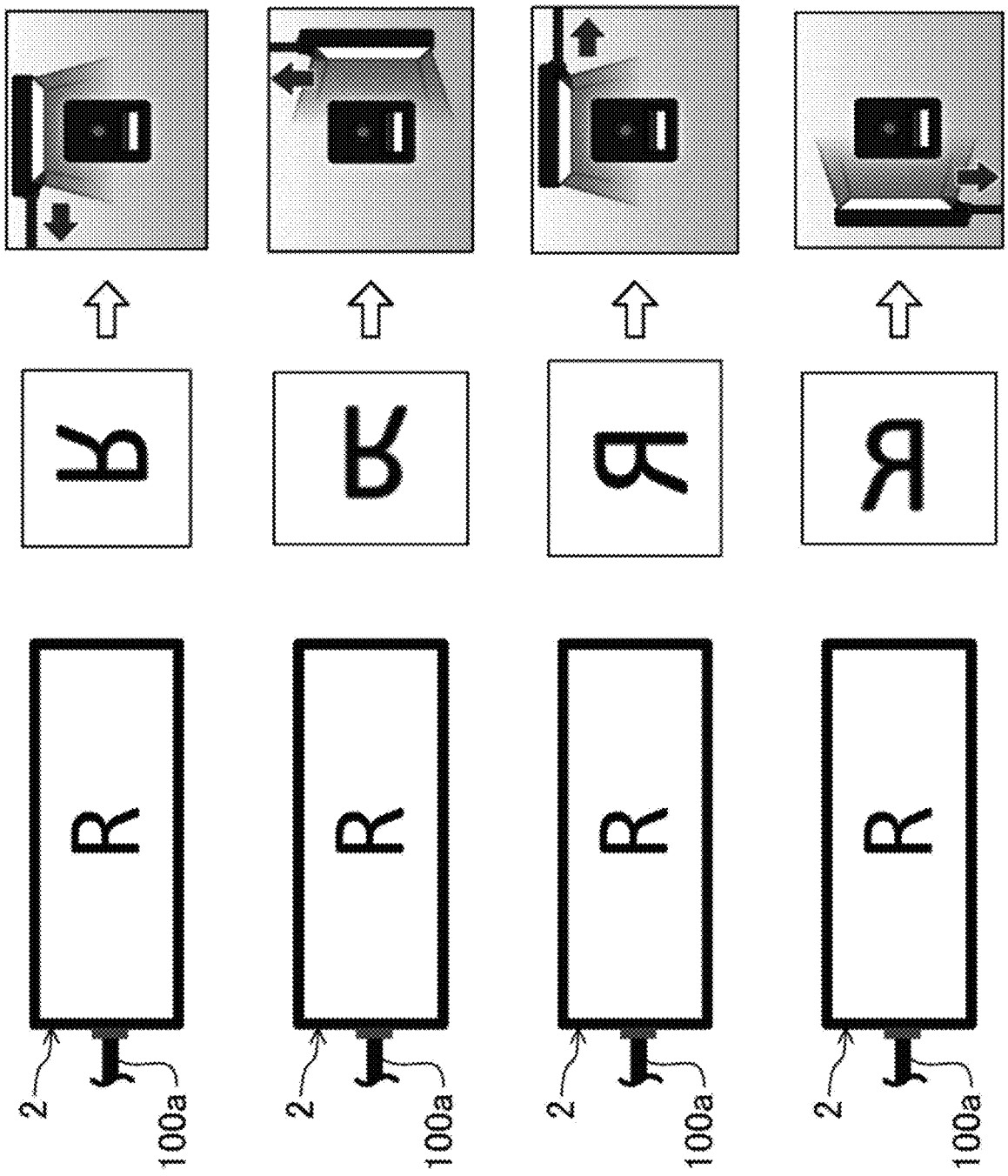
FIG. 18 is a diagram for explaining the point for acquiring positional relation information between the light receiving elements and the pattern light illuminating section set when an area camera is used.

Specifically, as shown in FIG. 18, pattern light capable of displaying "R" of alphabet is irradiated on any irradiation surface from the pattern light illuminating section 2. The irradiation surface, on which the pattern light is irradiated, is imaged by the imaging section 3. As a result, when an image of "R" shown at the top of FIG. 18 is obtained, it can be estimated that the pattern light illuminating section 2 is disposed such that the signal line 100a extends in the left direction. When an image of "R" shown second from the top of FIG. 18 is obtained, it can be estimated that the pattern light illuminating section 2 is disposed such that the signal line 100a extends in the upward direction. When an image of "R" shown third from the top of FIG. 18 is obtained, it can be estimated that the pattern light illuminating section 2 is disposed such that the signal line 100a extends in the right direction. When an image of "R" shown in the bottom of FIG. 18 is obtained, it can be estimated that the pattern light illuminating section 2 is disposed such that the signal line 100a extends in the downward direction. The pattern light may indicate something other than "R". The pattern light may indicate, for example, a character, a sign, a figure, or a combination of the character, the sign, and the figure.

Other Forms of the Image Acquiring Section

Figure 19:
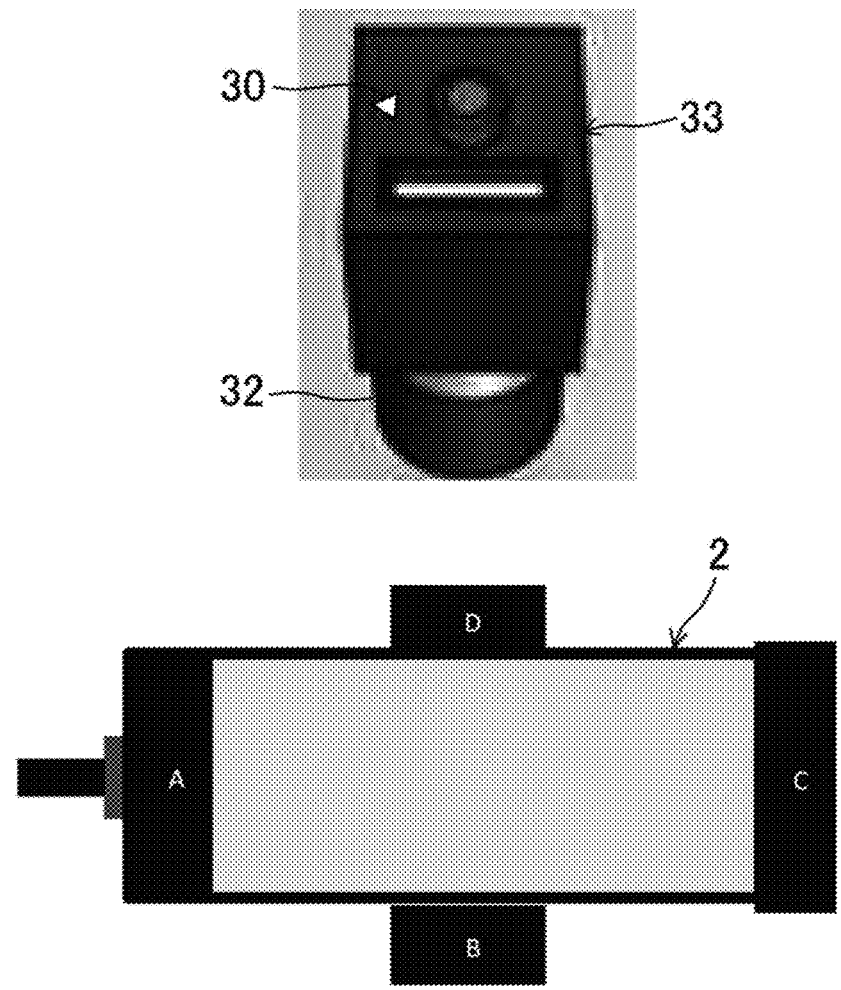
FIG. 19 is a diagram showing an imaging section and a pattern light illuminating section related to another form of an information acquiring section.

As shown in FIG. 19, a predetermined mark 3c is provided in the imaging section 3. A left side sign A, a lower side sign B, a right side sign C, and an upper side sign D respectively indicating four directions are provided in the light illuminating section 2. The UI generating section 43 generates an interface for direction selection 56 shown in FIG. 20. The generated interface for direction selection 56 is displayed on the display section 5. A pulldown menu 56a, with which the left side sign A, the lower side sign B, the right side sign C, and the upper side sign D can be selected, is provided in the interface for direction selection 56.

The user visually confirms on which side of the pattern light illuminating section 2 the mark 3c of the imaging section 3 is located. Thereafter, the user selects, with the pulldown menu 56a of the interface for direction selection 56, the signs A to D present in a direction pointed by the mark 3c of the imaging section 3. Consequently, the user can input positional relation information between the light receiving elements 3a of the line camera 31 and the pattern light illuminating section 2.

Attention Attracting Function

Figure 20:
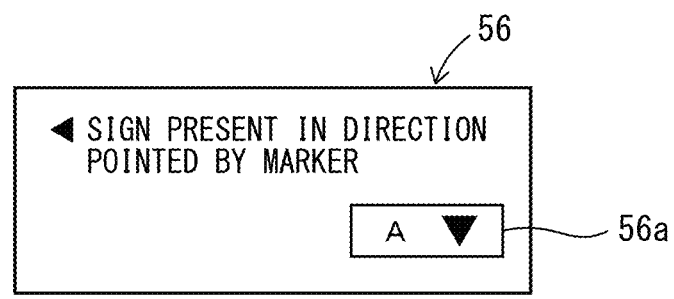
FIG. 20 is a diagram showing an interface for direction selection.

By using the interface for illumination direction selection 54 shown in FIG. 11, the interface for cable draw-out direction selection 55 shown in FIG. 12, and the interface of direction selection shown in FIG. 20, the user can input positional relation information between the light receiving elements 3a and the pattern light illuminating section 2. However, the user sometimes errs in input operation or, in the first place, misrecognizes the up-down direction of the line camera 31. It is conceivable that an input result of the user is different from an actual setting situation.

In this respect, an attention attracting function can be provided in the image inspection apparatus 1. The attention attracting function is a function of, after the user inputs positional relation information between the light receiving elements 3a and the pattern light illuminating section 2 making use of the interface for illumination direction selection 54 shown in FIG. 11, the interface for cable draw-out direction selection 55 shown in FIG. 12, and the interface for direction selection 56 shown in FIG. 20, performing the analysis shown in FIGS. 13 to 17 or performing the analysis shown in FIG. 18 in the case of the area camera to determine whether the input positional relation information coincides with an actual setting situation, and, as a result of the determination, when the input positional relation information does not coincide with the actual setting situation, displaying, for example, a message on the display section 5 to urge the user to perform confirmation and input again.

Configuration of the Control Section 41

The control section 41 shown in FIG. 2 is an imaging control section for performing control of the pattern light illuminating section 2 and the imaging section 3. Specifically, the control section 41 controls the pattern light illuminating section 2 and the imaging section 3 to generate a plurality of pattern lights, phases of illuminance distributions of which are shifted to at least one direction of the array direction of the light receiving elements 3a and the moving direction of the work W, sequentially irradiate the plurality of pattern lights on the work W, image regions including at least irradiation surfaces of the pattern lights in the work W at timings when the pattern lights are irradiated, and obtain a plurality of luminance images. When obtaining the plurality of luminance images, the control section 41 may change both of illumination conditions of the pattern light illuminating section 2 and imaging conditions of the imaging section 3 or may change only one of the illumination conditions and the imaging conditions.

The illumination conditions of the pattern light illuminating section 2 can include, for example, types of pattern lights to be generated, order of generation of a plurality of pattern images to be generated, and brightness of pattern light (intensity of light). The types of pattern lights to be generated can include, for example, the four Y-direction pattern lights shown in FIG. 5A and the four X-direction pattern lights shown in FIG. 5B. Besides, the types of pattern lights to be generated can include pattern lights having different wavelengths. The order of generation of pattern lights can be the order of the Y-direction pattern light in the case of 0°, the Y-direction pattern light in the case of 90°, the Y-direction pattern light in the case of 180°, and the Y-direction pattern light in the case of 270° shown in FIG. 5A and thereafter the X-direction pattern light in the case of 0°, the X-direction pattern light in the case of 90°, the X-direction pattern light in the case of 180°, and the X-direction pattern light in the case of 270° shown in FIG. 5B.

The illumination conditions of the pattern light illuminating section 2 can be stored in an illumination condition storing section 10a provided in the storage device 10. An arithmetic device (a field programmable gate array: FPGA) 2a including an illumination condition storing section 2b capable of storing the illumination conditions of the pattern light illuminating section 2 can be incorporated in the pattern light illuminating section 2. The arithmetic device is not limited to the FPGA. An arithmetic section other than the FPGA and the illumination condition storing section 2b can be incorporated.

The imaging conditions of the imaging section 3 include, for example, at least one of a gain and an exposure time (shutter speed) during imaging. The control section 41 can optionally change the gain and the exposure time of the imaging section 3. The imaging section 3 executes the imaging with the gain and the exposure time set by the control section 41.

Transmission of a Trigger Signal

The control section 41 is configured to be capable of receiving an encoder pulse signal when the encoder pulse signal is input from the outside. The encoder pulse signal is a pulse signal generated outside the control section 41 such as a pulse signal output from a rotary encoder provided in a rotating shaft of the belt conveyor for conveyance B or a pulse signal output from the external control device 8.

The control unit 4 includes a trigger signal transmitting section 4b. The trigger signal transmitting section 4b may configure a part of the control section 41 or may be configured separately from the control section 41. The trigger signal transmitting section 4b is configured to, when the control section 41 receives one encoder pulse signal from the outside, sequentially transmit a plurality of imaging trigger signals to the imaging section 3 and transmit a plurality of illumination trigger signals to the pattern light illuminating section 2 such that a plurality of illuminance images are generated with at least one of the illumination conditions of the pattern light illuminating section 2 and the imaging conditions of the imaging section 3 changed. The trigger signal transmitting section 4b can be configured to transmit a plurality of illumination trigger signals to only the imaging section 3.

Figure 35:
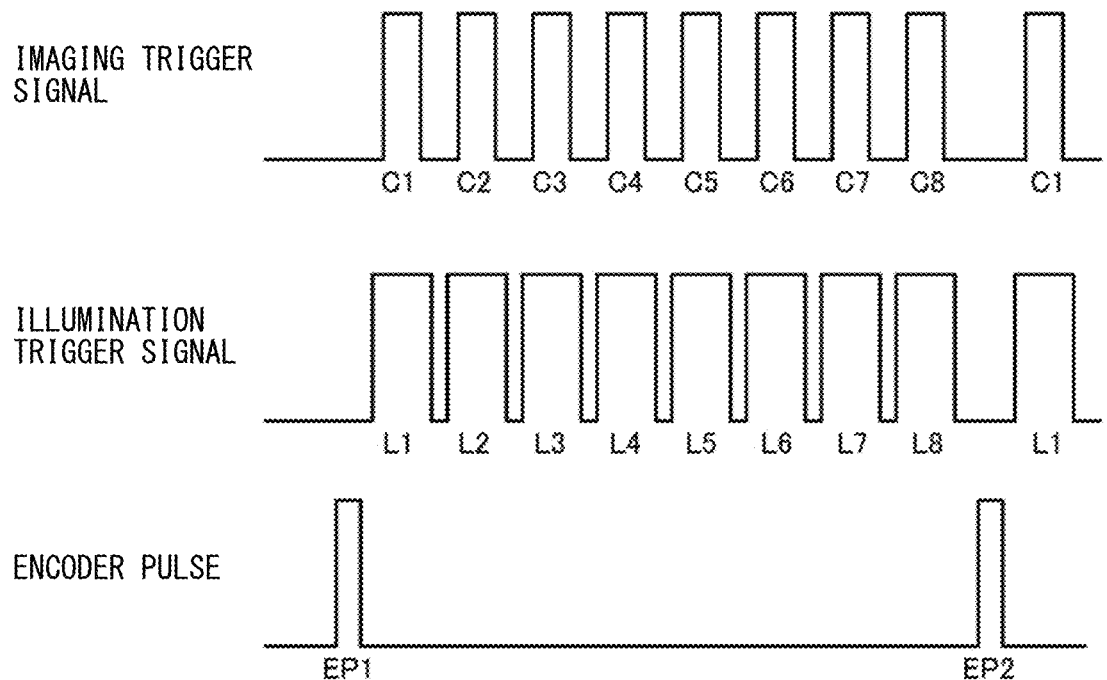
FIG. 35 is a time chart showing a relation between an imaging trigger signal and an illumination trigger signal and an encoder pulse.

In this embodiment, as explained above, the pattern light illuminating section 2 irradiates the eight kinds of pattern lights. Therefore, as shown in FIG. 35, when receiving one encoder pulse signal EP1 from the outside, the trigger signal transmitting section 4b transmits an imaging trigger signal eight times (C1 to C8). Thereafter, when receiving an encoder pulse signal EP2, the trigger signal transmitting section 4b transmits the imaging trigger signal eight times in the same manner.

The trigger signal transmitting section 4b is configured to, when receiving one encoder pulse signal from the outside, sequentially transmit a plurality of illumination trigger signals to the pattern light illuminating section 2 in synchronization with the imaging trigger signals. The pattern light illuminating section 2 needs to sequentially irradiate the eight kinds of pattern lights. Therefore, when receiving one encoder pulse signal EP1 from the outside, the trigger signal transmitting section 4b transmits an illumination trigger signal eight times (L1 to L8). Thereafter, when receiving the encoder pulse signal EP2, the trigger signal transmitting section 4b transmits the illumination trigger signal eight times in the same manner.

The control section 41 can also be configured to, when receiving one encoder pulse signal from the outside, sequentially transmit a plurality of imaging trigger signals to the imaging section 3 in synchronization with the illumination trigger signals.

Generation of Pattern Light by the Pattern Light Illuminating Section

The pattern light illuminating section 2 controls, on the basis of the illumination trigger signal transmitted from the trigger signal transmitting section 4b, values of electric currents fed to the light emitting diodes 20 and 21 to thereby generate a plurality of pattern lights. Since the pattern light has a periodic illuminance distribution, the values of the electric currents fed to the light emitting diodes 20 and 21 are respectively set according to pattern light to be generated. The values of the electric currents fed to the light emitting diodes 20 and 21 are equivalent to the illumination conditions. The current values can be stored in the illumination condition storing section 10a of the storage device 10.

The illumination conditions can be illumination setting data including illumination timing information (a lighting time and a lighting interval), illumination intensity information, and illumination pattern information of the light emitting diodes 20 and 21 of the pattern light illuminating section 2. All the illumination setting data can cause the display section 5 to display a user interface for illumination setting and can receive adjustment by the user.

The lighting timing information includes a lighting time in which the light emitting diodes 20 and 21 are kept lit after the illumination trigger signal is received and a lighting interval until the next light emitting diodes 20 and 21 are lit after the light emitting diodes 20 and 21 lit earlier are extinguished when the light emitting diodes 20 and 21 to be lit, are switched. The illumination intensity information is information indicating illumination intensity (brightness) of the light emitting diodes 20 and 21. Specifically, a current value can be exemplified. The illumination pattern information is information for specifying a sine wave-like pattern and includes, for example, a period and a phase shift amount (a degree of a shift in one phase shift). The illumination pattern does not have to be the sine wave and may be, for example, a rectangular wave.

The illumination setting data can be stored in the illumination condition storing section 10a by input means such as the keyboard 6 and the mouse 7.

The illumination condition storing section 10a may be provided in the pattern light illuminating section 2, may be provided in the imaging section 3, or may be provided in any component of the image inspection apparatus 1.

The control section 41 can once read the illumination conditions stored in the illumination condition storing section 10a of the storage device 10, output the illumination conditions stored in the illumination condition storing section 10a to the arithmetic device 2a of the pattern light illuminating section 2, and cause the illumination condition storing section 2b included in the arithmetic device 2a to store the illumination conditions. Consequently, when receiving an illumination trigger signal from the outside, the pattern light illuminating section 2 can illuminate the work W according to the illumination conditions stored in the illumination condition storing section 2b. Therefore, it is possible to increase generation speed of pattern light of the pattern light illuminating section 2 compared with when the illumination conditions are read from the illumination condition storing section 10a of the storage device 10.

Figure 36:
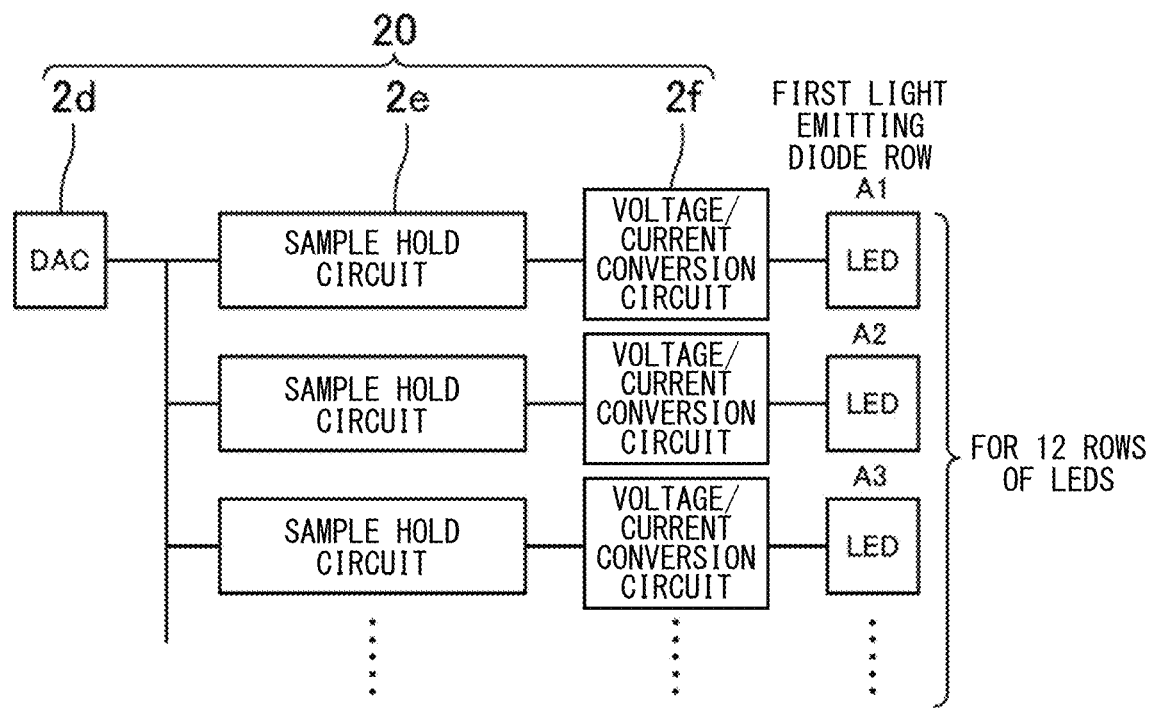
FIG. 36 is a diagram showing a part of a circuit configuration of a current control section of a pattern light illuminating section.

As shown in FIG. 36, a current control section 2c, which controls values of electric currents fed to the light emitting diodes 20 and 21, is incorporated in the pattern light illuminating section 2. The current control section 2c is configured to be capable of receiving an illumination trigger signal. When receiving the illumination trigger signal, the current control section 2c controls, according to the illumination conditions stored in the illumination condition storing section 2b, the values of the electric currents fed to the light emitting diodes 20 and 21.

The current control section 2c, which controls the first light emitting diode rows A1 to A12, and the current control section 2c, which controls the second light emitting diode rows B1 to B12, are provided. Both the current control sections 2c have the same configuration. The current control section 2c shown in FIG. 36 controls the first light emitting diode row A1. The current control section 2c includes one D/A converter 2d, a plurality of sample hold circuits 2e, and a plurality of voltage/current conversion circuits 2f. The sample hold circuits 2e and the voltage/current conversion circuits 2f are provided by the same number as the number (twelve) of the light emitting diodes 20 configuring the first light emitting diode row A1. The twelve sample hold circuits 2e are connected to the D/A converter 2d. The voltage/current conversion circuits 2f are connected to output sides of the sample hold circuits 2e. The light emitting diodes 20 are connected to output sides of the voltage/current conversion circuits 2f.

Figure 37:
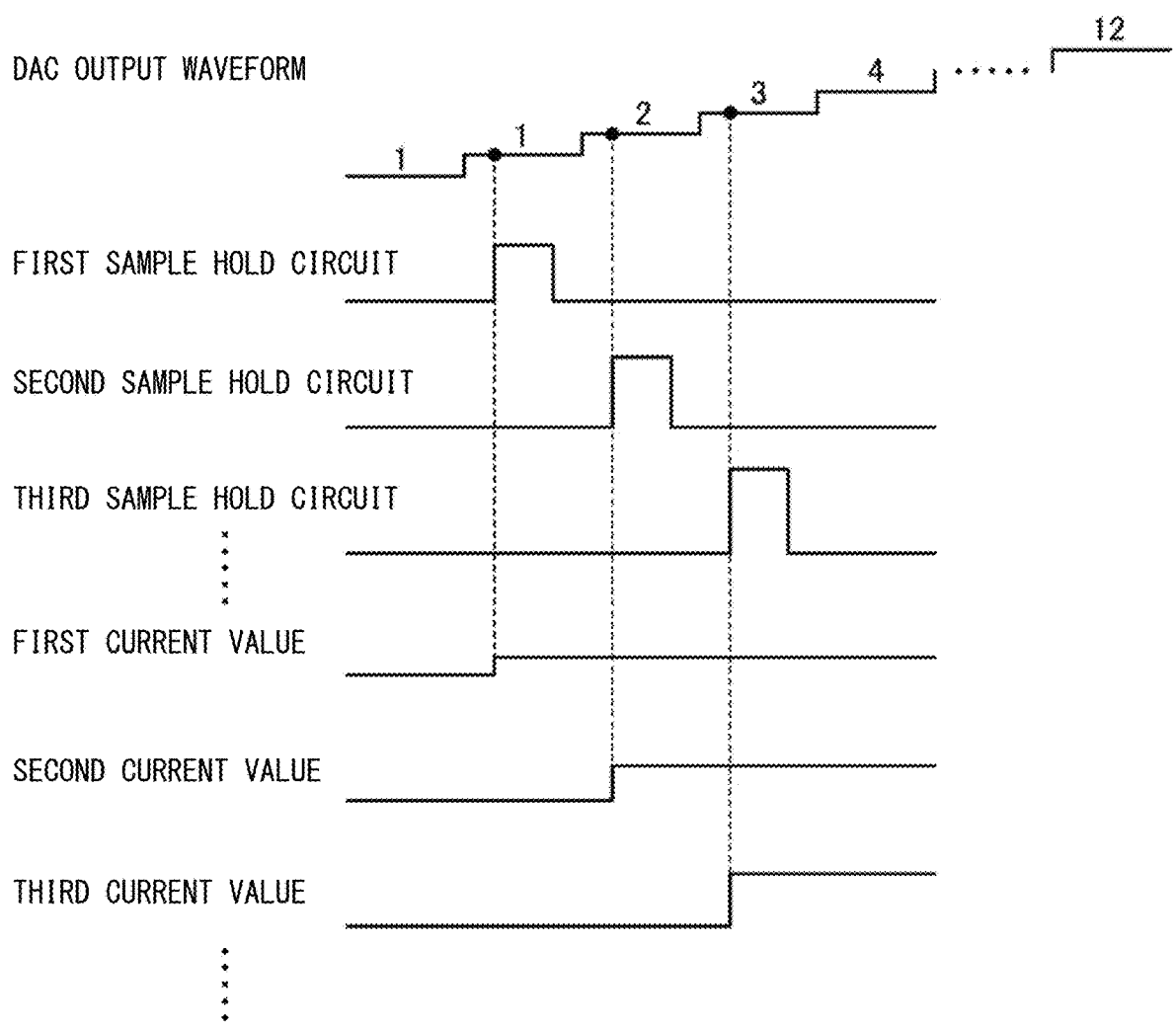
FIG. 37 is a diagram for explaining a current value control method by a current control section.

When a pattern is switched, the D/A converter 2d is configured to sequentially output control voltages for A1 to A12 as shown in FIG. 37. The twelve sample hold circuits 2e respectively sample, on the basis of a sampling signal input from the outside, at predetermined sample timings, voltages of waveform signals output from the D/A converter 2d. After a first sample hold circuit shown in FIG. 37 samples a voltage, a second sample hold circuit samples a voltage. In this way, the voltages are sequentially sampled.

A voltage value sampled by the first sample hold circuit is converted into a current value corresponding to the voltage value by the voltage/current conversion circuits 2f. An electric current having the current value flows to the light emitting diode A1. In this example, the voltage value sampled by the first sample hold circuit is the smallest. Sampled voltage values are larger in the order of the second and third sample hold circuits. That is, a first current value is the smallest and second and third current values are larger in this order. Therefore, brightness of the light emitting diodes A1 to A12 changes according to the current values. Consequently, pattern light having a periodic illuminance distribution is generated. A waveform signal output from the D/A converter 2d is changed, whereby the illuminance distribution of the pattern light changes. It is possible to represent the illuminance distribution of the pattern light with a waveform approximate to the sine wave, with a waveform approximate to a triangular wave, or with a waveform approximate to a rectangular wave. By setting a current value to make brightness the same in all the light emitting diodes 20, it is possible to obtain illumination having uniform illuminance over an entire surface.

In this embodiment, an output voltage of the D/A converter 2d is set as a control voltage of the light emitting diodes 20. The sample hold circuits 2e for the light emitting diodes 20 specify timings and perform sampling. Therefore, it is possible to control light amounts of the plurality of light emitting diodes 20 with one D/A converter 2d. Consequently, it is possible to reduce the number of the high-speed and high-gradation D/A converters 2d generally having large size and generate pattern lights with the sample hold circuits 2e having small size. Therefore, it is possible to reduce a substrate area and reduce cost.

The light emitting diodes 21 of the respective second light emitting diode rows B1 to B12 are arranged in the Y direction. Therefore, it is possible to generate the X-direction pattern light according to current value control of the second light emitting diode rows B1 to B12. The light emitting diodes 20 of the respective first light emitting diode rows A1 to A12 are arranged in the X direction. Therefore, it is possible to generate the Y-direction pattern light according to current value control of the first light emitting diode rows A1 to A12.

The wavelength of the four Y-direction pattern lights shown in FIG. 5A and the wavelengths of the four X-direction pattern lights shown in FIG. 5B may be different. For example, red pattern lights are irradiated from the light emitting diodes 20 of the first light emitting diode rows A1 to A12 and blue pattern lights are irradiated from the light emitting diodes 21 of the second light emitting diode rows B1 to B12. Consequently, it is possible to change the wavelengths of the Y-direction pattern lights and the wavelengths of the X-direction pattern lights. In this case, if the Y-direction pattern lights and the X-direction pattern lights are simultaneously irradiated on the work W to image the work W with the imaging section 3 including a color camera, it is possible to simultaneously obtain raw images by the irradiation of the Y-direction pattern lights and raw images by the irradiation of the X-direction pattern lights. It is possible to reduce a time require for imaging.

Period of an Illuminance Distribution of Pattern Light

When an illuminance distribution of pattern light can be represented by a waveform approximate to a sine waveform, a period of the sine waveform can be set to, for example, 100 mm. By setting the period of the sine waveform to approximately 100 mm, even if the surface of the work W with less specular reflection (which is not a complete reflecting diffuser) is imaged, it is possible to perform stacking processing of shapes explained below. It is possible to expand a range of imaging on the work W. Attenuation due to an MTF of a lens of the light-condensing-system optical system 32 of the imaging section is reduced by setting the period of the sine wave to approximately 100 mm. However, when a coating surface or the like is inspected, it is sometimes desirable to reduce the period, the period is not limited to 100 mm. By reducing the period, it is possible to reduce the influence of a foundation when the coating surface is inspected. It is easy to detect a subtle difference of a surface gradient.

Generation of Images for Inspection by Deflectometry

In this embodiment, the imaging section 3 images the work W to obtain a plurality of luminance images at timings when the work W is illuminated by the pattern light illuminating section 2. A phase map calculated making use of the principle of phase measuring deflectometry (PMD: (hereinafter referred to as "deflectometry") is processed on the basis of the plurality of luminance images captured by the imaging section 3. A plurality of images for inspection, with which different types of defects can be detected, is generated. Inspection of the work W can be performed using the images for inspection. A process for obtaining the plurality of luminance images can be executed by the control section 41 outputting the illumination trigger signal and the imaging trigger signal and controlling the pattern light illuminating section 2 and the imaging section 3 as explained above. A process for generating the images for inspection can be performed by the image generating section 42 shown in FIG. 2.

The image generating section 42 generates, on the basis of the plurality of luminance images captured by the imaging section 3, at least an image for inspection showing a reflection state of the surface of the work W and an image for inspection showing the shape of the work W. Examples of the image for inspection showing the reflection state of the surface of the work W include a specular reflection component image and a diffuse reflection component image. Examples of the image for inspection showing the shape of the work W include a shape image, a depth contour image, and a glossy ratio image.

The generation of images for inspection is explained in detail below with reference to a flowchart of FIG. 21 and a schematic diagram of FIG. 22. In step SA1 of the flowchart, the control section 41 controls the pattern light illuminating section 2 and the imaging section 3 to obtain a plurality of luminance images (raw images). The luminance images obtained in step SA1 are intermediate images. The luminance images are once stored in the storage device 10 or the like. However, the luminance images are not displayed on the display section 5. The luminance images are images obtained by imaging the work W illuminated in different illumination forms (illumination by a plurality of pattern lights).

In step SA1, the control section 41 outputs an illumination trigger signal to the pattern light illuminating section 2. When receiving the illumination trigger signal, the pattern light illuminating section 2 generates pattern light according to the illumination conditions stored in the illumination condition storing section 2b and illuminates the work W. The illumination conditions at this time are illumination conditions for generating, in order, the Y-direction pattern light in the case of 0°, the Y-direction pattern light in the case of 90°, the Y-direction pattern light in the case of 180°, and the Y-direction pattern light in the case of 270° shown in FIG. 5A and the X-direction pattern light in the case of 0°, the X-direction pattern light in the case of 90°, the X-direction pattern light in the case of 180°, and the X-direction pattern light in the case of 270° shown in FIG. 5B. Therefore, the pattern light illuminating section 2 generates eight kinds of pattern lights in total (four kinds in the X direction and four kinds in the Y direction), phases of illuminance distributions of which are shifted in both the directions of the array direction of the light receiving elements 3a and the moving direction of the work W, and sequentially irradiates the pattern lights on the work W.

At the same time, the control section 41 outputs an imaging trigger signal to the imaging section 3. When receiving the imaging trigger signal, the imaging section 3 images the work W every time the pattern light is irradiated. When a screen size is set to 8K (8192 columns×1024 rows), the number of times of illumination necessary for obtaining one luminance image is 1024 times (the number of rows)× the number of times of illumination of pattern lights (eight times). The same number is the number of times of imaging.

In this embodiment, a plurality of imaging trigger signals (specifically, imaging trigger signals as many as the number of rows of pixels of one luminance image) are sequentially transmitted in order to obtain one luminance image. Therefore, it is possible to eliminate a shift of imaging timing every time the imaging trigger signal is received. The illumination trigger signal is transmitted to the pattern light illuminating section 2 in the same manner. Moreover, the illumination trigger signal and the imaging trigger signal are synchronized. Therefore, it is possible to eliminate a shift of illumination timing. Therefore, even if the number of times of illumination and the number of times of imaging increase when a plurality of luminance images are generated, it is possible to maintain a very small state of shifts of the imaging timing and the illumination timing.

During the imaging, since the number of times of irradiation of the pattern lights is eight, eight luminance images are obtained. As shown in FIG. 22, four luminance images (X) captured during the irradiation of the four kinds of X-direction pattern lights and four luminance images (Y) captured during the irradiation of the four kinds of Y-direction pattern lights are obtained.

Eight luminance images obtained by actually imaging the work W made of metal are shown in FIG. 23. Images on the left side of FIG. 23 are, in order from the top, luminance images obtained by respectively irradiating the X-direction pattern light in the case of 0°, the X-direction pattern light in the case of 90°, the X-direction pattern light in the case of 180°, and the X-direction pattern light in the case of 270°. Images on the right side of FIG. 23 are, in order from the top, luminance images obtained by respectively irradiating the Y-direction pattern light in the case of 0°, the Y-direction pattern light in the case of 90°, the Y-direction pattern light in the case of 180°, and the Y-direction pattern light in the case of 270°. Note that only the X-direction pattern lights or the Y-direction pattern lights may be irradiated.

Figure 21:
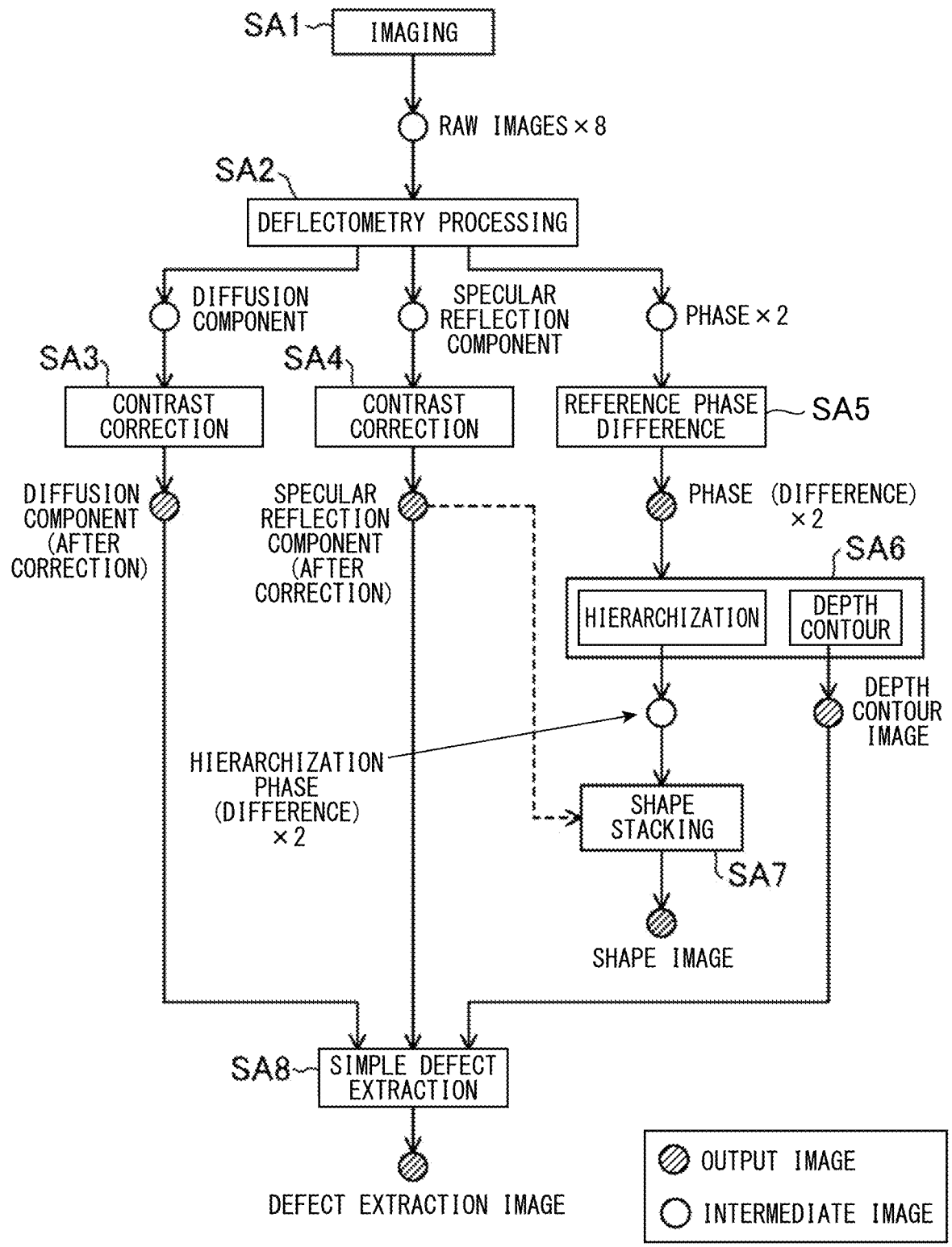
FIG. 21 is a flowchart showing a generation procedure for an image for inspection.
Figure 22:
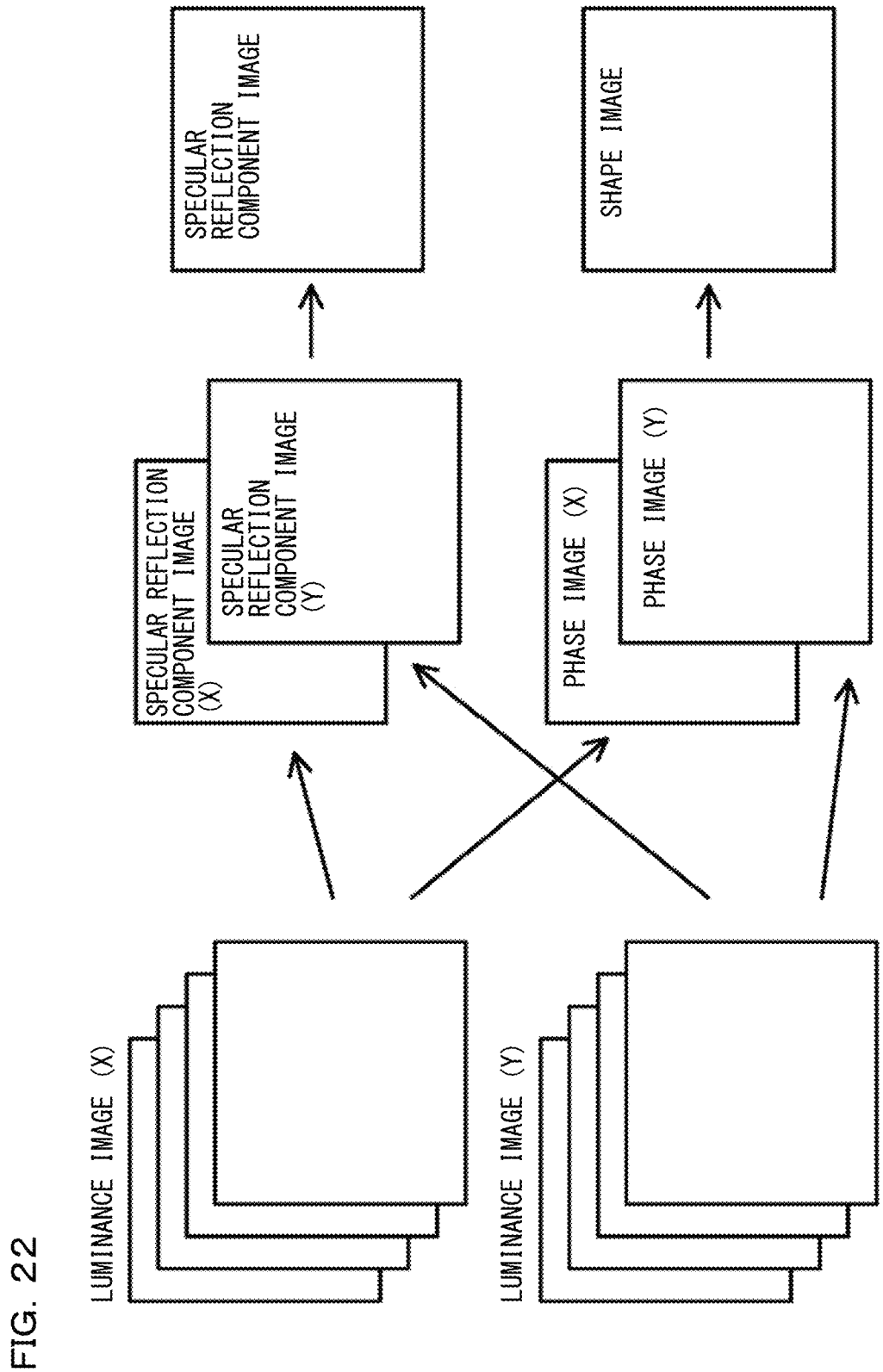
FIG. 22 is a diagram schematically showing a generation procedure for an image for inspection applied with the deflectometry principle.

Thereafter, the control section 41 proceeds to step SA2 of the flowchart of FIG. 21 and performs the deflectometry processing on the eight luminance images obtained in step SA1. The deflectometry processing can be performed in the image generating section 42. Specular reflection components and diffuse reflection components (+ environment components) are included in pixel values of the luminance images obtained by imaging the work W on which the pattern lights are irradiated. The phases of the illuminance distributions of the pattern lights are shifted by 90° ($\pi/2$) for each of the pattern lights in the X direction to perform imaging four times. Therefore, four kinds of the pixel values are obtained by the irradiation of the X-direction pattern lights. When a pixel value of a luminance image captured first is represented as $I_1$, a pixel value of a luminance image captured second is represented as $I_2$, a pixel value of a luminance image captured third is represented as $I_3$, and a pixel value of a luminance image captured fourth is represented as $I_4$, the pixel values $I_1$ to $I_4$ are given by the following Expression 1.

$$I_1 = R_d + R_s \sin(\varphi_s)$$
$$I_2 = R_d + R_s \sin\left(\varphi_s + \frac{\pi}{2}\right)$$
$$I_3 = R_d + R_s \sin(\varphi_s + \pi)$$
$$I_4 = R_d + R_s \sin\left(\varphi_s + \frac{3\pi}{2}\right)$$

Expression 1

In Expression 1, Rd represents a diffuse reflection component, Rs represents a specular reflection component, and $\varphi$s represents a specular reflection angle (phase). The diffuse reflection component, the specular reflection component, and the specular reflection angle are phase data. Phase data for one line can be obtained on the basis of a plurality of line images captured by the imaging section 3.

Similarly, since the phases of the illuminance distributions of the pattern lights are shifted by 90° ($\pi/2$) for each of the pattern lights in the Y direction to perform imaging four times, four kinds of pixel values are obtained by the irradiation of the Y-direction pattern lights. Concerning the Y direction, the pixel values $I_1$ to $I_4$ can also be represented by Expression 1 described above.

Specular Reflection Component Image

Figure 29:
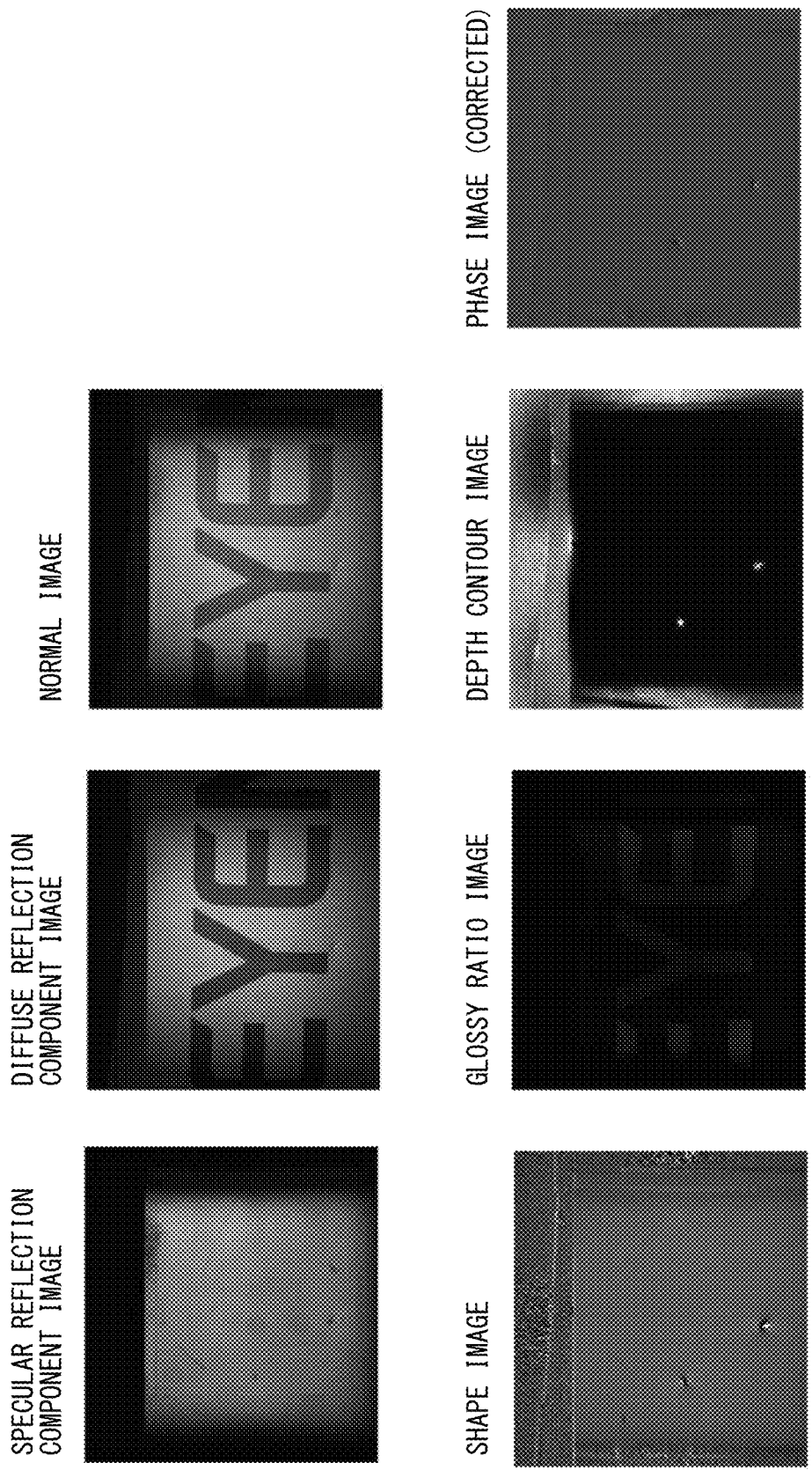
FIG. 29 is a diagram showing an example of an image for inspection.

A specular reflection component image is given by the following Expression 2. In Expression 2, a diffusion component is eliminated by a difference between reverse phases. As shown in FIG. 22, luminance images are respectively obtained in the X direction and the Y direction. A specular reflection component image is obtained by combining the luminance images. An example of the specular reflection component image is shown in FIG. 29. Note that a normal image shown in FIG. 29 is an image including a specular reflection component and a diffuse reflection component.

$$R_s = \frac{\sqrt{(I_3 - I_1)^2 + (I_4 - I_2)^2}}{2}$$

Expression 2

Specular Reflection Angle

A specular reflection angle is given by the following Expression 3. An angle is calculated as $\tan \theta = \sin \theta / \cos \theta$ by a $\pi/2$-shifted specular reflection component.

$$\varphi_s = \tan^{-1} \frac{I_2 - I_4}{I_3 - I_1} \qquad \text{Expression 3}$$

Average Image

An average image includes a diffusion component and an environment component. The average image is given by the following Expression 4. A specular reflection component is eliminated by addition of reverse phases.

$$\bar{I} = \frac{\sum_{i=1}^{4} I_i}{4} \qquad \text{Expression 4}$$

Diffuse Reflection Component Image

A diffuse reflection component image is given by the following Expression 5. An example of the diffuse reflection component image is shown in FIG. 29.

$$R_d = \bar{I} - \frac{R_s}{2} \qquad \text{Expression 5}$$

In step SA3 in the flowchart of FIG. 21, the control section 41 performs contrast correction on the diffuse reflection component image. In step SA4, the control section 41 performs contrast correction on the specular reflection component image. The contrast corrections can be linear corrections. For example, an average of an ROI is corrected to be a median. In the case of 8 bits, a 128 level only has to be set as a median. Consequently, a diffusion component after the correction and a specular reflection component after the correction are obtained.

In step SA5, the control section 41 calculates a difference from a reference phase concerning a phase component. In step SA5, the control section 41 acquires a difference with respect to a phase of a reference plane. For example, the user designates a spherical shape, a cylindrical shape, a plane shape, or the like as the reference plane. The control section 41 acquires a difference from the reference plane. Alternatively, a difference may be extracted on a free curved surface. A phase (a difference) after the correction is obtained concerning the X direction. A phase after the correction is obtained concerning the Y direction as well. An example of a phase image after the correction equivalent to the phase image shown in FIG. 22 is shown in FIG. 29.

The diffuse reflection component image, the specular reflection component image, and the reference phase difference image are output images.

In step SA6, the control section 41 obtains a hierarchical image and a depth contour image on the basis of the reference phase difference image obtained in step SA5. The hierarchical image is an image obtained by repeating ½ reduction. Consequently, hierarchized phase images are respectively obtained in the X direction and the Y direction.

On the other hand, the depth contour image is an intermediate image in which a portion having a large phase difference is emphasized. The depth contour image is a concept different from a curvature. The depth contour image has advantages that, for example, the depth contour image is obtained at high speed compared with a shape image obtained by shape stacking, a line flaw of the work W is extremely easily seen, and extraction of a contour is easily performed. An example of the depth contour image is shown in FIG. 29.

Subsequently, in step SA7, the control section 41 performs shape stacking on the hierarchized phase images to generate a shape image. The shape image can be obtained by performing stacking calculation by the Gauss-Jacobi method or the like on the specular reflection angles in the X direction and the Y direction. The shape image is an output image. An example of the shape image is shown in FIG. 29.

In general, a shape is often restored by triangulation or the like after unwrapping is performed. However, in this embodiment, the unwrapping is avoided and stacking calculation of local differential values is performed by the Gauss-Jacobi method to restore a shape without performing the triangulation. As a shape restoring method, a known method can be used as appropriate. Desirably, the shape restoring method is a method of restoring a shape without using the triangulation. The shape restoring method can also be a hierarchical method including reduced images in multiple stages. The shape restoring method can be a method having a difference between a reduced image and a normal image.

Further, a characteristic size can be set as a parameter. The characteristic size is a parameter for setting size of a detection target flaw corresponding to a purpose and a type of an inspection. For example, when a parameter value of the characteristic size is 1, a finest flaw can be detected. A large flaw can be detected by increasing this value. Consequently, it is easier to detect a larger flaw when the characteristic size is increased. Unevenness on the surface of the work W is made clear.

In step SA8, the control section 41 performs simple defect extraction. Details of the simple defect extraction are explained below. After performing the simple defect extraction in step SA8, the control section 41 outputs a defect extraction image in which an extracted defect is displayed.

The image generating section 42 can also generate a glossy ratio image. The glossy ratio image is an image representing a ratio of a specular reflection component and a diffuse reflection component. In the glossy ratio image, pixels having different rates of specular reflection components and diffuse reflection components are emphasized. An example of the glossy ratio image is shown in FIG. 29.

Configuration of the Filter Processing Section 40

The filter processing section 40 shown in FIG. 2 includes a filter processing setting section 40a capable of individually setting filter processing application and filter processing non-application with respect to the images for inspection generated by the image generating section 42 and a filter processing executing section 40b that executes filter processing on the image for inspection set to the filter processing application by the filter processing setting section 40a. Types of filters to be applied are not particularly limited. However, for example, the types of the filters can be selected according to a kind of an image for inspection. Examples of the filters include a shading correction filter and a smoothing filter.

Figures 30, 31:
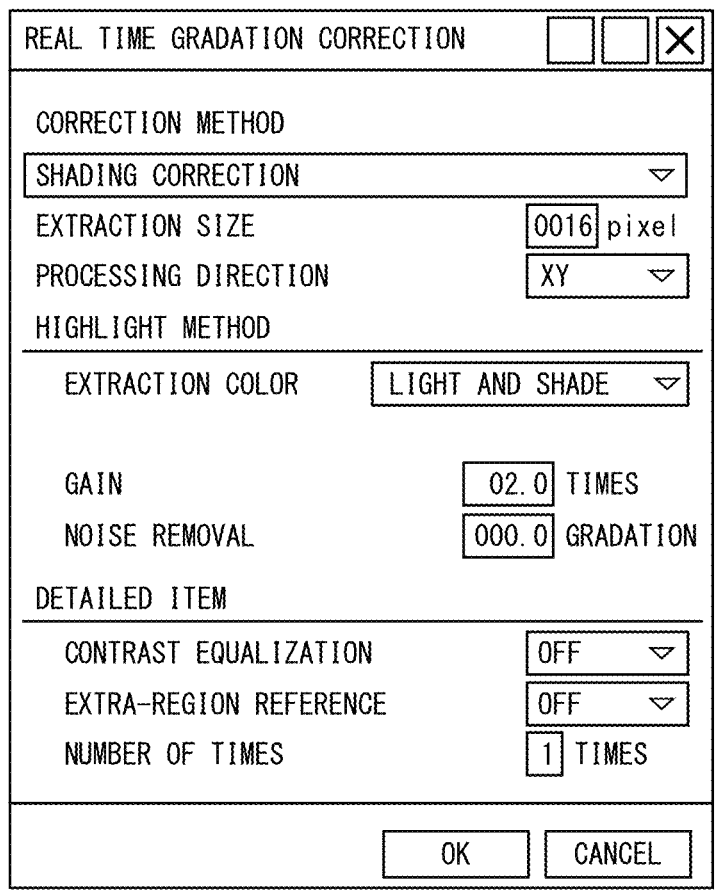
FIG. 30 is a table showing propriety of a filter for images for inspection.
FIG. 31 is a diagram showing an interface for parameter setting of filter processing.

As shown in FIG. 30, the shading correction filter is unsuitable for the shape image, the glossy ratio image, the depth contour image, and the phase image. This is because, since the shape image is not an image of brightness and is an image indicating unevenness, an effect of the shading correction filter is not obtained. Since the glossy ratio image is an image obtained by calculating a ratio, the glossy ratio image is an image in which shading disappears. Since correction is applied to the depth contour image and the phase image taking into account a phase, there is no meaning in applying the shading correction filter. On the other hand, the shading correction filter is suitable for the specular reflection component image, the diffuse reflection component image, and the normal image.

A median filter shown in FIG. 30 is a smoothing filter. The median filter is unsuitable for the shape image but is suitable for the glossy ratio image, the depth contour image, the phase image, the specular reflection component image, the diffuse reflection component image, and the normal image.

The filter processing setting section 40a is configured to obtain information concerning a kind of an image for inspection and automatically set the filter processing application and the filter processing non-application according to the image for inspection. The information concerning the kind of the image for inspection can be obtained from the image generating section 42. As shown in FIG. 30, the filter processing setting section 40a automatically applies the shading correction filter to the specular reflection component image, the diffuse reflection component image, and the normal image and does not automatically apply the shading correction filter to the shape image, the glossy ratio image, the depth contour image, and the phase image. The filter processing setting section 40a does not automatically apply the median filter to the shape image but automatically applies the median filter to the glossy ratio image, the depth contour image, the phase image, the specular reflection component image, the diffuse reflection component image, and the normal image.

That is, effectiveness of the filter processing is investigated beforehand and an image for inspection to which the filter processing is applied is preset in the image inspection apparatus 1. Then, the filter processing setting section 40a can automatically set application and non-application of at least one of the shading correction filter and the smoothing filter according to the kind of the image for inspection. Note that the user may be enabled to change preset content.

The filter processing executing section 40b can execute the filter processing according to the preset content. Therefore, the user does not have to select, for each image for inspection, application and non-application of the filter processing and a kind of the filter processing at the time when the filter processing is applied. Therefore, operability is improved. The filter processing setting section 40a is configured to set the filter processing only for an image for inspection used for an inspection. Therefore, the filter processing is not executed on an image for inspection not used for the inspection.

A type of the filter processing to be preset only has to be a filter that can investigate effectiveness beforehand and a filter in which presence or absence of an effect appears according to an image for inspection.

Figure 25:
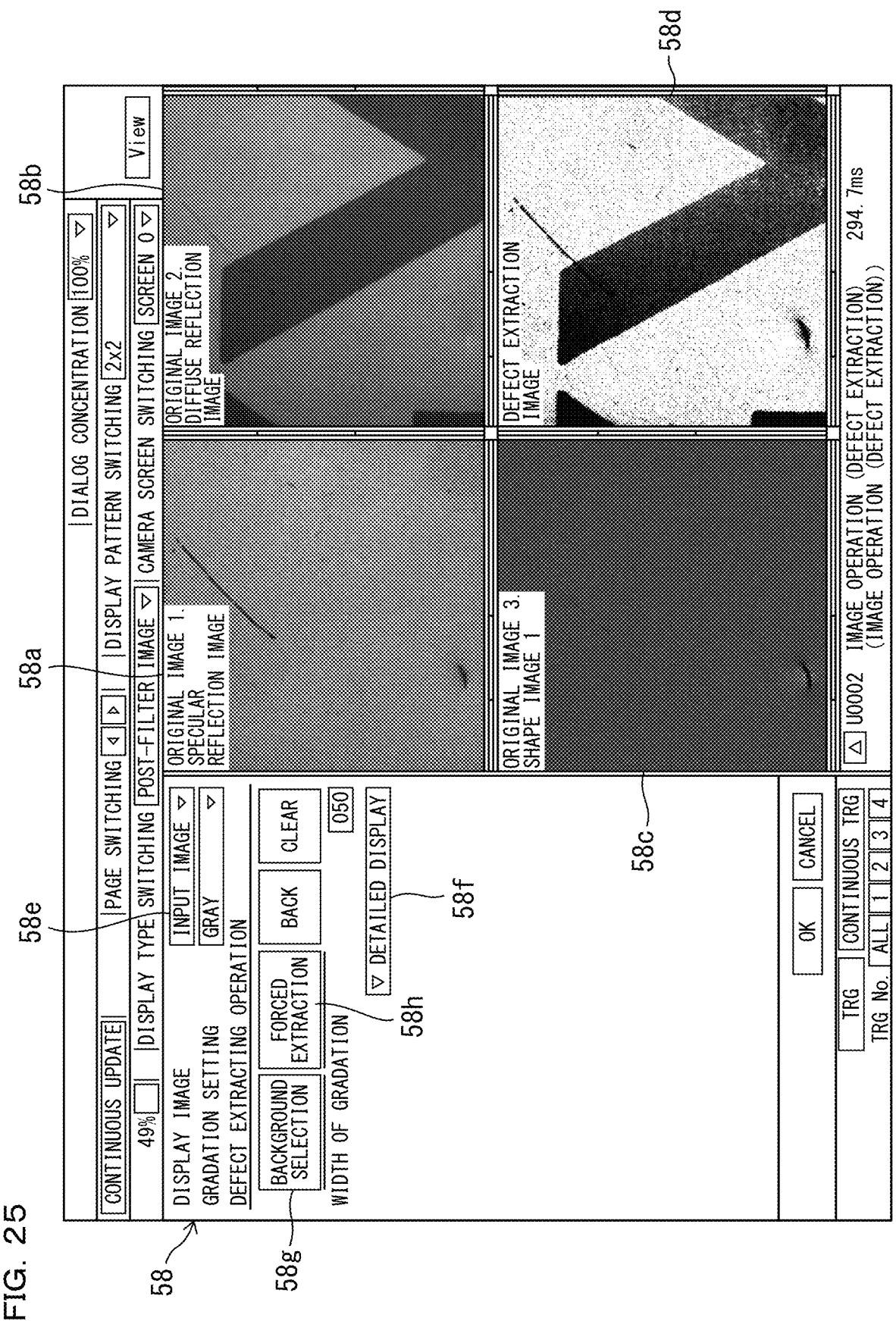
FIG. 25 is a diagram showing an interface for defect extraction.

An image for inspection can be selected by a pulldown menu for display image selection 58e of an interface for defect extraction 58 shown in FIG. 25. An image for inspection (a specular reflection component image, a diffuse reflection component image, etc.) selected as the image for inspection by the pulldown menu for display image selection 58e and subjected to the filter processing by the filter processing executing section 40b and an image for inspection (a shape image, etc.) not subjected to the filter processing by the filter processing executing section 40b can be simultaneously displayed on the display section 5. Even if an image for inspection is suitable for the filter processing, if the image for inspection is not selected as an image for inspection (is not displayed on the display section 5), the filter processing executing section 40b does not have to perform the filter processing on the image for inspection. Even if the filter processing is not performed at this point in time, the filter processing executing section 40b only has to perform the filter processing at a stage when the image for inspection is selected as an image for inspection later.

Note that, on the premise that the filter processing application and the filter processing non-application are automatically set according to a kind of an image for inspection, the user may be able to set automatically-set filter processing to non-application or change a kind of the automatically-set filter processing. For example, the filter processing setting section 40a can be configured to receive operation for setting the filter processing to non-application for an image for inspection for which the filter processing is determined as unnecessary by the user. Specific examples of the operation include operation for causing the display section 5 to display an interface and operating various buttons, a pulldown menu, and the like incorporated in the interface.

The filter processing executing section 40b may be configured to be capable of, when executing the filter processing on a plurality of images for inspection, for the plurality of images for inspection on which the filter processing is executed, collectively setting the filter processing executed on the images for inspection to non-execution. When the user performs operation for setting the filter processing to non-application for the images for inspection, the filter processing executing section 40b can automatically set the filter processing to non-execution for the images for inspection. The filter processing executing section 40b can also be configured to receive resetting operation, that is, operation for executing the filter processing on the plurality of images for inspection after collectively setting the filter processing to non-execution.

When the respective kinds of filter processing are performed, as shown in FIG. 31, various parameters such as intensity of the filter processing can be set. The filter processing executing section 40b is configured to be capable of collectively setting and changing the parameters of the filter processing for an image for inspection set to the filter processing application by the filter processing setting section 40a. When parameters are set or changed by an interface for parameter setting shown in FIG. 31, the filter processing executing section 40b reflects the operation on other images for inspection set to the filter processing application.

An image for inspection to which the filter processing is applied does not have to be preset in the image inspection apparatus 1. In this case, the user operates various buttons, a pulldown menu, and the like incorporated in the interface to individually or collectively set application and non-application of the filter processing for the images for inspection. The various buttons, the pulldown menu, and the like incorporated in the interface are a filter processing setting section.

Figure 32:
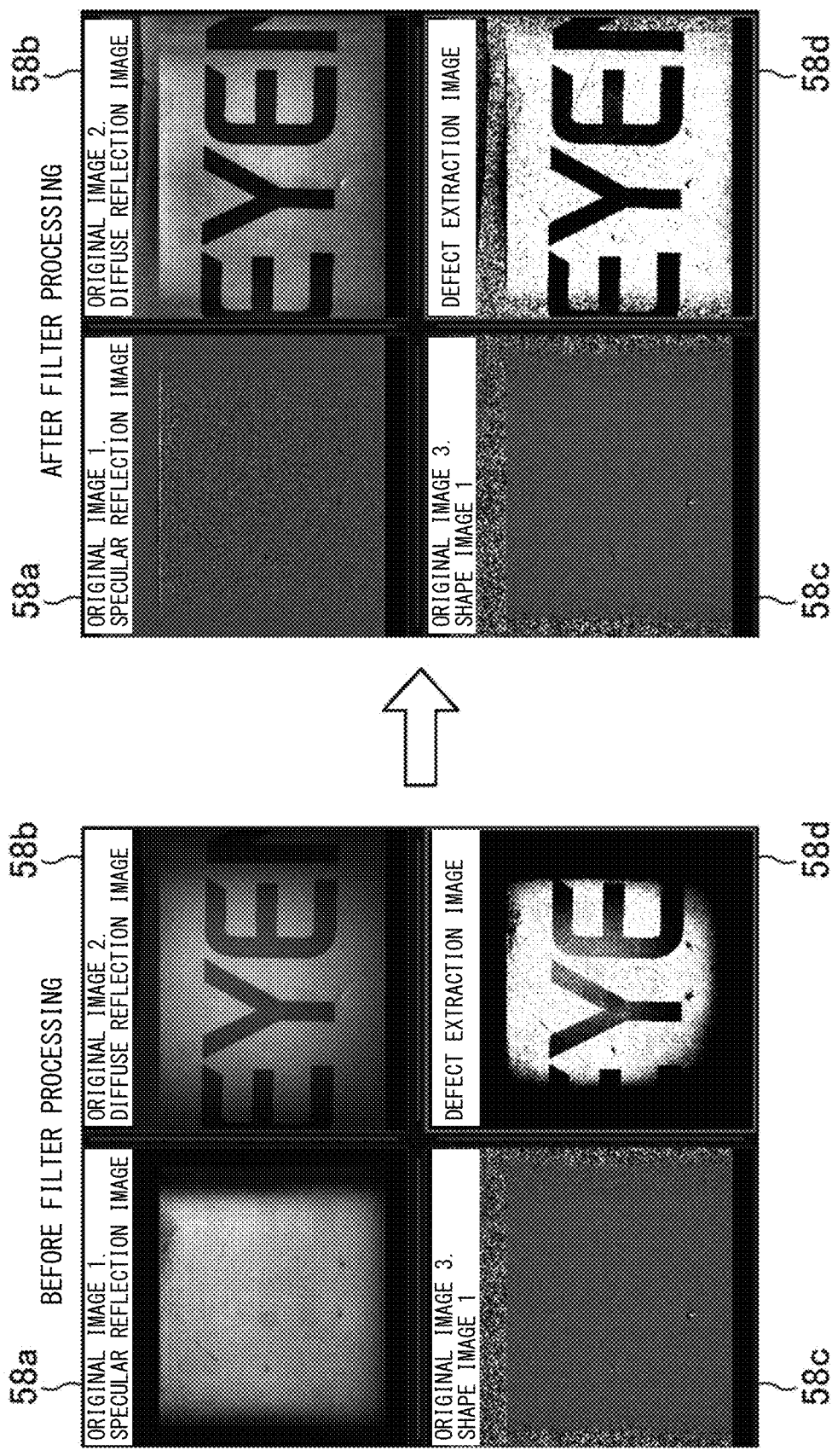
FIG. 32 is a diagram showing a change of an image for inspection before and after the filter processing.

FIG. 32 is a diagram showing an image for inspection before the filter processing and an image for inspection after the filter processing. The filter processing is applied to an original image 1 (a specular reflection component image) displayed in a first image display region 58a and an original image 2 (a diffuse reflection component image) displayed in a second image display region 58b. As shown in FIG. 32, shadings of the specular reflection component image and the diffuse reflection component image are corrected and defective portions are easily seen. On the other hand, the filter processing is not applied to an original image 3 (a shape image) displayed in a third image display region 58c. Therefore, a defective portion related to a shape is still easily seen.

Simple Defect Extraction

Figure 24:
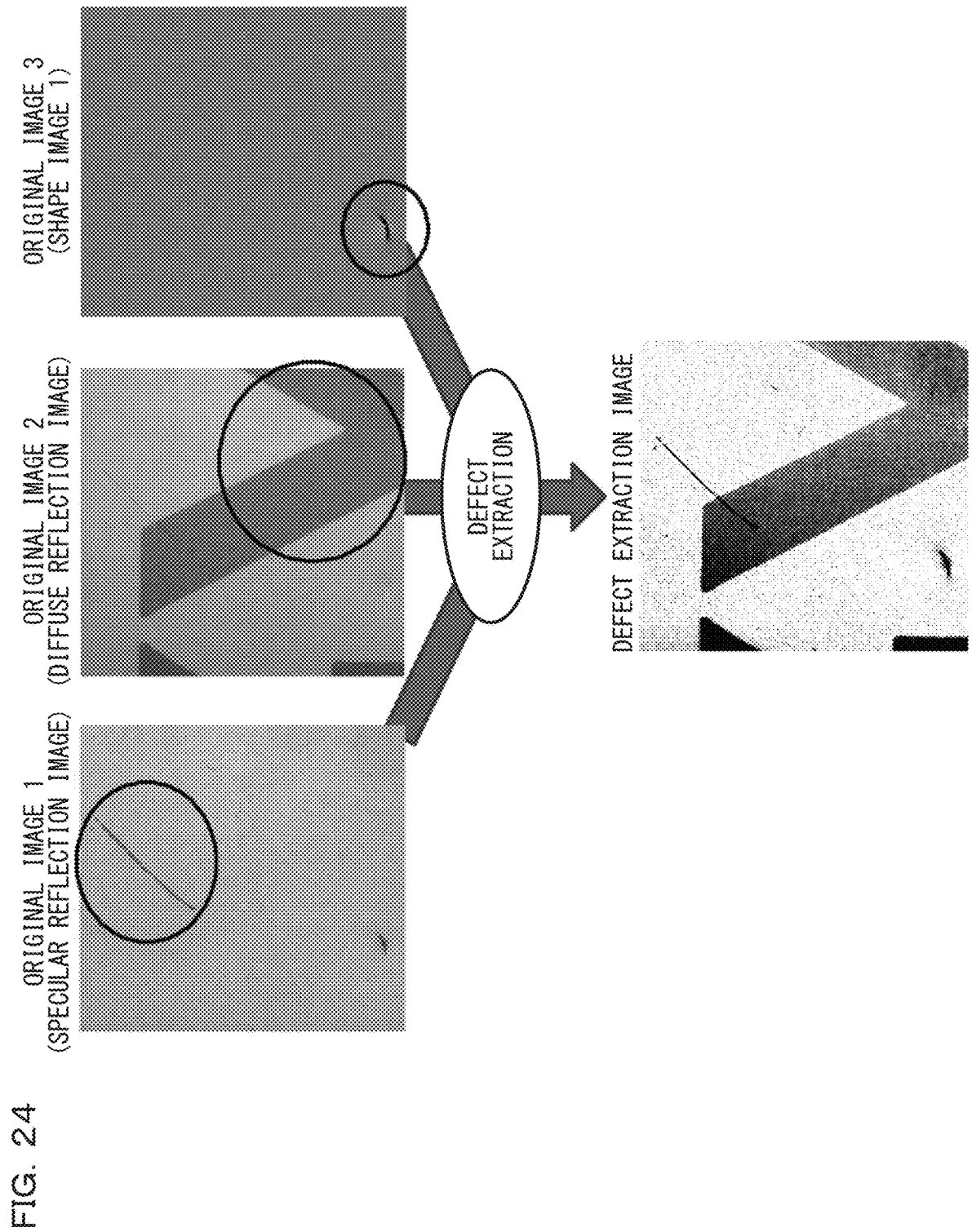
FIG. 24 is a diagram schematically showing a concept of simple defect extraction.

Simple defect extraction is a process for, as indicated by a concept of the simple defect extraction in FIG. 24, respectively generating an image 1 in which a line flaw (a defect) of the work W is easily inspected, an image 2 in which a stain (a defect) of the work W is easily inspected, and an image 3 in which a dent (a defect) of the work W is easily inspected and thereafter displaying the defects appearing in the images 1 to 3 on a defect extraction image. The defect extraction image is an image in which the defects appearing in the images 1 to 3 can be extracted and displayed. The defect extraction image can also be called combined defect image because the extracted defects are combined into one image and displayed.

For example, the specular reflection component image is an image in which a stain that dulls specular reflection, a flaw that does not have a shape change but dulls specular reflection, a flaw that prevents the specular reflection because of a shape change, or the like is easily confirmed. The diffuse reflection image is an image in which a state of texture of the surface of the work W (specifically, characters, a blackish stain, and the like of a print) is easily seen. The shape image is an image obtained by stacking changes in phases while viewing peripheral pixels according to characteristic size. When the characteristic size of the shape image is set large, it is possible to grasp unevenness that is relatively shallow and has a wide area in among shape changes. On the other hand, when the characteristic size of the shape image is set small, it is possible to grasp a line flaw and a flaw having a small area. A defect (e.g., a thin flaw or a deep flaw) less easily appearing in the shape image tends to appear in the specular reflection component image. The depth contour image is obtained by calculating a reference plane and imaging a shift from the reference plane. From the depth contour image, a line flaw and a flaw having a small area can be grasped. That is, the image generating section 42 can generate, on the basis of a plurality of luminance images captured by the imaging section 3, a plurality of images for inspection in which defects of different types can be detected. Images generated by the image generating section 42 are not limited to the images explained above.

The specular reflection component image, the diffuse reflection image, the shape image, the depth contour image, the glossy ratio image, the defect extraction image, and the like generated by the image generating section 42 are images for inspection and can be displayed on the display section 5. Only one of the images generated by the image generating section 42 may be displayed on the display section 5 or any plurality of images may be displayed on the display section 5. The images displayed on the display section 5 are desirably selectable by the user.

For example, the UI generating section 43 can generate the interface for defect extraction 58 shown in FIG. 25 and cause the display section 5 to display the interface for defect extraction 58. The first image display region 58a where the original image 1 is displayed, the second image display region 58b in which the original image 2 is displayed, the third image display region 58c in which the original image 3 is displayed, and a fourth image display region 58d in which the defect extraction image is displayed are incorporated in the interface for defect extraction 58. The number of image display regions is not limited to four and may be three or less or may be five or more. In FIG. 25, the specular reflection component image is selected as the original image 1, the diffuse reflection component image is selected as the original image 2, and the shape image is selected as the original image 3. However, any image may be displayed in any region as long as the image is an image generated by the image generating section 42.

The user can switch the images displayed in the first to third image display regions 58a to 58c to other images. When switching the displayed images, for example, the user can select a display region and activate the display region with, for example, operation of the mouse 7 and perform selection of an image with the pulldown menu for display image selection 58e incorporated in the interface for defect extraction 58. The pulldown menu for display image selection 58e is an image selecting section that selects at least one image for inspection used for an inspection out of a plurality of images for inspection generated by the image generating section 42.

The specular reflection component image, the diffuse reflection image, the shape image, the depth contour image, the glossy ratio image, and the like are displayed as choices in the pulldown menu for display image selection 58e. The image generating section 42 generates a defect extraction image using the selected image for inspection. The pulldown menu for display image selection 58e is an image selection receiving section that can receive selection of an image for inspection for generating a defect extraction image out of the plurality of images for inspection generated by the image generating section 42.

The image inspection apparatus 1 is configured to be capable of designating and enlarging a part of a region of one image for inspection among the images for inspection displayed on the display section 5. For example, when the user desires to enlarge a region B1 indicated by a broken line on an image displayed in the first image display region 58a shown in FIG. 25, the user places a pointer of the mouse 7 on a start point PA and directly performs drag operation to an end point PB with the mouse 7. Then, a rectangular region having a straight line connecting the start point PA and the end point PB as a diagonal line is designated as the region B1. This operation is operation equivalent to enlarging operation for designating and enlarging a part of a region of one image for inspection. The enlarging operation is received by the operation receiving section 46 of the control unit 4. A shape of the region designated by the enlarging operation may be, for example, a shape surrounded by a circle or a free curved line. The enlarging operation may be performed by operation of either one of the mouse 7 and the keyboard 6.

Figure 26:
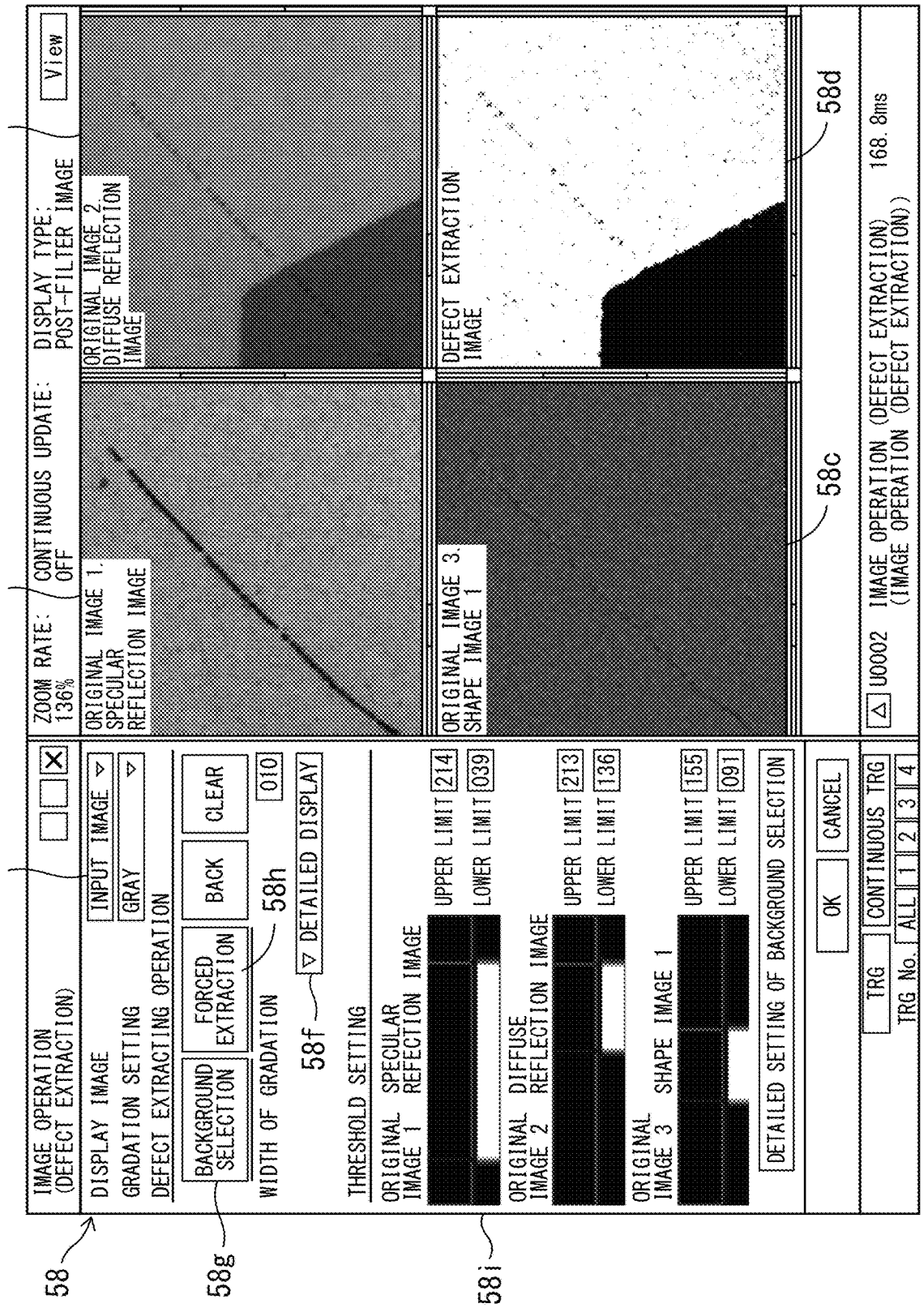
FIG. 26 is a diagram equivalent to FIG. 25 in which a part of an image for inspection is enlarged and displayed.

When receiving the enlarging operation by the user, the display control section 47 of the control unit 4 enlarges the region B1 of the image displayed in the first image display region 58a and displays the region B1 in the first image display region 58a as shown in FIG. 26. Further, in the other images for inspection displayed on the display section 5 (the images displayed in the second to fourth image display regions 58b to 58d) shown in FIG. 25, the display control section 47 enlarges, at the same magnification in association with the enlarging operation, regions B2 corresponding to the region B1 designated in the image displayed in the first image display region 58a and causes the display section 5 to display the regions B2 (see FIG. 26). The enlargement of the region B1 and the enlargement of the regions B2 can be simultaneously performed. However, the enlargements may involve a slight temporal delay. The enlarging operation may be performed on any images for inspection displayed in the first to fourth image display regions 58a to 58d. Irrespective of on which image for inspection the enlarging operation is performed, it is possible to enlarge the other images for inspection at the same magnification in association with the enlarging operation and display the images for inspection on the display section 5.

The operation receiving section 46 may be configured to be capable of receiving reducing operation for reducing one image for inspection among the images for inspection displayed on the display section 5. The reducing operation can be performed by, for example, click operation of the mouse 7 or key operation of the keyboard 6. The display control section 47 may be configured to reduce, at the same magnification in association with the reducing operation, the other images for inspection displayed on the display section 5 and cause the display section 5 to display the images for inspection.

The operation receiving section 46 may be configured to be capable of receiving scroll operation for scrolling one image for inspection among the images for inspection displayed on the display section 5. The scroll operation can be performed by, for example, the click operation of the mouse 7 or the key operation of the keyboard 6. The display control section 47 may be configured to scroll the other images for inspection displayed on the display section 5 in association with the scrolling operation. The direction of the scroll can be set to any direction of the up-down direction, the left-right direction, an oblique direction of the display section 5.

A detailed display button 58f for selecting whether to perform detailed display is incorporated in the interface for defect extraction 58 shown in FIG. 25. When the user operates the detailed display button 58f to perform the detailed display, as shown in FIG. 26, a region for threshold setting 58i is displayed. Thresholds of the original images 1 to 3 can be displayed in the region for threshold setting 58i. The threshold is a value for specifying a pixel value range that should be set as a non-defective portion. For example, when brightness levels of pixels are set to 256 stages of 0 to 255, the pixel value range that should be set as the non-defective portion can be specifies by specific values among 0 to 255. Black may be set as the non-defective portion or, conversely, white may be set as the non-defective portion.
Background Selecting Method There are two methods as a method of setting a threshold. A first method is a method of selecting a background. A background selection button 58g is provided in the interface for defect extraction 58 shown in FIG. 25. The user presses the background selection button 58g and then selects backgrounds of the images for inspection (the original images 1 to 3). The background selection can be performed on the original images 1 to 3 enlarged and displayed after the enlarging operation. The background means a portion other than a defective portion of the work W, that is, a non-defective portion of the work W.

As the method of selecting a background, there are, for example, a method of placing the pointer of the mouse 7 on a non-defective portion of the work W in the original images 1 to 3 and clicking the pointer and a method of operating a touch panel. Consequently, it is possible to designate a position (an X coordinate and a Y coordinate) of a non-defective portion of the work W. The designation of a position of a non-defective portion can be performed a plurality of times on any one image among the original images 1 to 3. After the designation of a position of a non-defective portion is performed on any one image (a first image for inspection) among the original images 1 to 3, the designation of a position of a non-defective portion can also be performed on another image. Note that, when the background selection is performed, the pixel value range that should be set as the non-defective portion changes to expand.

Figure 33:
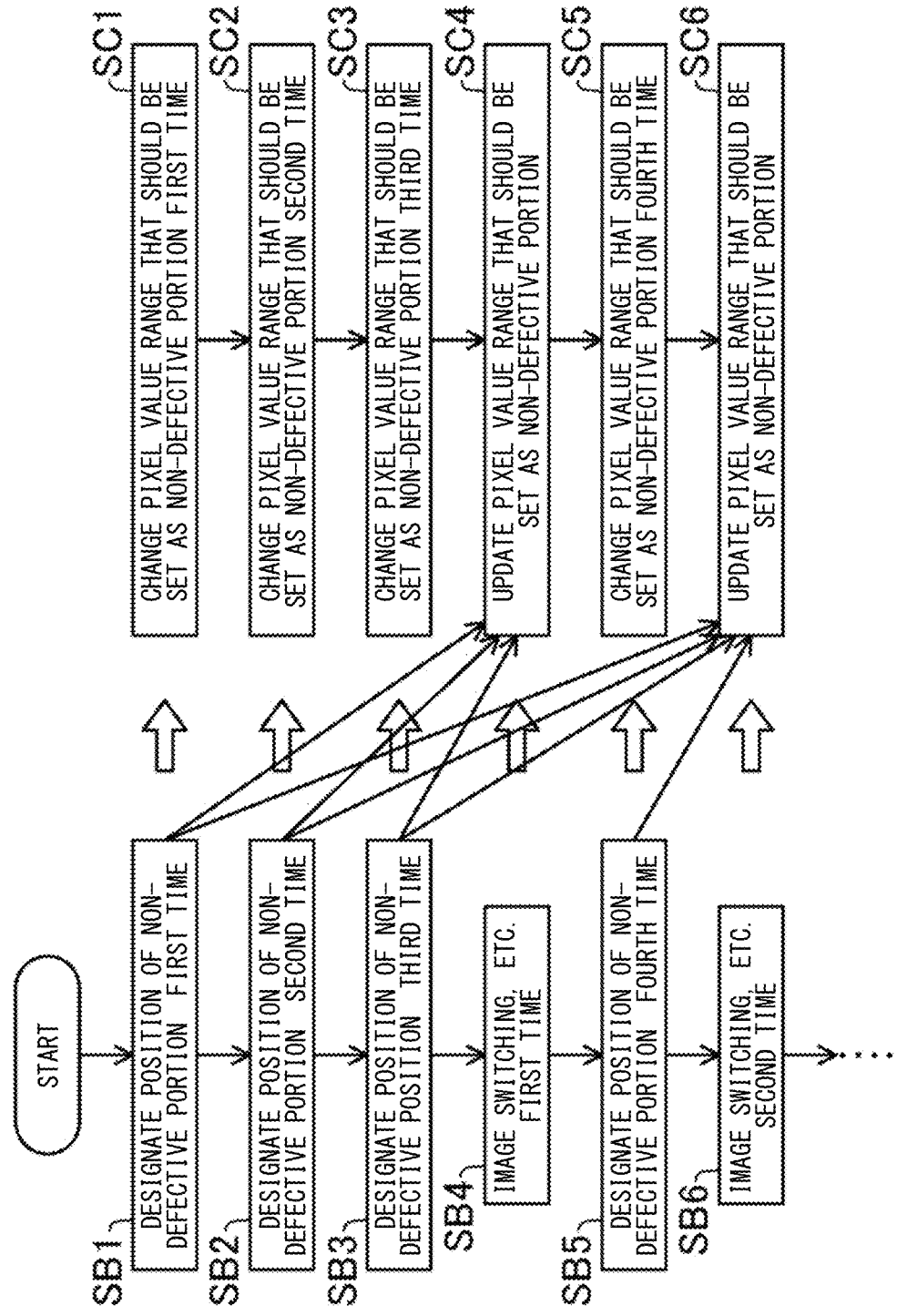
FIG. 33 is a flowchart of background selection performed a plurality of times.

The designation of a position of a non-defective portion is explained with reference to a flowchart of FIG. 33. When the user performs the designation of a position of a non-defective portion of the work W (first time) (step SB1), as internal processing of the control unit 4, the first designation of a position of a non-defective portion is received by the position designation receiving section 48 of the control unit 4. Position information of the non-defective portion (first non-defective portion position information) received by the position designation receiving section 48 is stored in a position information storing section 10b of the storage device 10 as a coordinate format.

The setting section 49 of the control unit 4 reads out, from the position information storing section 10b, the position information of the non-defective portion received by the position designation receiving section 48 and obtains a pixel value of the position of the non-defective portion received by the position designation receiving section 48. Specifically, the setting section 49 acquires not only a pixel in the position of the non-defective portion (a clicked pixel) but also pixel values of 3×3 regions around the pixel (nine pixel values) and calculates a maximum and a minimum. For example, if the maximum is 200, the setting section 49 sets a triple of the sensitivity (e.g., 5) of the background selection as a margin and sets 200+5×3=215 as the maximum. For example, when the minimum is 80, the setting section 49 sets 80−5×3=65 as the minimum. In this case, the pixel value range that should be set as the non-defective portion is 215 to 65. The setting section 49 automatically sets, on the basis of the pixel value of the position of the non-defective portion, for a plurality of images for inspection (including a first image for inspection) displayed on the display section 5, the pixel value range that should be set as the non-defective portion (step SC1). The sensitivity and the margin are examples.

Thereafter, when the user performs the designation of a position of a non-defective portion of the work W (second time) (step SB2), as internal processing of the control unit 4, the second designation of a position of a non-defective portion is received by the position designation receiving section 48 of the control unit 4. Position information of the non-defective portion (second non-defective portion position information) received by the position designation receiving section 48 is stored in the position information storing section 10b of the storage device 10 in the same manner.

The setting section 49 of the control unit 4 reads out, from the position information storing section 10b, the second position information of the non-defective portion received by the position designation receiving section 48 and obtains a pixel value of the second position of the non-defective portion received by the position designation receiving section 48. The setting section 49 automatically sets, on the basis of the pixel value of the second position of the non-defective portion, for the plurality of images for inspection (including the first image for inspection) displayed on the display section 5, a pixel value range that should be set as the non-defective portion (step SC2).

When the user performs designation of a position of a non-defective portion of the work W (third time) (step SB3), similarly, the setting section 49 automatically sets, on the basis of a pixel value of the third position of the non-defective portion, for the plurality of images for inspection (including the first image for inspection) displayed on the display section 5, a pixel value range that should be set as the non-defective portion (step SC3). That is, the position designation receiving section 48 can receive the designation of a position of a non-defective portion a plurality of times.

When an image for inspection (a second image for inspection) not displayed on the display section 5 and not subjected to the filter processing is selected by the pulldown menu for display image selection 58*e* of the interface for defect extraction 58 shown in FIG. 25, switching of an image displayed on the display section 5 is performed (step SB4). When the image for inspection not displayed on the display section 5 and not subjected to the filter processing is selected, the setting section 49 reads out a plurality of kinds of position information (the position information stored in steps SB1 to SB3) indicating the position of the non-defective portion stored in the position information storing section 10*b* and refers to a pixel value corresponding to position information in the image for information. Thereafter, the setting section 49 updates the pixel value range that should be set as the non-defective portion (step SC4). The filter processing section 40 performs the filter processing on the image for inspection. The background selection can be performed on the image for inspection after the switching (step SB5). The position information (the second non-defective portion position information) designated at this time is stored in the position information storing section 10*b*.

Further, after the image for inspection not displayed on the display section 5 and not subjected to the filter processing is selected as the second image for inspection, another image is sometimes further selected as a third image for inspection (step SB6). When the third image for inspection is selected, the setting section 49 reads out a plurality of kinds of position information (the position information stored in steps SB1 to SB3 and SB5) indicating the position of the non-defective portion stored in the position information storing section 10*b* and updates, referring to a pixel value corresponding to the position information in the third image for inspection, the pixel value range that should be set as the non-defective portion. Although not shown in FIG. 33, the background selection can also be performed on the third image for inspection. Position information (third non-defective portion position information) designated at this time is stored in the position information storing section 10*b*. The filter processing section 40 performs the filter processing on the third image for inspection.

That is, when the third image for inspection is selected, the setting section 49 can read out the position information indicating the position of the non-defective portion in the second image for inspection (the second non-defective portion position information) stored in the position information storing section 10*b* and update, referring to a pixel value corresponding to the position information in the second image for inspection, the pixel value range that should be set as the non-defective portion. The setting section 49 may be configured to, when the third image for inspection is selected, read out the position information indicating the position of the non-defective portion in the first image for inspection (the first non-defective portion position information) and the position information indicating the position of the non-defective portion in the second image for inspection (the second non-defective portion position information) stored in the position information storing section 10*b* and update, referring to pixel values corresponding to the first and second non-defective portion position information in the third image for inspection, the pixel value range that should be set as the non-defective portion. Histories of the background selection can be saved for, for example, ten times of the background selection. Older histories can be deleted in order from the oldest history.

A reason for selecting the background rather than the defective portion of the work W is as explained below. If a method of clicking and designating defective portions one by one on a screen of the display section 5, a plurality of defect condition settings have to be performed and operation is complicated. The user has to prepare samples of the defective portions and cannot treat unknown defective portions. The user could sometimes feel stress in designation work for a small defective portion such as a line flaw. Therefore, the background selection is often more desirable. A method of designating a defective portion explained below is sometimes effective. In this embodiment, the user can select the method of selecting a background and the method of designating a defective portion.

Forced Extraction Method

A second method of the method of setting a threshold is a method of designating a defective portion (a forced extraction method). For example, when a difference between a defective portion and a non-defective portion is not very large, the user desires to set a threshold by selecting the defective portion. The forced extraction method is effective in this case.

Figure 27:
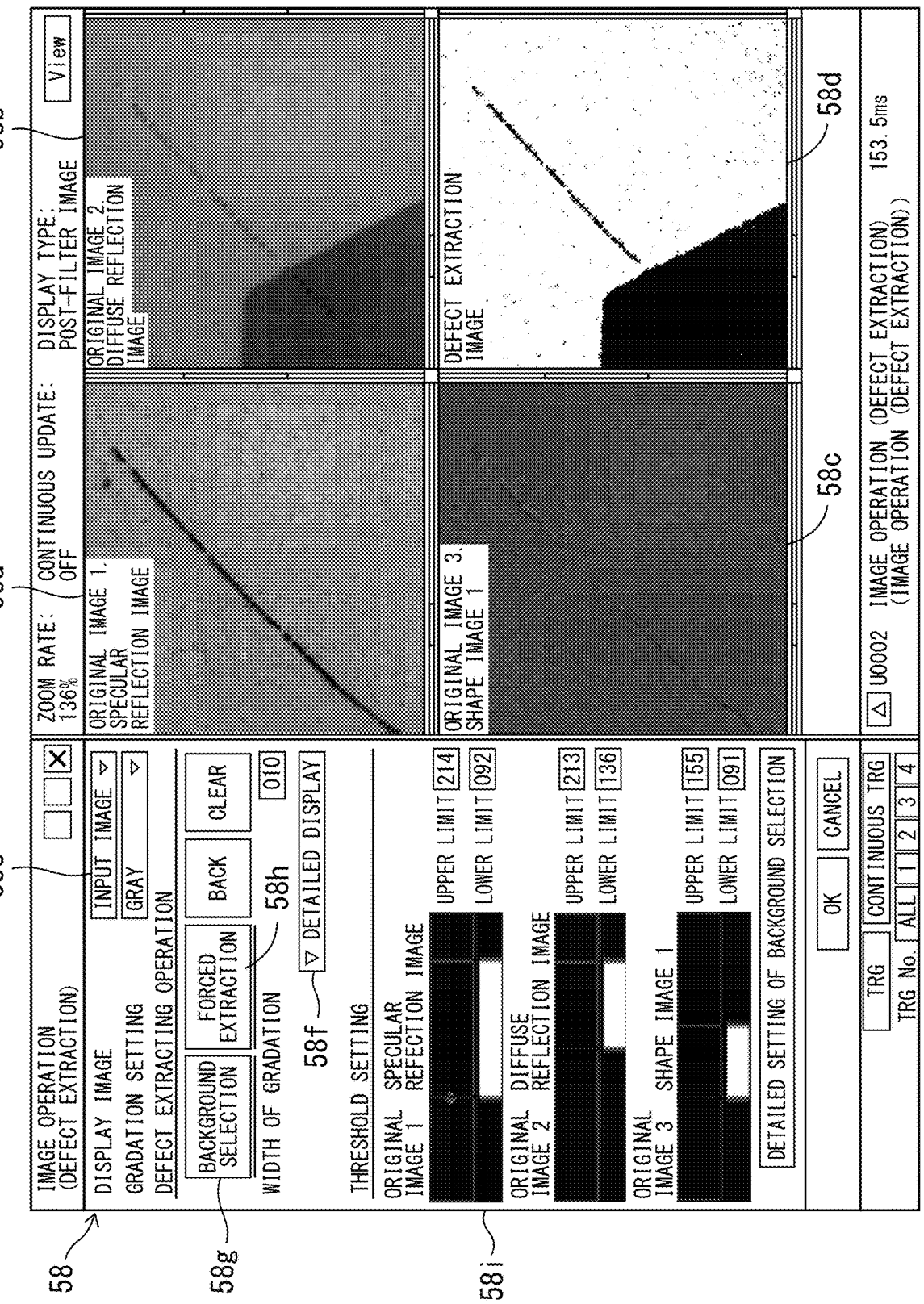
FIG. 27 is a diagram equivalent to FIG. 25 in which forced extraction of a defective part is performed.

A forced extraction button 58*h* is provided in the interface for defect extraction 58 shown in FIG. 25. The user presses the forced extraction button 58*h* and then selects defective portions of images for inspection (shown in FIG. 27). The forced extraction is extracting a defective portion of the work W. The forced extraction can be performed on enlarged and displayed images for inspection. A flow of the forced extraction is substantially the same as the flow in the case of the background selection shown in FIG. 33.

As the method of the forced extraction, there are, for example, a method of placing the pointer of the mouse 7 on a non-defective portion of the work W in the original images 1 to 3 and clicking the pointer and a method of operating a touch panel. Consequently, it is possible to designate a position (an X coordinate and a Y coordinate) of the defective portion of the work W. The designation of a position of a defective portion can be performed a plurality of times on any one image among the original images 1 to 3. After the designation of a position of a defective portion is performed on any one image (a first image for inspection) among the original images 1 to 3, the designation of a position of a defective portion can also be performed on another image. Note that, when the forced extraction is performed, the pixel value range that should be set as the non-defective portion changes in a narrowing direction. The forced extraction and the background selection can be performed on one original image.

The designation of a position of a defective portion of the work W is received by the position designation receiving section 48 of the control unit 4 shown in FIG. 2. The position designation receiving section 48 can receive the designation of a position of a defective portion a plurality of times. Position information (a coordinate) of the defective portion received by the position designation receiving section 48 is stored in the position information storing section 10*b* of the storage device 10.

The setting section 49 of the control unit 4 reads out, from the position information storing section 10*b*, the position information of the defective portion received by the position designation receiving section 48 and obtains a pixel value of the position of the defective portion received by the position designation receiving section 48. In the case of the forced extraction, unlike the case of the background selection, the setting section 49 acquires a pixel value of a pixel in the position of the defective portion (a clicked pixel) and automatically sets, on the basis of the pixel value of the position of the defective portion, with respect to the plurality of images for inspection (including the first image for inspection) displayed on the display section 5, the pixel value range that should be set as the non-defective portion. At this time, the setting section 49 sets the pixel value range that should be set as the non-defective portion such that the pixel value range does not include the pixel value of the position of the defective portion. However, when the pixel value range after the change is not an effective range, the setting section 49 sets an upper limit value to 0 and sets a lower limit value to 255.

When an image for inspection (a second image for inspection) not displayed on the display section 5 and not subjected to the filter processing is selected, the setting section 49 reads out a plurality of kinds of position information indicating the position of the defective portion stored in the position information storing section 10b and refers to a pixel value corresponding to position information in the second image for inspection. The setting section 49 updates the pixel value range that should be set as the non-defective portion in the second image for inspection. The filter processing section 40 performs the filter processing on the second image for inspection. The forced extraction can be performed on the second image for inspection. The position information designated at this time is stored in the position information storing section 10b.

Further, after an image for inspection not displayed on the display section 5 and not subjected to the filter processing is selected as the second image for inspection, when another image is further selected as a third image for inspection, the setting section 49 reads out the plurality of kinds of position information indicating the position of the defective portion stored in the position information storing section 10b and updates the pixel value range that should be set as the non-defective portion referring to a pixel value corresponding to the position information in the third image for inspection. The filter processing section 40 performs the filter processing on the third image for inspection.

When the third image for inspection is selected, the setting section 49 can read out position information indicating the position of the defective portion in the second image for inspection (second defective portion position information) stored in the position information storing section 10b and update the pixel value range that should be set as the non-defective portion referring to a pixel value corresponding to the position information in the second image for inspection.

The setting section 49 may be configured to, when the third image for inspection is selected, read out the position information (the first defective portion position information) indicating the position of the defective portion in the first image for inspection and the position information (the second defective portion position information) indicating the position of the defective portion in the second image for inspection stored in the position information storing section 10b and update, referring to pixel values, corresponding to the first and second defective portion position information in the third image for inspection, the pixel value range that should be set as the non-defective portion.

The image generating section 42 generates a defect extraction image in which a region included in all the pixel value regions that should be set as the non-defective portion set for the plurality of images for inspection by the setting section 49 is set as a non-defective region and a region not included in any one of the pixel value ranges is set as a defective region. The defect extraction image can be displayed in the fourth image display region 58d shown in FIGS. 26 and 27. The pixel value range that should be set as the non-defective portion is changed when the background selection or the forced extraction is performed. However, when designation of a position of a non-defective portion or a defective portion is received by the position designation receiving section 48, the image generating section 42 can automatically update the non-defective region and the defective region in the defect extraction image.

The display control section 47 can enlarge, at the same magnification in association with the enlarging operation, a region corresponding to a region designated in another image for inspection in the defect extraction image displayed on the display section 5 and cause the display section 5 to display the region. The display control section 47 can reduce, at the same magnification in association with the reducing operation, a region corresponding to a region designated in another image for inspection in the defect extraction image displayed on the display section 5 and cause the display section 5 to display the region. Further, the display control section 47 can scroll, in association with the scroll operation, the defect extraction image displayed on the display section 5.

The display control section 47 can also perform the background selection after performing the forced extraction and perform the forced extraction after performing the background selection.

Histograms and Pins

Figure 28:
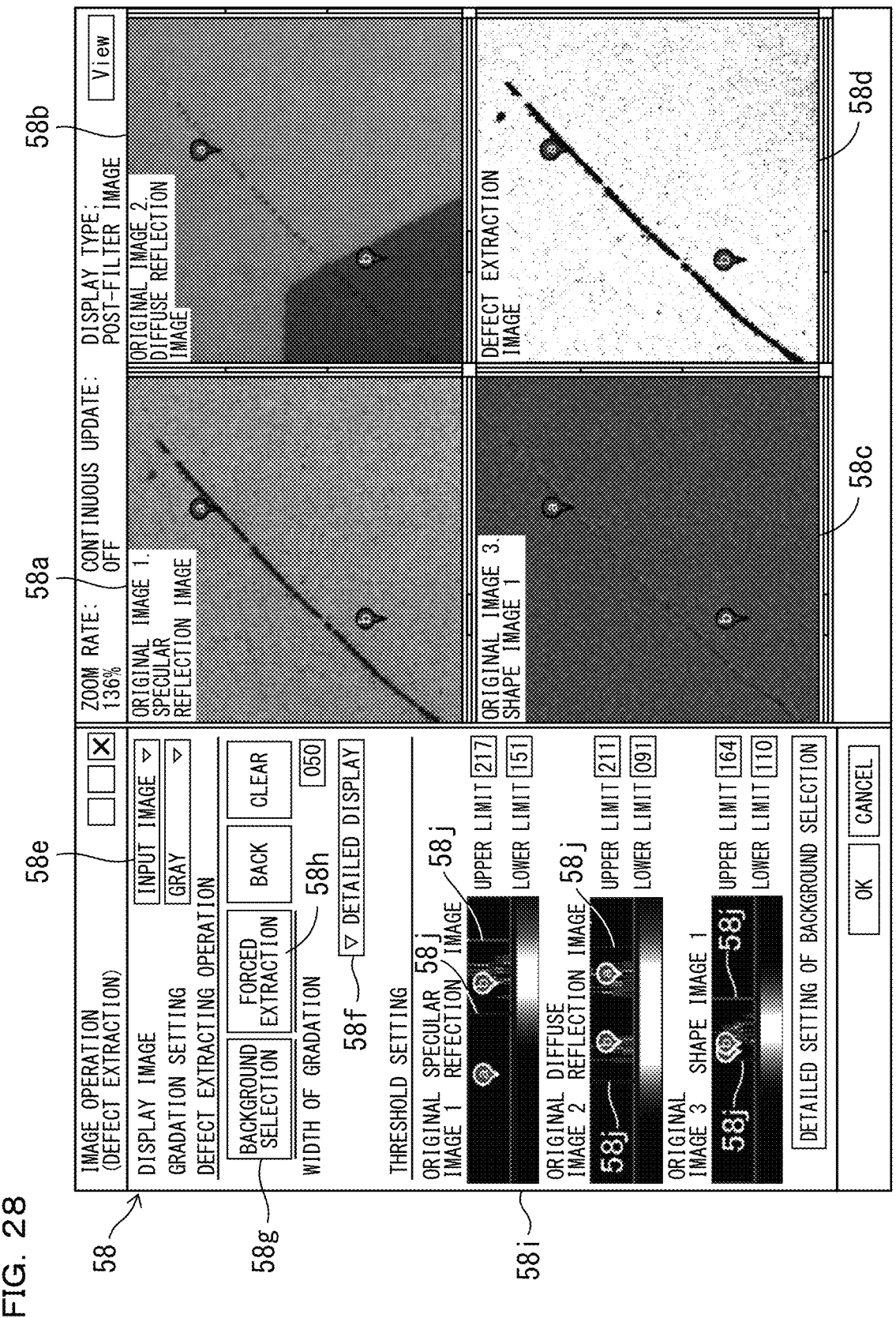
FIG. 28 is a diagram showing an example in which histograms and pins are displayed during threshold setting.

As shown in FIG. 28, histograms and pins can also be displayed during the threshold setting. For example, when any position of the original image 1 displayed in the first image display region 58a is clicked by the mouse 7, a pin marked "A" is displayed. Then, in the region for threshold setting 58i, the same pin marked "A" is displayed in a place corresponding to a pixel value of a clicked point of the original image 1. It is possible to learn the pixel value of the clicked point of the original image 1. When another one point is clicked, a pin marked "B" is displayed. It is possible to learn a pixel value of the position of the pin. It is possible to distinguish and learn the respective pixel values of the pin of A and the pin of B. Three or more pins can be displayed. When the pins are displayed in the original image 1, pins are displayed in corresponding positions of other images for inspection in the same manner. When an image for inspection is switched, it is possible to display pins in corresponding positions of the image for inspection after the switching.

Note that the "pin" is an example of an object indicating that the user designates any position of the image for inspection. A display shape does not have to be a pin shape and may be a form such as an arrow or a flag.

In the region for threshold setting 58i, a histogram, which is a frequency distribution of a pixel value, can also be displayed. The histogram can be generated by a histogram generating section 42a of the control unit 4 shown in FIG. 2. The histogram generating section 42a generates a histogram of a region including the position of the non-defective portion or the defective portion received by the position designation receiving section 48.

In the region for threshold setting 58i, two threshold display lines 58j respectively indicating an upper limit and a lower limit of the pixel value range that should be set as the non-defective portion are displayed. The user can optionally change, with drag operation of the threshold display lines 58j by the mouse 7, at least one of the pixel value range that should be set as the non-defective portion and the pixel value range that should be set as the defective portion while viewing, for example, the histogram displayed in the region for threshold setting 58*i*. The drag operation can be received by the operation receiving section 46. That is, a change of at least one of the pixel value range that should be set as the non-defective portion and the pixel value range that should be set as the defective portion can be received on the histogram generated by the histogram generating section 42*a*. The setting section 49 sets, on the basis of the pixel value range after the change received by the operation receiving section 46, for a plurality of images for inspection, the pixel value range that should be set as the non-defective portion.

The threshold setting method is not limited to the method explained above. Various methods can be used. For example, it is also possible to set a threshold as a brightness ratio of the original image 1 and the original image 2. It is also possible to combine a plurality of conditions to set a threshold. In this case, the user may be able to customize logic operations (OR and NOT).

It is also possible to determine brightness of a post-processing image using a distance used in the statistics such as the Mahalanobis distance and generate a gray image with a statistically reasonable method according to a degree of deviation from the threshold.

The operation for performing the background selection and the operation for performing the forced extraction can be a method of using a minimum and a maximum in a predetermined region. However, even if a pixel value is within the predetermined region, if the pixel value greatly deviates from other pixel values, the pixel value may be excluded from an arithmetic operation. Even if there is a value such as an outlier, it is possible to robustly perform operation using a standard deviation of the pixel value within the predetermined region. The predetermined region may be a rectangular region or region segmentation may be used. Consequently, it is possible to acquire a large quantity of pixels similar to one another to a certain degree. Therefore, it is easy to perform automatic setting of a threshold.

The pixel value range of the non-defective portion may be automatically determined using clustering. Consequently, a plurality of times of click operation is unnecessary. An appropriate threshold can be set by designating a region including the defective portion and a region not including the defective portion and finding, from the regions, an outlier equivalent to a defect.

It is also possible to compare distributions of the background selection and the forced extraction and determine a threshold suitable for separation of the defective portion and the non-defective portion. It is also possible to compare the distributions of the background selection and the forced extraction and display whether two groups can be separated. It is also possible to compare the distributions of the background selection and the forced extraction, determine which image type is optimum to separate the two groups, and perform setting of a threshold using the image type.

Further, when the background selection or the forced extraction is performed, the display of the image for inspection may be binarized or may be displayed in a gray scale. In the case of the binarization, the inside of a range of a threshold of all the images for inspection can be set as the non-defective portion and the outside of the range can be set as the defective portion.

Control of the Pattern Light Illuminating Section by the Control Section 41

In this embodiment, the deflectometry processing is performed after the eight luminance images are obtained as shown in FIG. 23. However, an algorithm of the deflectometry processing is configured after provisionally specifying irradiation order of pattern lights irradiated from the pattern light illuminating section 2. In this embodiment, the algorithm is configured assuming that the irradiation order of the pattern lights on the algorithm is the order of the Y-direction pattern light in the case of 0°, the Y-direction pattern light in the case of 90°, the Y-direction pattern light in the case of 180°, and the Y-direction pattern light in the case of 270° shown in FIG. 5A and the X-direction pattern light in the case of 0°, the X-direction pattern light in the case of 90°, the X-direction pattern light in the case of 180°, and the X-direction pattern light in the case of 270° shown in FIG. 5B.

The moving work W is imaged by the imaging section 3 during the operation of the image inspection apparatus 1. It is conceivable that, during the imaging, a positional relation between the pattern light illuminating section 2 and the imaging section 3 is not in a predetermined state. In particular, in this embodiment, since the pattern light illuminating section 2 and the imaging section 3 are separate, the user can freely set the pattern light illuminating section 2 and the imaging section 3. Therefore, it is assumed that a shift direction of a phase of an illuminance distribution of pattern light is easily set in a direction different from a direction specified by the algorithm.

If, for example, although the shift direction of the phase of the illuminance distribution of the pattern light is specified as the X direction from first irradiation until fourth irradiation in the algorithm, the phase shifts in the Y direction from the first irradiation until the fourth irradiation in an actual setting state, it is possible to repeat illumination and imaging to obtain a plurality of luminance images. However, an image for inspection is generated on the basis of a luminance image captured under inappropriate conditions. Therefore, a recess present in the work W less easily appears in the image for inspection, the recess should be displayed in black but is displayed in white to the contrary, or the recess is displayed in a mixed state of white and black.

Figure 34:
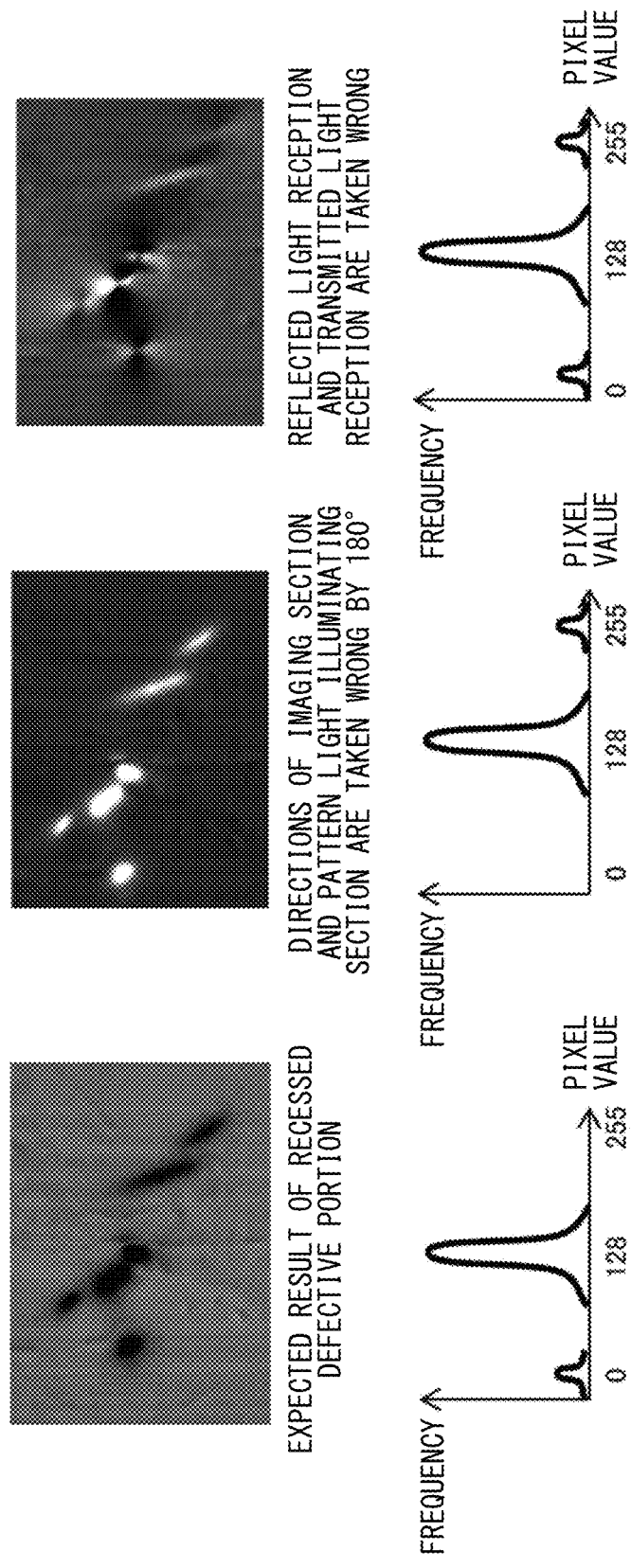
FIG. 34 is a diagram showing an example of images for inspection obtained when a positional relation between the pattern light illuminating section and the imaging section is correct and when the positional relation is wrong.

Specifically, as shown in FIG. 34, when the shift direction of the phase of the illuminance distribution of the pattern light is the direction specified by the algorithm, as shown on the left side in FIG. 34, a recessed defective portion is displayed to be black in the image for inspection. However, as shown in the center in FIG. 34, when the direction of the pattern light illuminating section 2 and the imaging section 3 is different 180° from the direction assumed in the algorithm, the recessed defective portion is displayed in white. Therefore, the user is likely to misrecognize that the defective portion is a convex defective portion. As shown in the right side in the figure, when, although the positional relation between the pattern light illuminating section 2 and the imaging section 3 is actually reflected light reception, the positional relation is set as transmitted light reception, a white portion and a black portion are mixed and displayed.

In this respect, in this embodiment, the information acquiring section 9 acquires moving direction information concerning the moving direction of the work W with respect to the array direction of the light receiving elements 3*a* of the line camera 31 of the imaging section 3 and positional relation information concerning the positional relation between the light receiving elements 3*a* and the pattern light illuminating section 2. The control section 41 can determine, according to the moving direction information and the positional relation information acquired by the information acquiring section 9, a phase shift direction of pattern light irradiated by the pattern light illuminating section 2.

That is, even if the pattern light illuminating section 2 and the imaging section 3 are set such that the shift direction of the phase of the illuminance distribution is a direction different from the direction specified by the algorithm, it is possible to reset, on the basis of the moving direction information and the positional relation information, the phase shift direction of the pattern light irradiated by the pattern light illuminating section 2 to the direction specified by the algorithm.

Therefore, it is unnecessary to rest the pattern light illuminating section 2 and the imaging section 3. Even if the pattern light illuminating section 2 and the imaging section 3 can only be set because of limitation of a setting place and a relation of wiring such that the shift direction of the phase of the illuminance distribution is a direction different from the direction specified by the algorithm, it is possible to perform the image inspection applied with the deflectometry principle.

That is, when the pattern light illuminating section 2 and the imaging section 3 are set such that the shift direction of the phase of the illuminance distribution is a direction different from the direction specified by the algorithm, an appropriate image for inspection cannot be obtained. Therefore, it is possible to control the first light emitting diode rows A1 to A12 and the second light emitting diode rows B1 to B12 to change the irradiation order of the pattern lights such that an appropriate image for inspection can be obtained.

Generation of an Image for Inspection by the Image Generating Section 42

The image generating section 42 can also generate an image for inspection related to the shape of the work W according to the moving direction information and the position relation information acquired by the information acquiring section 9. Consequently, when the pattern light illuminating section 2 and the imaging section 3 are set such that the shift direction of the phase of the illuminance distribution is a direction different from the direction specified by the algorithm, it is possible to obtain an appropriate image for inspection with the generation method of the image generating section 42 without changing the irradiation order of the pattern lights of the pattern light illuminating section 2.

By obtaining the moving direction information and the positional relation information, it is possible to grasp how the pattern light is irradiated on the work W. Irrespective of which direction the shift direction of the phase of the pattern light is, the image generating section 42 can treat an image and generate an image for inspection related to the shape of the work W such that the shift direction coincides with the shift direction of the position of the pattern light specified by the algorithm. If, for example, although the shift direction of the phase of the illuminance distribution of the pattern light is specified as the X direction from first irradiation until fourth irradiation and specified as the Y direction from fifth irradiation until eighth irradiation in the algorithm, the phase shifts in the Y direction from the first irradiation until the fourth irradiation and shifts in the X direction from the fifth irradiation until the eighth irradiation in an actual setting state, imaging is performed without changing the irradiation order of the pattern lights. After the imaging, luminance images obtained in the fifth irradiation to the eighth irradiation are treated as luminance images obtained in the first irradiation to the fourth irradiation in the algorithm. Luminance images obtained in the first irradiation to the fourth irradiation are treated as luminance images obtained in the fifth irradiation to the eighth irradiation in the algorithm. By changing and processing the actually captured luminance images in this way, it is possible to perform the image inspection applied with the deflectometry principle without changing a setting state of the pattern light illuminating section 2 and the imaging section 3.

Configuration of an Inspecting Section

As shown in FIG. 2, an inspecting section 4a is provided in the control unit 4. The inspecting section 4a executes a defect inspection of the work W on the basis of an image for inspection generated by the image generating section 42. For example, the inspecting section 4a determines on the basis of the threshold whether a non-defective portion is present in the work W. When determining that a non-defective portion is present, the inspecting section 4a can inform to that effect.

HDR Function

A high dynamic range imaging (HDR) function can be incorporated in the image inspection apparatus 1. In the HDR function, the control section 41 controls the pattern light illuminating section 2 and the imaging section 3 to obtain a plurality of luminance images having different levels of brightness. Examples of the luminance images obtained by the HDR function include a plurality of luminance images having different exposure times, a plurality of luminance images having different light emission intensities of the pattern light illuminating section 2, and a plurality of luminance images having different exposure times and different light emission intensities. For example, by combining three luminance images having different levels of brightness, the image generating section 42 can generate an image for inspection having a dynamic range wider than dynamic ranges of the luminance images. As a method of the HDR combination, a well-known method in the past can be used.

A plurality of luminance images need to be obtained by the HDR function. In this case, as explained in the section of the transmission of the trigger signal, the trigger signal transmitting section 4b can be configured to, when receiving one encoder pulse signal from the outside, sequentially transmit a plurality of trigger signals to the pattern light illuminating section 2 and the imaging section 3 such that a plurality of luminance images are generated with at least one of the illumination conditions of the pattern light illuminating section 2 and the imaging conditions of the imaging section 3 changed.

Multi-Spectrum Illumination

The pattern light illuminating section 2 may be configured to be capable of performing multi-spectrum illumination. The multi-spectrum illumination is irradiating lights having different wavelengths on the work W while shifting timings. The multi-spectrum illumination is suitable for inspecting color unevenness, a stain, and the like of a print (an inspection target object). For example, the pattern light illuminating section 2 can be configured to be capable of irradiating yellow, blue, and red lights on the work W in order. Specifically, the pattern light illuminating section 2 may include LEDs of a large number of colors. The pattern light illuminating section 2 may be configured by a liquid crystal panel, an organic EL panel, or the like.

The imaging section 3 images the work W at timings when lights are irradiated and obtains a plurality of luminance images. The image generating section 42 can combine the plurality of luminance images to obtain an image for inspection. The lights can include an ultraviolet ray and an infrared ray.

Action and Effects of the Embodiment

As explained above, according to this embodiment, the plurality of pattern lights are sequentially irradiated on the work W. Every time the pattern light is irradiated, the work W is imaged to generate a plurality of luminance images. Phase data indicating the shape of the work W is generated on the basis of the plurality of luminance images. An image for inspection related to the shape of the work W is generated. Therefore, it is possible to perform an image inspection applied with the deflectometry principle.

Even if the pattern light illuminating section 2 and the imaging section 3 are set such that the shift direction of the phase of the illuminance distribution is a direction different from the direction assumed in the algorithm, it is possible to set the phase shift direction of the pattern light irradiated by the pattern light illuminating section 2 to an appropriate direction according to the moving direction information concerning the moving direction of the work W with respect to the array direction of the light receiving elements 3a and the positional relation information concerning the positional relation between the light receiving elements 3a and the pattern light illuminating section 2.

Even if the pattern light illuminating section 2 and the imaging section 3 are set such that the shift direction of the phase of the illuminance distribution is a direction different from the direction assumed in the algorithm, it is possible to generate, with the image generating section 42, an image for inspection related to the shape of the work W according to the moving direction information and the positional relation information.

A plurality of images for inspection can be simultaneously displayed on the display section 5. In a state in which the plurality of images for inspection are simultaneously displayed on the display section 5, when the user views a certain image for inspection and designates a position of a non-defective portion or a defective portion of the work W, it is possible to receive a result of the designation and set, on the basis of a pixel value of the position of the non-defective portion or the defective portion, for a plurality of images for inspection, a pixel value range that should be set as the non-defective portion. Consequently, even if the user does not designate the position of the non-defective portion or the defective portion for all the images for inspection, it is possible to determine presence or absence of a defect in the plurality of images for inspection.

It is possible to generate a defect extraction image in which a region included in all the pixel value regions that should be set as the non-defective portion set for the plurality of images for inspection is set as a non-defective region and a region not included in any one of the pixel value ranges is set as a defective region. Therefore, the user can perform detection of defects of different types simply by viewing the defect extraction image.

In the state in which the plurality of images for inspection are simultaneously displayed on the display section 5, when the user performs operation for designating and enlarging a part of a region of one image for inspection, corresponding regions in the other images for inspection are enlarged at the same magnification and displayed on the display section 5. Consequently, it is possible to enlarge and display the plurality of images for inspection in the same manner with simple operation. The user can designate the position of the non-defective portion or the defective portion of the work W in a certain image for inspection viewing the images for inspection in which the same regions are enlarged and displayed at the same magnification.

When a plurality of images for inspection, in which detection of defects of different types can be detected, are generated, the user can simultaneously view an image for inspection on which the filter processing is executed and an image for inspection on which the filter processing is not executed.

Second Embodiment

In the first embodiment, the function of performing the deflectometry processing on the obtained luminance image to thereby generate an image for inspection is explained. However, besides the deflectometry processing function, for example, a function of generating an image for inspection making use of a photometric stereo method can also be imparted to the image inspection apparatus 1 according to the present invention.

Concerning generating an image for inspection making use of the photometric stereo method, differences from the first embodiment are explained in detail with reference to FIG. 38. The same sections as the sections in the first embodiment are denoted by the same reference numerals and signs and explanation of the sections is omitted.

The image inspection apparatus 1 according to the second embodiment can be configured the same as, for example, the image inspection apparatus disclosed in Japanese Patent Application Laid-Open No. 2015-232486. That is, the image inspection apparatus 1 includes the imaging section 3 that images the work W from a fixed direction, an illuminating section 200 for illuminating the work W from different three or more illumination directions, and a control unit 400. The image inspection apparatus 1 includes the display section 5, the keyboard 6, and the mouse 7 same as those in the first embodiment.

The illuminating section 200 is configured to irradiate lights on the work W from directions different from one another. The illuminating section 200 includes first to fourth light emitting sections 201 to 204 and an illumination control section 205 that controls the first to fourth light emitting sections 201 to 204. The illuminating section 200 is a section that executes plural-direction illumination for irradiating lights on the work W from directions different from one another. The first to fourth light emitting sections 201 are disposed to surround the work W at intervals from one another. As the first to fourth light emitting sections 201 to 204, a light emitting diode, a light bulb, a fluorescent lamp, and the like can be used. The first to fourth light emitting sections 201 to 204 may be separate or may be integrated.

The control unit 400 includes a control section 401, a normal vector calculating section 402, a contour image generating section 403, a texture visualized image generating section 404, and a trigger signal transmitting section 405. The control section 401 is configured to be capable of receiving an encoder pulse signal when the encoder pulse signal is input from the outside. The trigger signal transmitting section 405 is configured to, when the control section 401 receives one encoder pulse signal from the outside, sequentially transmit a plurality of imaging trigger signals to the imaging section 3 such that a plurality of luminance images are generated with at least one of illumination conditions of the illuminating section 200 and imaging conditions of the imaging section 3 changed. The trigger signal transmitting section 405 is configured to, when the control section 401 receives one encoder pulse signal from the outside, sequentially transmit a plurality of illumination trigger signals to the illuminating section 200. In this embodiment, since the first to fourth light emitting sections 201 to 204 are sequentially lit, the trigger signal transmitting section 405 transmits the illumination trigger signal four times. The trigger signal transmitting section 405 transmits the imaging trigger signal four times in synchronization with the transmission of the illumination trigger signal.

For example, when the illuminating section 200 receives a first illumination trigger signal, the illumination control section 205 lights only the first light emitting section 201. At this time, the imaging section 3 receives the imaging trigger signal and images the work W at timing when light is irradiated. When the illuminating section 200 receives a second illumination trigger signal, the illumination control section 205 lights only the second light emitting section 202. At this time, the imaging section 3 images the work W. In this way, four luminance images can be obtained. Note that the number of illuminations is not limited to four and can be set to any number as long as the number of illuminations is three or more and the work W can be illuminated from directions different from one another.

The normal vector calculating section 402 calculates normal vectors with respect to the surface of the work W of pixels using a pixel value of each of pixels in a correspondence relation among a plurality of luminance images captured by the imaging section 3. The contour image generating section 403 applies differential processing in the X direction and the Y direction on the calculated normal vectors of the pixels and generates a contour image showing a contour of a tilt of the surface of the work W. The texture visualized image generating section 404 calculates albedos of the pixels as many as the normal vectors from the calculated normal vectors of the pixels and generates, from the albedos, a texture visualized image showing a pattern obtained by removing a tilt state of the surface of the work W.

Figure 38:
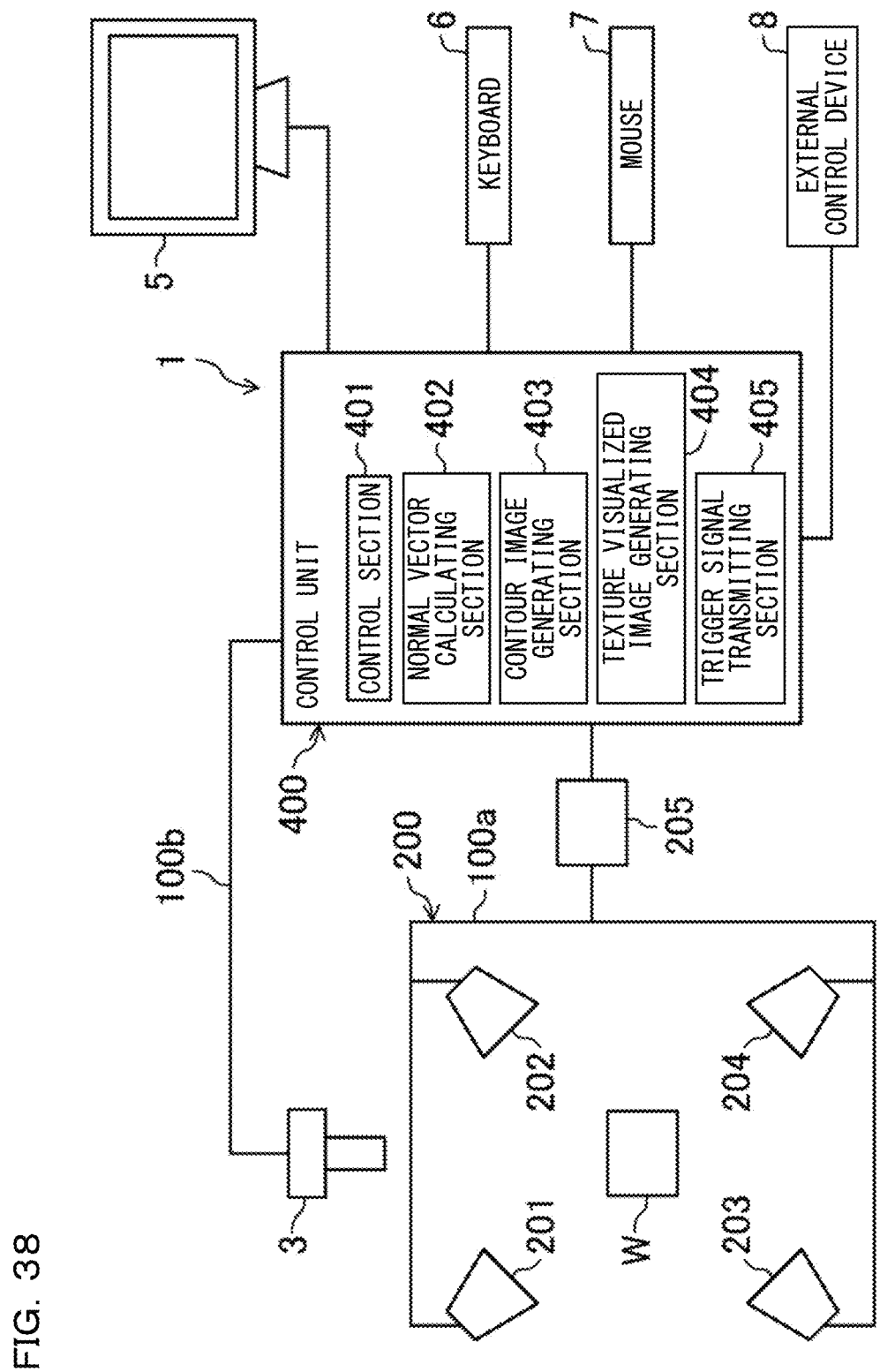
FIG. 38 is a block diagram of an image inspection apparatus according to a second embodiment.

Note that, although not shown in FIG. 38, in the second embodiment, as in the first embodiment, the image inspection apparatus 1 includes a receiving section capable of receiving, for images for inspection displayed on the display section 5, designation of a position of a non-defective portion or a defective portion of an inspection target object in the images for inspection and a setting section that sets, on the basis of a pixel value of the position of the non-defective portion or the defective portion received by the receiving section, for a plurality of images for inspection, a pixel value range that should be set as the non-defective portion. Further, the image inspection apparatus 1 includes an operation receiving section capable of receiving enlarging operation for designating and enlarging a part of a region of one image for inspection among the images for inspection displayed on the display section 5 and a display control section that enlarges, in the other images for inspection displayed on the display section 5, at the same magnification in association with the enlarging operation, a region corresponding to the region designated in the one image for inspection and causes the display section 5 to display the region. It goes without saying that reducing operation and scroll operation are possible instead of the enlarging operation. Furthermore, a not-shown filter processing section is the same as the filter processing section in the first embodiment.

Action and Effects of the Embodiment

According to the second embodiment, it is possible to obtain, using the photometric stereo method, a plurality of images for inspection in which detection of defects of different types can be detected. It is possible to perform a defect inspection using the obtained images for inspection.

Third Embodiment

Figure 39:
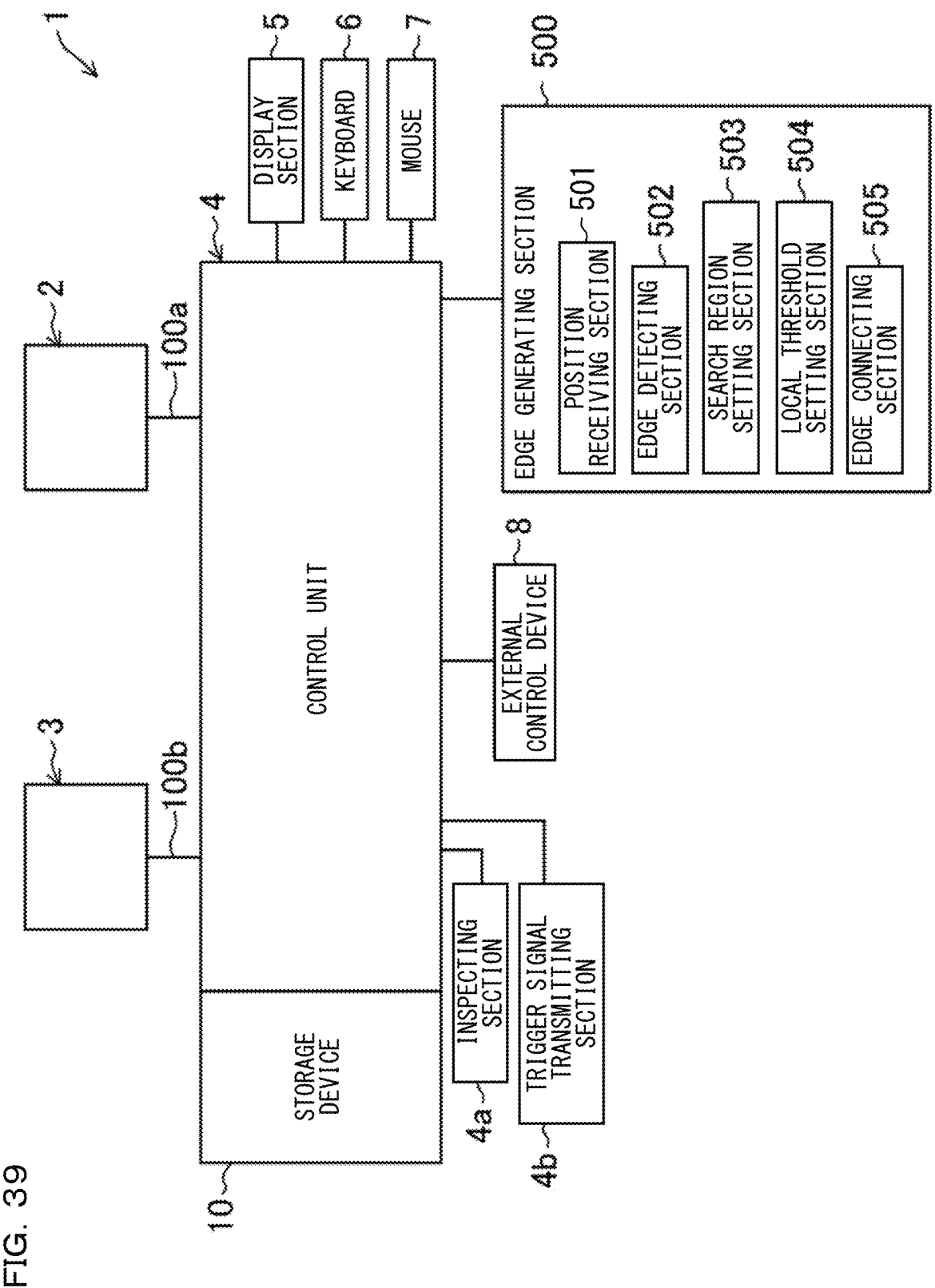
FIG. 39 is a block diagram of an image inspection apparatus according to a third embodiment.

FIG. 39 is a block diagram of the image inspection apparatus 1 according to a third embodiment of the present invention. The third embodiment is different from the first embodiment in that the image inspection apparatus 1 includes an edge generating section 500. However, the other sections are the same as the sections in the first embodiment. Therefore, the same sections as the sections in the first embodiment are denoted by the same reference numerals and signs and explanation of the sections is omitted. The different sections are explained in detail.

When inspection of the work W is performed, for example, a user sometimes desires to perform a defect inspection of a contour having a complicated shape or perform a defect inspection in a specific region having a complicated shape. In such a case, a contour needs to be accurately extracted on an image for inspection. The edge generating section 500 is a section for generating a contour of the work W on a screen displayed on the display section 5. The edge generating section 500 can be apart of the control unit 4.

Note that the contour of the work W is also referred to as edge. However, the edge is not limited to an exterior line of the work W and is sometimes a circumferential edge portion of a hole or a recess formed in the work W, an edge of a groove formed in the work W, an exterior line of a bead provided in the work W, an exterior line of a seal member provided in the work W, and an edge portion of a seal agent applied to the work W, and the like. In this embodiment, basically, it is possible to generate any edge on a screen and confirm the edge.

The edge generating section 500 includes a position receiving section 501 that receives, on an image for inspection displayed on the display section 5, designation of any position serving as an initial position of edge detection of the work W, an edge detecting section 502 that detects the initial position received by the position receiving section 501 or an initial edge position near the initial position and specifies a gradient direction of the edge, a search region setting section 503 that assumes a direction substantially orthogonal to the gradient direction of the edge detected by the edge detecting section 502 as an edge tangential direction and sets a search region, which is a region where an edge is searched, in a position apart from the detected edge by a predetermined distance in the edge tangential direction, a local threshold setting section 504 for setting an effective local threshold for edge position detection in the search region on the basis of a pixel value in the search region set by the search region setting section 503, and an edge connecting section 505.

The edge detecting section 502 is configured to detect an edge position in the search region on the basis of the pixel value in the search region and the local threshold value for edge position detection, execute edge detection processing for specifying the gradient direction of the edge, and repeatedly execute the edge detection processing for search regions sequentially set by the search region setting section 503. The edge connecting section 505 is configured to execute connection processing for connecting edge positions sequentially detected in the search regions to thereby specify a contour of the work W.

Note that, in this embodiment, the edge detecting section 502 detects an edge position and specifies a gradient direction of the edge. However, this is processing for assuming an edge tangential direction. When the edge tangential direction is assumed without specifying the gradient direction of the edge, it is unnecessary to specify the gradient direction of the edge.

Figure 40:
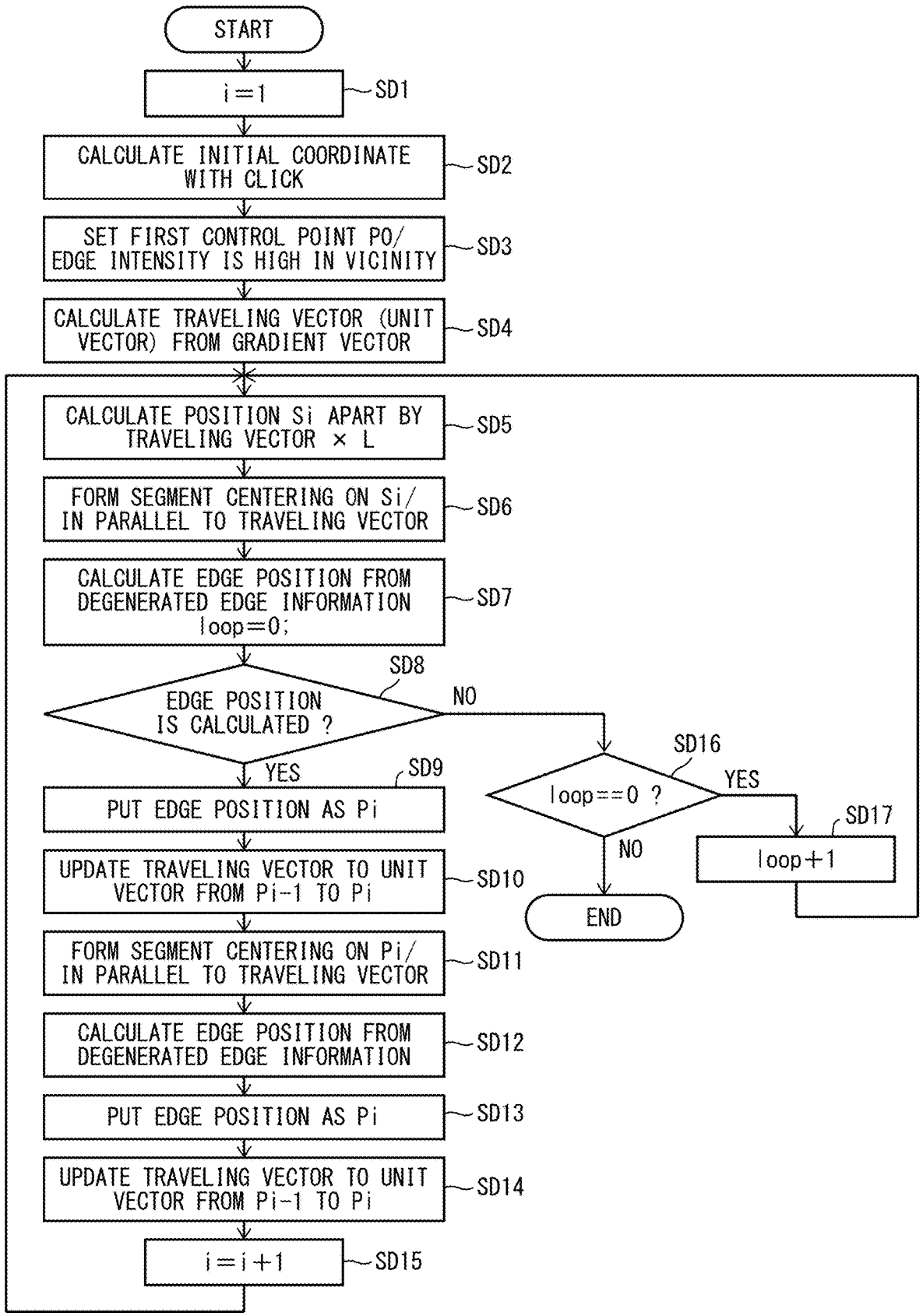
FIG. 40 is a flowchart showing an edge generating method.

A specific edge generating method by the edge generating section 500 is explained below with reference to a flowchart of FIG. 40. In first step SD1 of the flowchart, the edge generating section 500 puts i=1. Thereafter, the edge generating section 500 proceeds to step SD2. In step SD2, a user designates, on an image for inspection displayed on the display section 5, with click operation of the mouse 7, any position serving as an initial position of edge detection of the work W. A designation method for the initial position is not limited to the operation of the mouse 7 and may be operation of other input devices.

Figure 41:
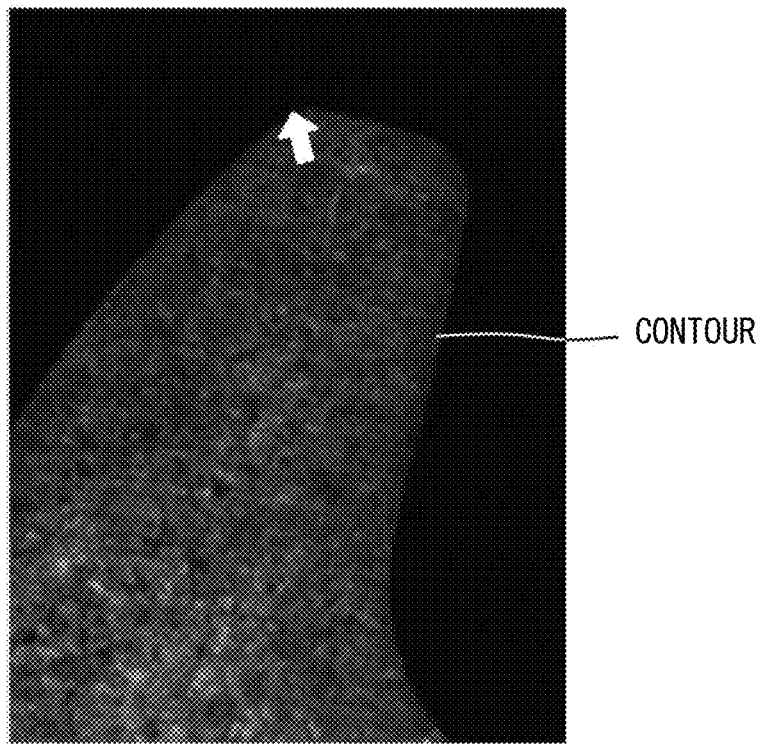
FIG. 41 is an image for inspection showing a state in which a pointer is placed on an edge.

For example, on an image for inspection shown in FIG. 41, the user places a pointer (indicated by a white arrow) on a line recognized as an edge and performs click operation of the mouse 7. Since the user is considered to designate a portion, an edge of which is easily seen, on the image for inspection, it is possible to accurately specify an initial position by causing the user to point at the initial position.

Figure 42:
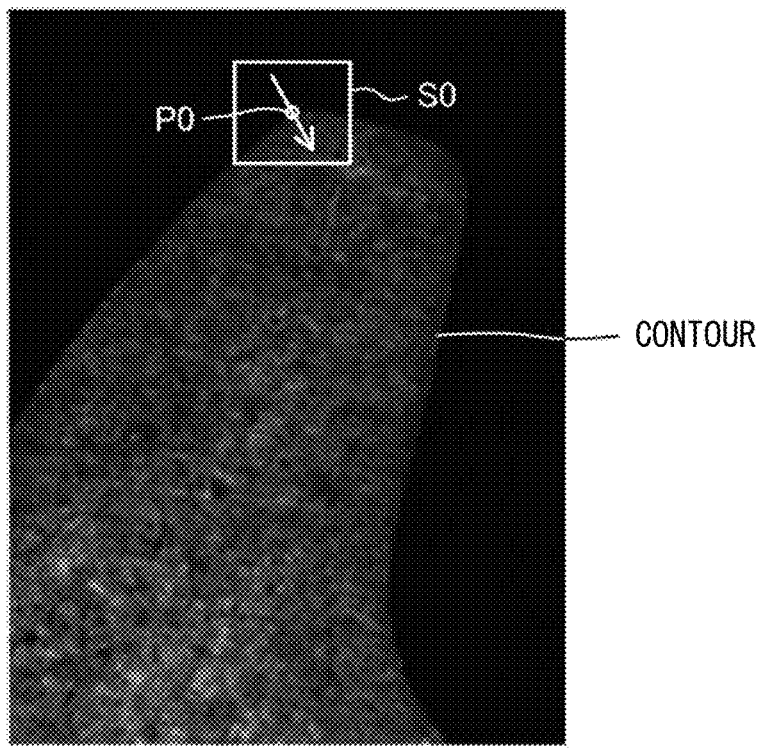
FIG. 42 is an image for inspection showing a state in which an initial coordinate is displayed.

A clicked position is received by the position receiving section 501. Since the clicked position sometimes slightly deviates from the edge, the edge detecting section 502 calculates a coordinate having largest edge intensity, that is, a coordinate of a portion where a difference in a pixel value is large in a region S0 in a predetermined range including the clicked position as shown in FIG. 42, calculates a coordinate corresponding to the position of the coordinate, and sets the coordinate as an initial coordinate P0 (step SD3). Consequently, even if the clicked position slightly deviates from the edge, it is possible to correct the position and place the initial coordinate on the edge. In step SD3, a gradient direction (a direction in which a pixel value changes) of the edge is also specified. As shown on the left side of FIG. 43, a gradient vector n passing the initial coordinate P0 and indicating the gradient direction of the edge is calculated. This is performed by the edge detecting section 502. Note that, if an edge exceeding a threshold is not found, the edge generating section 500 ends the processing.

In step SD4 following step SD3, the edge generating section 500 calculates a tangential vector r (a tangential vector in the initial coordinate P0) substantially orthogonal to the gradient vector n and sets the tangential vector r as a traveling vector (a unit vector). A direction of the traveling vector can be assumed as an edge tangential direction.

Figure 43:
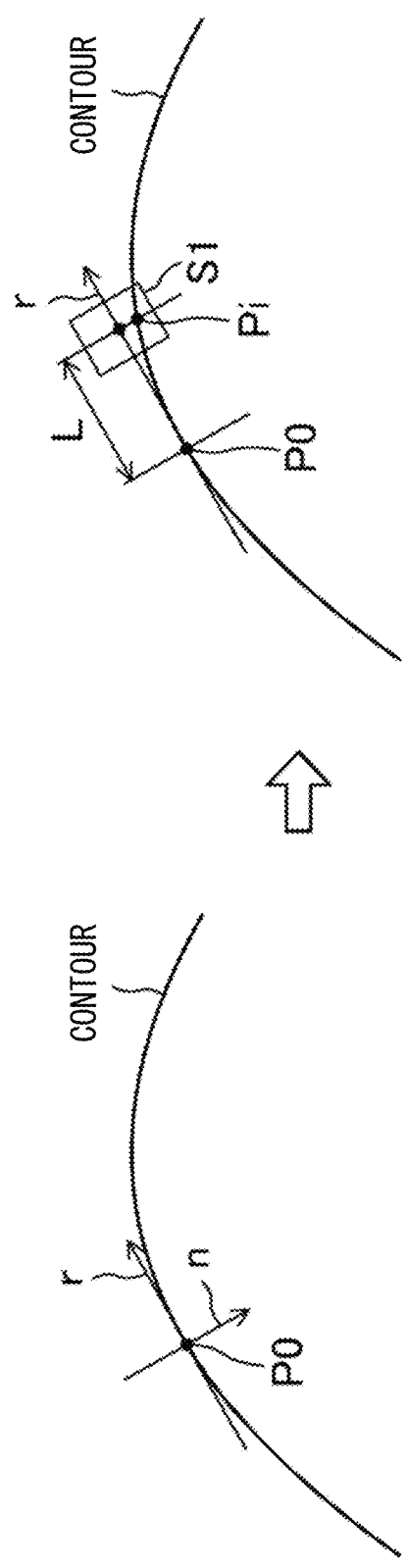
FIG. 43 is a diagram schematically showing a method of forming a segment and calculating an edge position.

Thereafter, the edge generating section 500 proceeds to step SD5 and calculates a coordinate (a point Si) of a position the traveling vector r×L (a predetermined distance) apart as shown on the right side of FIG. 43. In step SD6, the edge generating section 500 forms, in parallel to the traveling vector r, a segment S1 centering on the point Si. The segment S1 is equivalent to a search region, which is a region where an edge is search. This is performed by the search region setting section 503.

Figure 44:
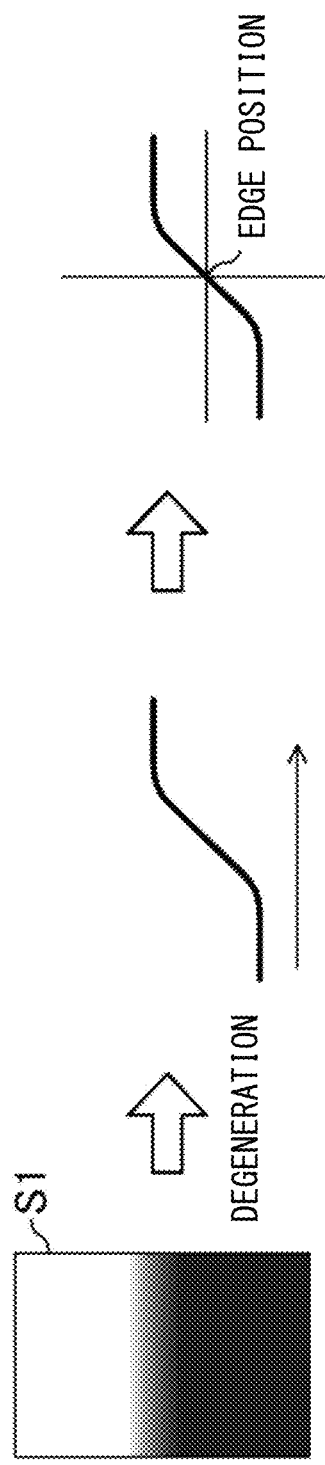
FIG. 44 is a diagram schematically showing a method of projecting a pixel in the segment and calculating an edge position.

After forming the segment S1, in step SD7, the edge generating section 500 projects (degenerates) a pixel in the segment S1 shown on the left side of FIG. 44 in a direction orthogonal to the edge gradient direction to thereby set the pixel to a one-dimensional pixel value as shown in the center of FIG. 44 and obtains the one-dimensional pixel value as edge information. The edge generating section 500 calculates an edge position from the obtained edge information.

Since this is binarization in the segment S1, it is possible to determine a threshold of the binarization in a narrow region. The threshold calculated in the segment S1 is a local threshold for edge position detection. The local threshold for edge position detection can be calculated by an OTSU law (a discrimination analysis law). This is performed by the local threshold setting section 504. For example, the local threshold for edge position detection may be set with respect to a differential value of the one-dimensional pixel value to calculate an edge position.

In step SD8, the edge generating section 500 determines whether the edge position is calculated. When it is determined NO in step SD8, the edge generating section 500 returns to step SD5 through steps SD16 and SD17. When the edge position is not calculated even if the calculation is attempted a plurality of times, the edge generating section 500 ends the processing.

On the other hand, when it is determined YES in step SD8 and the edge position is calculated, the edge generating section 500 proceeds to step SD9 and puts the calculated edge position as Pi as shown on the right side of FIG. 43. In step SD10, the edge generating section 500 updates the traveling vector to a unit vector from Pi−1 to Pi.

Thereafter, in step SD11, the edge generating section 500 forms, in parallel to the traveling vector, a segment centering on the point Pi calculated in step SD9. In step SD12, the edge generating section 500 degenerates the segment formed in step SD11 to thereby binarize the segment, obtains edge information, and calculates an edge position from the edge information. In step SD13, the edge generating section 500 puts the edge position calculated in step SD12 as Pi. In step SD14, the edge generating section 500 updates the traveling vector to a unit vector from Pi−1 to Pi. In step SD15, the edge generating section 500 puts i=i+1. Thereafter, the edge generating section 500 proceeds to step SD5.

Figure 45A:
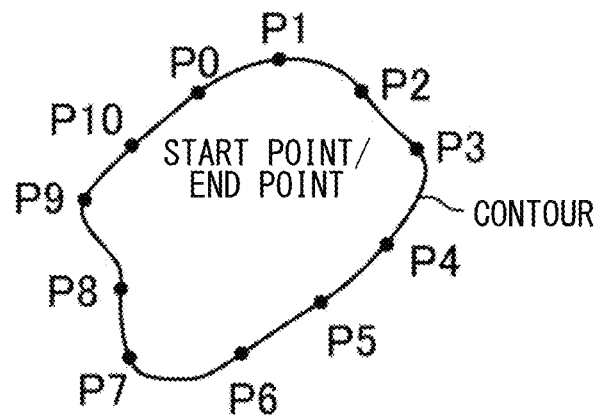
FIG. 45A is a diagram showing a state in which connection processing is executed to specify a contour.

That is, by repeatedly executing the edge detection processing on the sequentially-set search regions, as shown in FIG. 45A, it is possible to calculate a plurality of edge positions (in this example, points P0 to P10). After the plurality of edge positions are calculated, the edge connecting section 505 can specify a contour of the work W by connecting the edge positions with lines in the order of calculation (P0→P1→P2 P10→P0). At this time, a method of determining whether the distance between P0 and P10 is equal to or smaller than a predetermined distance and, if the distance is equal to or smaller than the predetermined distance, connecting P0 and P10 may be adopted.

When P10 is connected to P0, a closed region flag can be set up to end the processing. P0 is a start point and an end point of the contour. Some contour is not a closed region. The contour of the work W specified in this way can be displayed in any color other than white and black in a state in which the contour is combined with a screen for inspection.

Figure 45B:
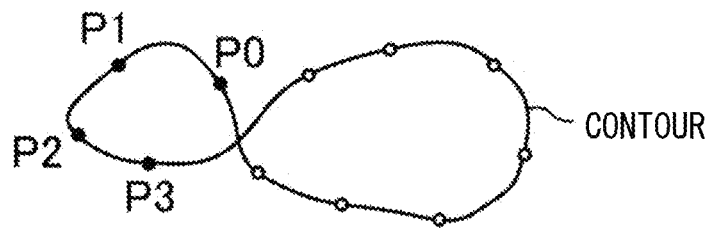
FIG. 45B is a diagram showing a connection processing method performed when two contours are close.

In FIG. 45B, a contour is already specified by white dots (edge positions). Thereafter, P0 to P3 are calculated in order as edge positions. After P3 is calculated, it is desirable to stop the processing to prevent a contour from crossing the already specified contour. After P3 is calculated, P3 may be connected to P0 rather than a white dot to end the processing. Consequently, it is possible to avoid straying. The contour may be a closed region formed by only edge positions indicated by white dots in FIG. 45B. Note that the white dots on the drawing are only shown to achieve convenience of explanation. Colors and forms can be optionally set. However, it is desirable that already calculated edge positions and edge positions calculated thereafter are displayed in different colors and forms.

Figure 45C:
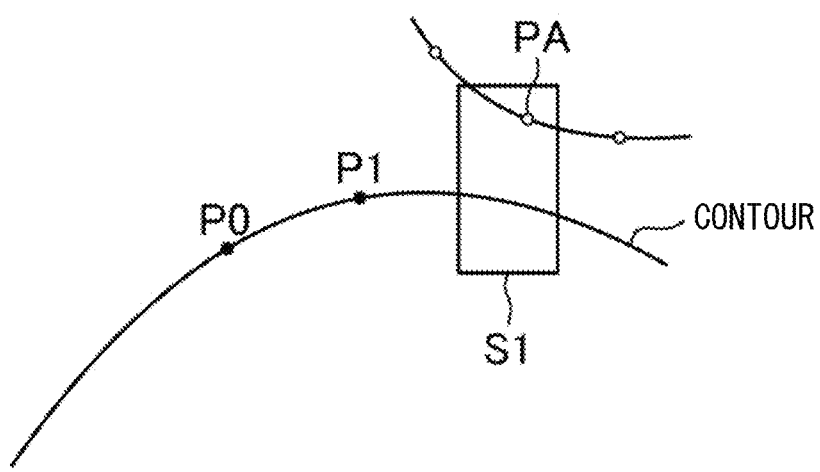
FIG. 45C is a diagram showing another connection processing method performed when two contours are close.

In FIG. 45C, a contour is already specified by white dots (edge positions). Thereafter, P0 and P1 are calculated as edge positions. When an already specified contour is present in a segment S1 formed after P1 is calculated, the processing can be stopped. Note that, if P0 is present in the segment S1, P1 only has to be connected to P0 without stopping the processing.

Figure 46:
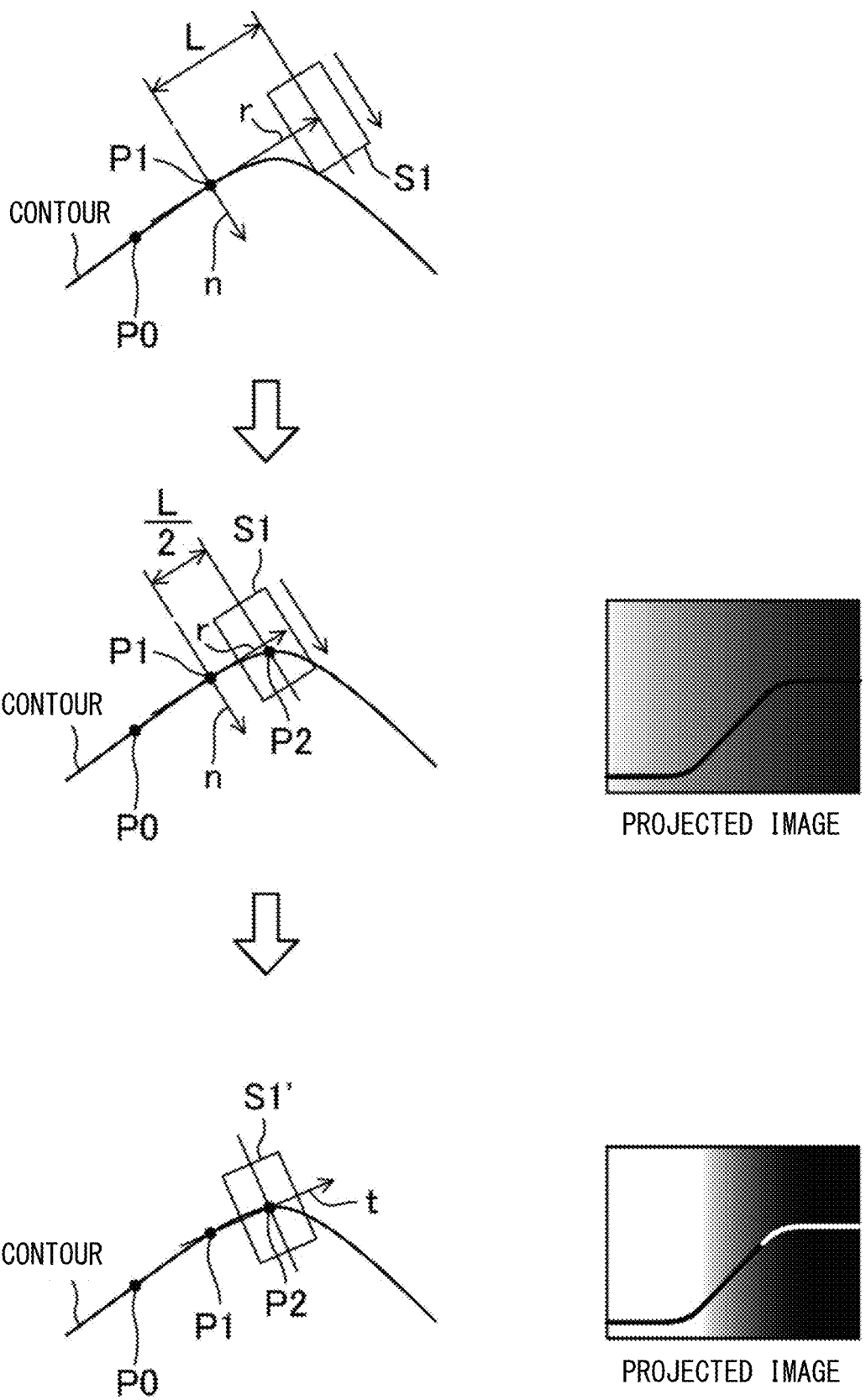
FIG. 46 is a diagram showing a processing method performed when a curvature of a contour is small.

FIG. 46 is a figure showing a processing method performed when a curvature of a contour is small. As shown in an upper part of FIG. 46, after the edge position P1 is calculated, in order to calculate the next edge position, the segment S1 is formed in a place apart from the edge position 21 by a predetermined distance L in the traveling vector direction. At this time, if a curvature of a contour is small, the contour is located outside the segment S1. An edge position sometimes cannot be detected.

The search region setting section 503 is configured to, when an edge position cannot be detected in the segment S1 in this way, reduce the predetermined distance L and reset the segment S1. As shown in the second figure from the top in FIG. 46, the predetermined distance L can be reduced to, for example, L/2. The edge detecting section 502 detects an edge position in the segment S1 reset by reducing the predetermined distance L and specifies a gradient direction of the edge. Note that, when an edge cannot be detected even if the predetermined distance L is reduced to L/2, the predetermined distance L is further reduced to form the segment S1.

In the second figure from the top in FIG. 46, when a pixel in the segment S1 is projected, since the pixel is projected obliquely to the contour, the edge is blurred. It is sometimes difficult to see an accurate edge. In this respect, as shown in a lower part of FIG. 46, the edge detecting section 502 sets, as a provisional edge position P2, an edge position detected in the segment S1 reset by the search region setting section 503. The search region setting section 503 sets a segment S1' (a reset search region) spreading in a direction orthogonal to a vector t that connects the provisional edge position P2 and the edge position P1 detected immediately before the provisional edge position P2. Consequently, the edge is clarified when a pixel in the segment S1' is projected. The edge detecting section 502 is configured to detect an edge position in the segment S1', specify a gradient direction of the edge, and replace the provisional edge position P2 with the detected edge position.

Figure 47:
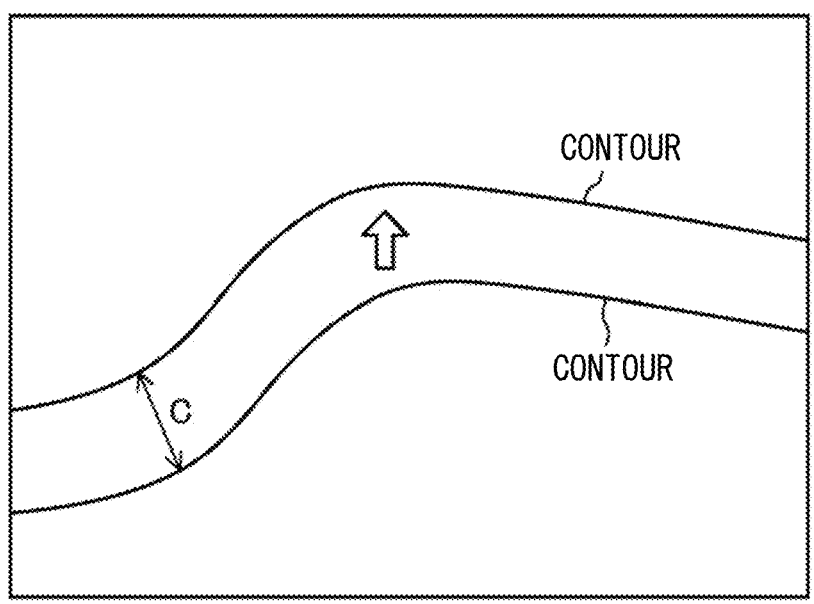

In an inspection target object shown in FIG. 47, for example, a bead, a seal agent, or an O ring, the inspection target object has a predetermined width C. Contours are respectively present on both sides in the width direction. In this embodiment, the contours on both the sides in the width direction can also be specified by applying the method explained above. A method of specifying the contours on both the sides is explained in detail below with reference to a flowchart of FIG. 48.

Figure 48:
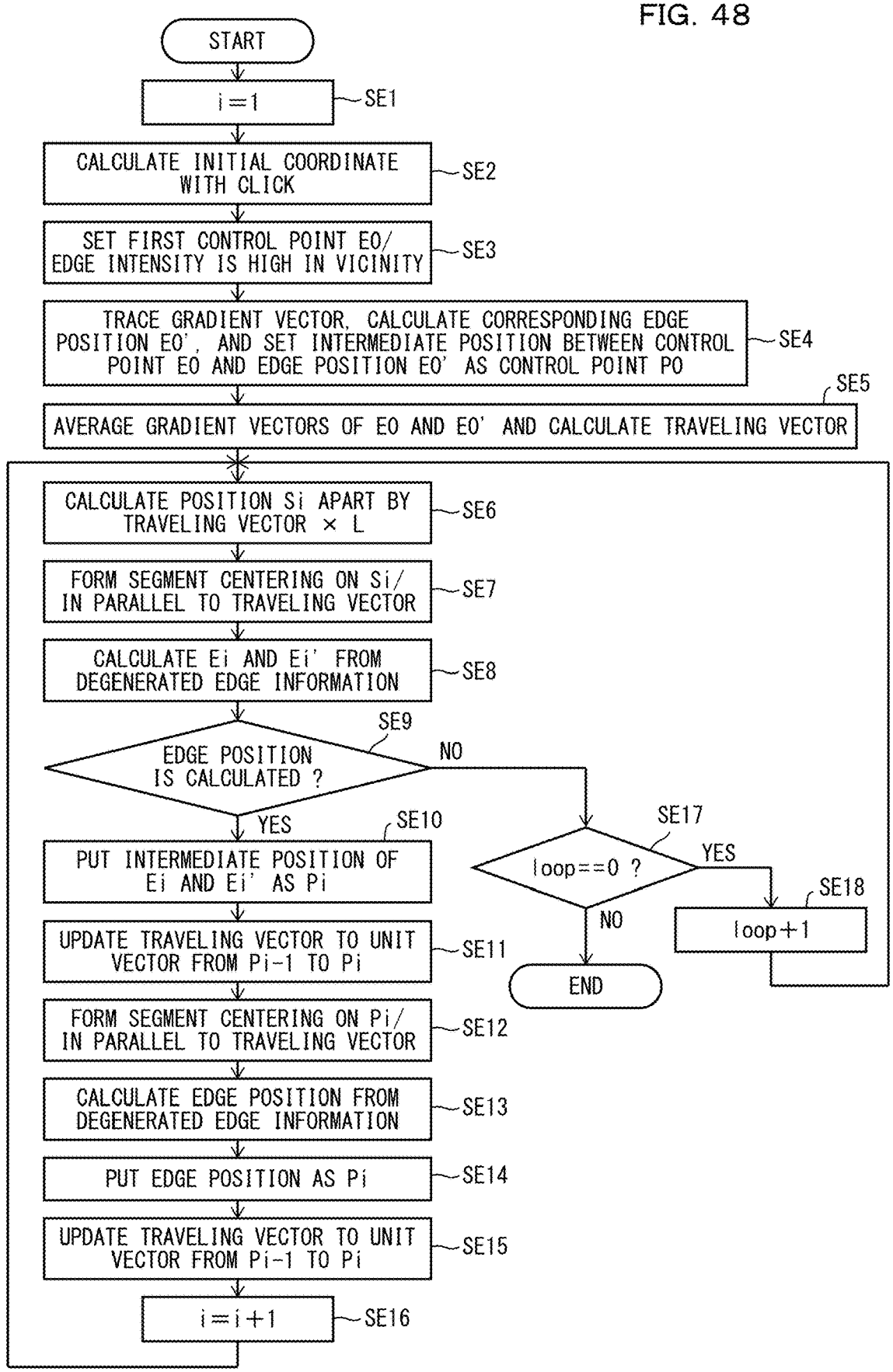
FIG. 48 is a flowchart showing a method of specifying contours on both sides.

In step SE1 of the flowchart of FIG. 48, the edge generating section 500 puts i=1. Thereafter, the edge generating section 500 proceeds to step SE2. In step SE2, the user designates, with click operation of the mouse 7, any position serving as an initial position of edge detection of the inspection target object on an image for inspection displayed on the display section 5. For example, on an image for inspection (a part of which is shown) shown in FIG. 47, the user places a pointer (indicated by a white arrow) in a place recognized as the width direction center of the inspection target object and performs the click operation of the mouse 7. A clicked position is received by the position receiving section 501.

Figure 49:
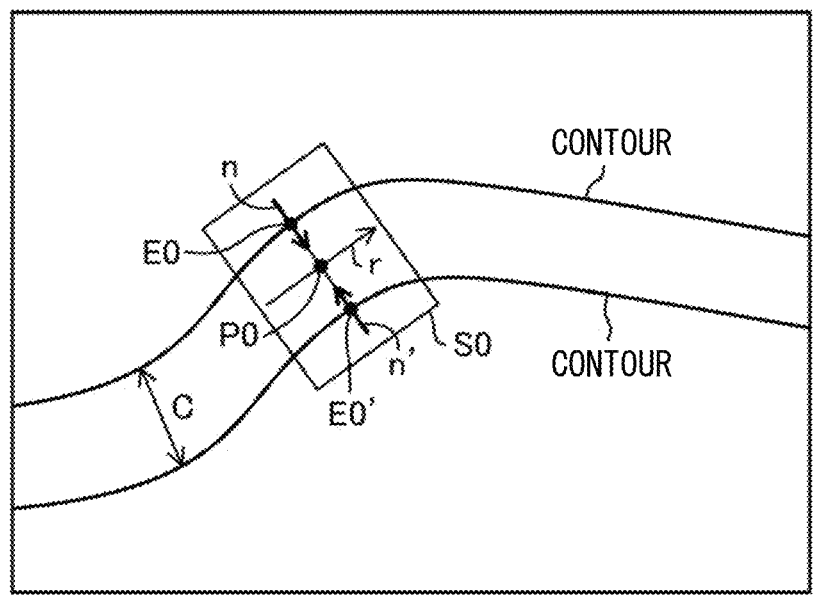
FIG. 49 is a diagram schematically showing a method of calculating a control point P0 in the method of specifying contours on both sides.

In step SE3, the edge generating section 500 calculates a coordinate where edge intensity is high in a region S0 (shown in FIG. 49) in a predetermined range including the clicked position and sets a first edge position E0. In step SE4, the edge generating section 500 traces the gradient vector n and calculates an edge position E0' corresponding to the edge position E0. The direction of a gradient vector n' in the edge position E0' is opposite to the direction of the gradient vector n. An intermediate position between the edge position E0 and the edge position E0' is set as an initial coordinate (a control point) P0.

Figure 50:
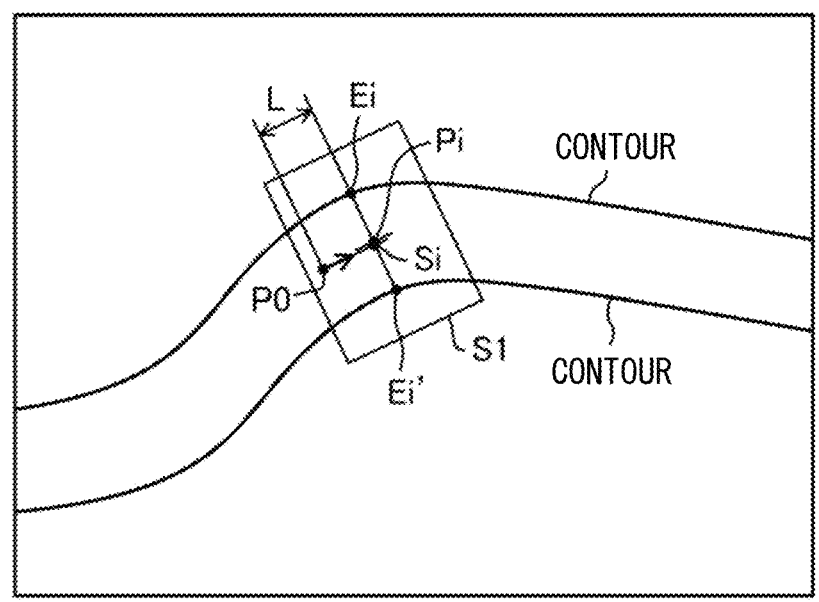
FIG. 50 is a diagram schematically showing a method of forming a segment and calculating an edge position in the method of specifying contours on both sides.

In step SE5, the edge generating section 500 averages the gradient vector n in the edge position E0 and the gradient vector n' in the edge position E0' to calculate the traveling vector r. In step SE6, as shown in FIG. 50, the edge generating section 500 calculates a coordinate (the point Si) in a position the traveling vector r×L (the predetermined distance) apart. In step SE7, the edge generating section 500 forms, in parallel to the traveling vector r, the segment S1 centering on the point Si.

In step SE8, the edge generating section 500 projects (degenerates) a pixel in the segment S1 in a direction orthogonal to the edge gradient direction to thereby obtain a one-dimensional pixel value as edge information and calculates edge positions Ei and Ei' from the edge information. In step SE9, the edge generating section 500 determines whether the edge positions are calculated. When it is determined NO in step SE9, the edge generating section 500 returns to step SE6 through steps SE17 and SE18. When the edge positions are not calculated even if the calculation is attempted a plurality of times, the edge generating section 500 ends the processing.

On the other hand, when it is determined YES in step SE9 and the edge positions Ei and Ei' are calculated, the edge generating section 500 proceeds to step SE10 and puts an intermediate position of the edge positions Ei and Ei' as Pi. In step SE11, the edge generating section 500 updates the traveling vector to a unit vector from Pi−1 to Pi. Thereafter, in step SE12, the edge generating section 500 forms, in parallel to the traveling vector, a segment centering on the point Pi calculated in step SE10. In step SE13, the edge generating section 500 degenerates the segment formed in step SE12 to thereby binarize the segment, obtains edge information, and calculates an edge position from the edge information. In step SE14, the edge generating section 500 puts the edge position calculated in step SE13 as Pi. In step SE15, the edge generating section 500 updates the traveling vector to a unit vector from Pi−1 to Pi. In step SE16, the edge generating section 500 puts i=i+1. Thereafter, the edge generating section 500 proceeds to step SE6. Therefore, by repeatedly executing, on the width direction both sides of the inspection target object, the edge detection processing on sequentially set search regions, it is possible to calculate pluralities of edge positions respectively on both the sides. After the edge positions are calculated, the edge connecting section 505 can specify contours on both the sides by connecting the edge positions with lines.

The generation of an edge can be performed during setting of the image inspection apparatus 1. The generated edge can be stored in the storage device 10 as a reference model line. After the setting of the image inspection apparatus 1, during the operation of the image inspection apparatus 1, an inspection target object is imaged to obtain an image for inspection. After position correction and the like of the inspection target object in the image for inspection are performed, an edge of the inspection target object on the image for inspection is detected. When the edge and the reference model line are compared and, when a difference between the edge and the reference model line is equal to or larger than a predetermined value, it can be specified that the edge is a defective portion. This can be executed by the inspecting section 4a.

Action and Effects of the Embodiment

According to the third embodiment, when the user designates an edge of the work W or a position near the edge on the image for inspection displayed on the display section 5, setting of a search region, setting of a threshold in the search region, and detection of an edge position in the search region are repeatedly performed. A plurality of edge positions can be sequentially obtained along the contour of the work W. The contour of the work W can be automatically specified by connecting the obtained edge positions. Therefore, it is possible to highly accurately specify the contour even with simple operation. It is possible to improve detection accuracy.

Fourth Embodiment

Figure 51:
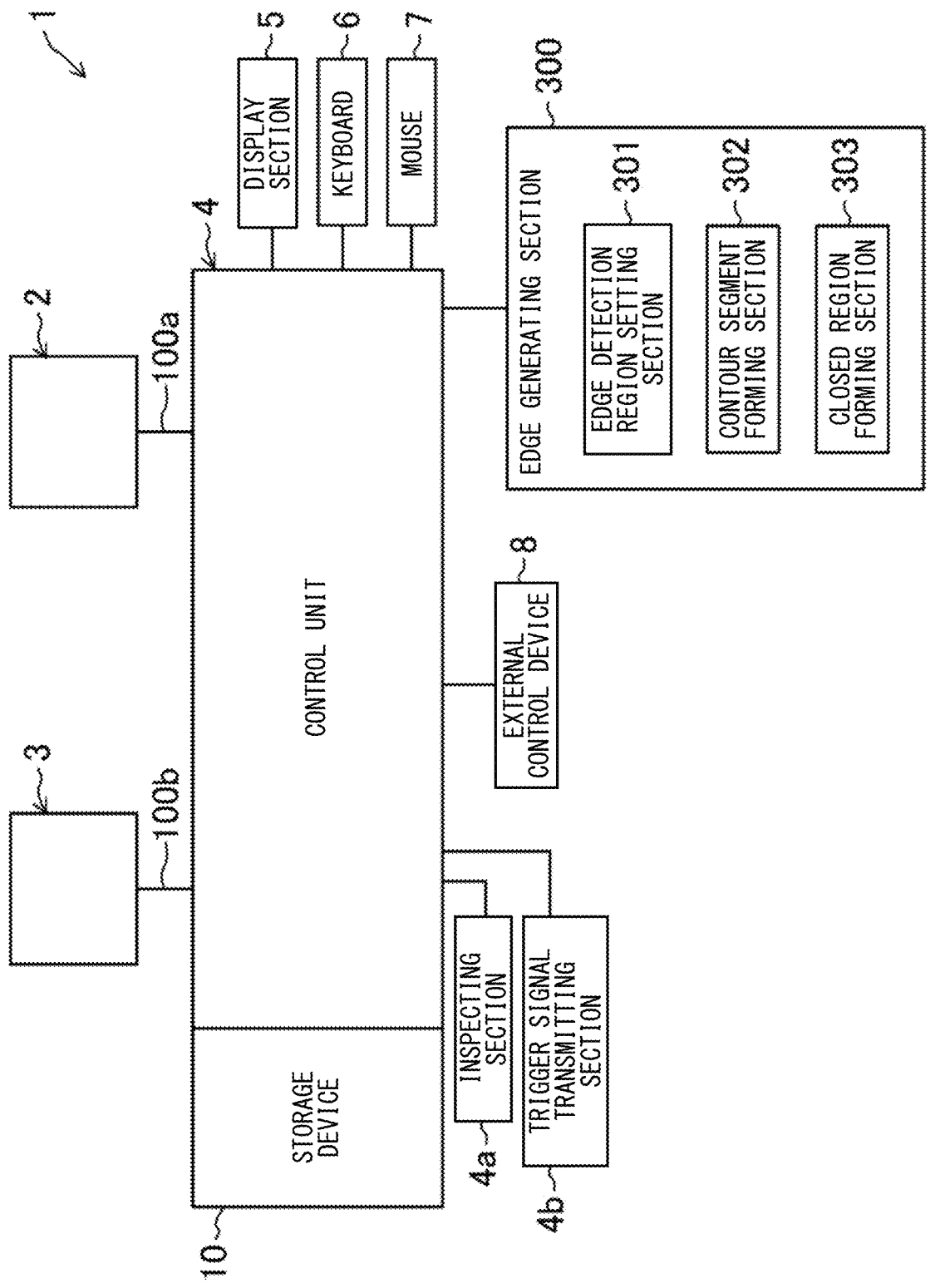
FIG. 51 is a block diagram of an image inspection apparatus according to a fourth embodiment.

FIG. 51 is a block diagram of the image inspection apparatus 1 according to a fourth embodiment of the present invention. The fourth embodiment is different from the first embodiment in that the image inspection apparatus 1 includes an edge generating section 300. However, the other sections are the same as the sections in the first embodiment. Therefore, the same sections as the sections in the first embodiment are denoted by the same reference numerals and signs and explanation of the sections is omitted. Different sections are explained in detail.

The edge generating section 300 includes an edge detection region setting section 301 for setting a plurality of edge detection regions in different positions on an image for inspection displayed on the display section 5, a contour segment forming section 302 that detects a plurality of edge points in the edge detection regions and connects the edge points adjacent to one another to thereby form, for each of the edge detection regions, a contour segment configuring a part of a contour of an inspection target object, and a closed region forming section 303 that executes connection processing for connecting an end portion of one contour segment formed by the contour segment forming section 302 and an end portion of another contour segment closest to the end portion, repeats the connection processing until an open end of the contour segment disappears, and forms a closed region.

Figure 52:
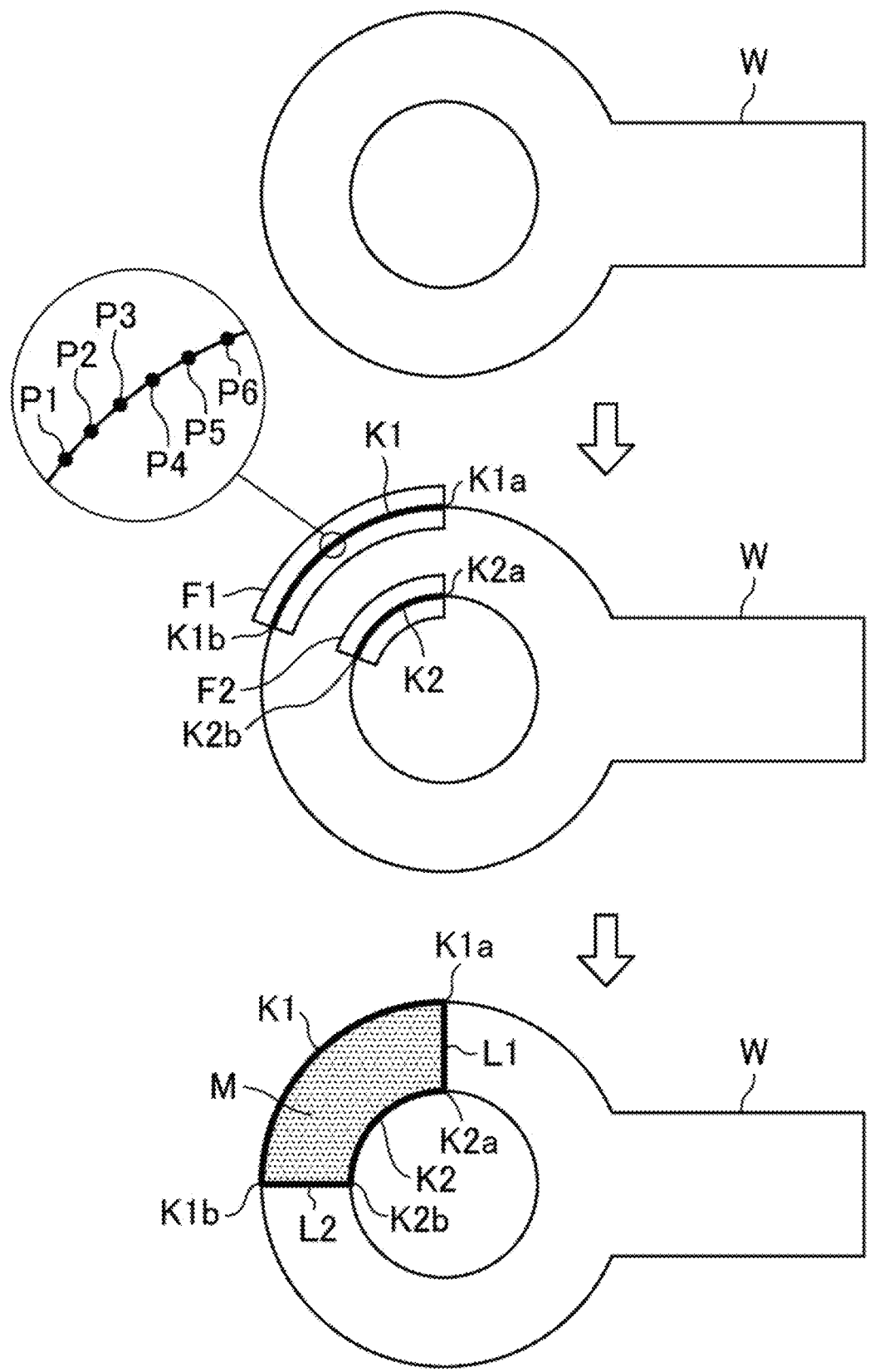
FIG. 52 is a diagram for explaining a procedure for setting a part of work as an inspection target region.

That is, the upper side of FIG. 52 shows an image for inspection obtained by imaging the work W. A user sets edge detection regions F1 and F2 in different positions on the image for inspection as shown in the center of FIG. 52 while viewing the image for inspection. The edge detection regions F1 and F2 can be formed by, for example, surrounding desired portions in the work W with input operation of the mouse 7 or the keyboard 6 by the user. The edge detection region setting section 301 sets, as the edge detection regions F1 and F2, the portions surrounded by the operation.

In the edge detection region F1, as shown in an enlarged part of the figure in the center of FIG. 52, edge points P1, P2, P3, and the like are detected. The edge points can be detected by a well-known method in the past or can be detected by the method explained in the third embodiment. By connecting the edge points adjacent to each other (e.g., P1 and P2), a contour segment K1 configuring a part of the contour of the work W is formed. A contour segment K2 is formed in the edge detection region F2 in the same manner. This is performed by the contour segment forming section 302.

Note that the user may form a contour segment by designating the contour segment using an input device such as the mouse 7. In this case, the user designates at least a start point and an end point of the contour segment by operating the mouse 7 while viewing the image for inspection displayed on the display section 5. The contour segment forming section 302, which receives the designation of the start point and the end point by the user, sets, as a contour segment, a straight line connecting the start point and the end point. In this case, the user may additionally designate an intermediate point between the start point and the end point. The contour segment is not limited to the straight line and can also be formed as a curve by the operation of the mouse 7 or the like.

The closed region forming section 303 connects, with a connection line L1 formed by a straight line, an end portion K1a of the contour segment K1 and an end portion K2a of the contour segment K2 closest to the end portion K1a as shown on the lower side of FIG. 52. The closed region forming section 303 connects, with a connection line L2, an end portion K1b of the contour segment K1 and an end portion K2b of the contour segment K2 closest to the end portion K1b. Consequently, open ends of the contour segments K1 and K2 disappear and a closed region M is formed. The closed region M is an inspection target region and is a region where the inspecting section 4a executes a defect inspection.

A separation distance between the end portion K1a of the contour segment K1 and the end portion K2a of the contour segment K2 set as a target of the connection processing is set longer than an interval between the edge points adjacent to each other (e.g., P1 and P2). Consequently, the end portion K1a of the contour segment K1 and the end portion K2a of the contour segment K2 are less easily misrecognized as edge points.

In the work W shown in FIG. 53, when it is desired to set substantially the entire work W as an inspection target region, as shown on the upper side of FIG. 53, edge detection regions F1 to F6 are formed to surround the peripheral edge portion of the work W. Contour segments K1 to K6 are formed in the edge detection regions F1 to F6.

After the formation of the contour segments K1 to K6, as shown on the lower side of FIG. 53, the end portions of the contour segments K1 to K6 are connected by connecting lines L1 to L6 and the closed region M is formed. In this example, the closed region M can be formed to exclude corner portions of the work W. Therefore, it is possible to form an inspection target region excluding, for example, chamfered portions and R-machined portions of the corner portions of the work W.

In both of the case shown in FIG. 52 and the case shown in FIG. 53, when the contour segments are connected, the contour segments may be connected after all edge detection regions are formed or may be connected in the order of the formation of the edge detection regions. When the contour segments are connected, the connection processing can be prevented from being performed on already connected end portions. The contour segments in a crossing relation with each other can be prevented from being connected to each other. Further, it is also possible to perform connection processing in which connection lines are the shortest. Furthermore, the user may be able to manually select and change end portions to be connected.

The connection processing can be prevented from being performed when a connection line in connecting the contour segments is equal to or larger than a predetermined length. In this case, the contour segments do not forma closed region. The length of the connection line equal to or larger than the predetermined length means that two contour segments are greatly apart from each other. By not performing the connection processing in this case, it is possible to prevent wrong connection processing from being performed. Note that, when the user is capable of manually selecting end portions to be connected, it is desirable to make it possible to connect the end portions even if the length of the connection line exceeds the predetermined length.

The connection line is not limited to the straight line and can be, for example, a quadratic curve, a cubic curve, and the like, in particular, a Bézier curve, a spline curve, and the like. Consequently, it is possible to smoothly connect end portions of the contour segments. The connection line may be a combination of a curve and a straight line. One contour segment and another contour segment can be connected by a curve having a tangential vector common to a tangential vector of an end portion of the one contour segment.

Figure 54:
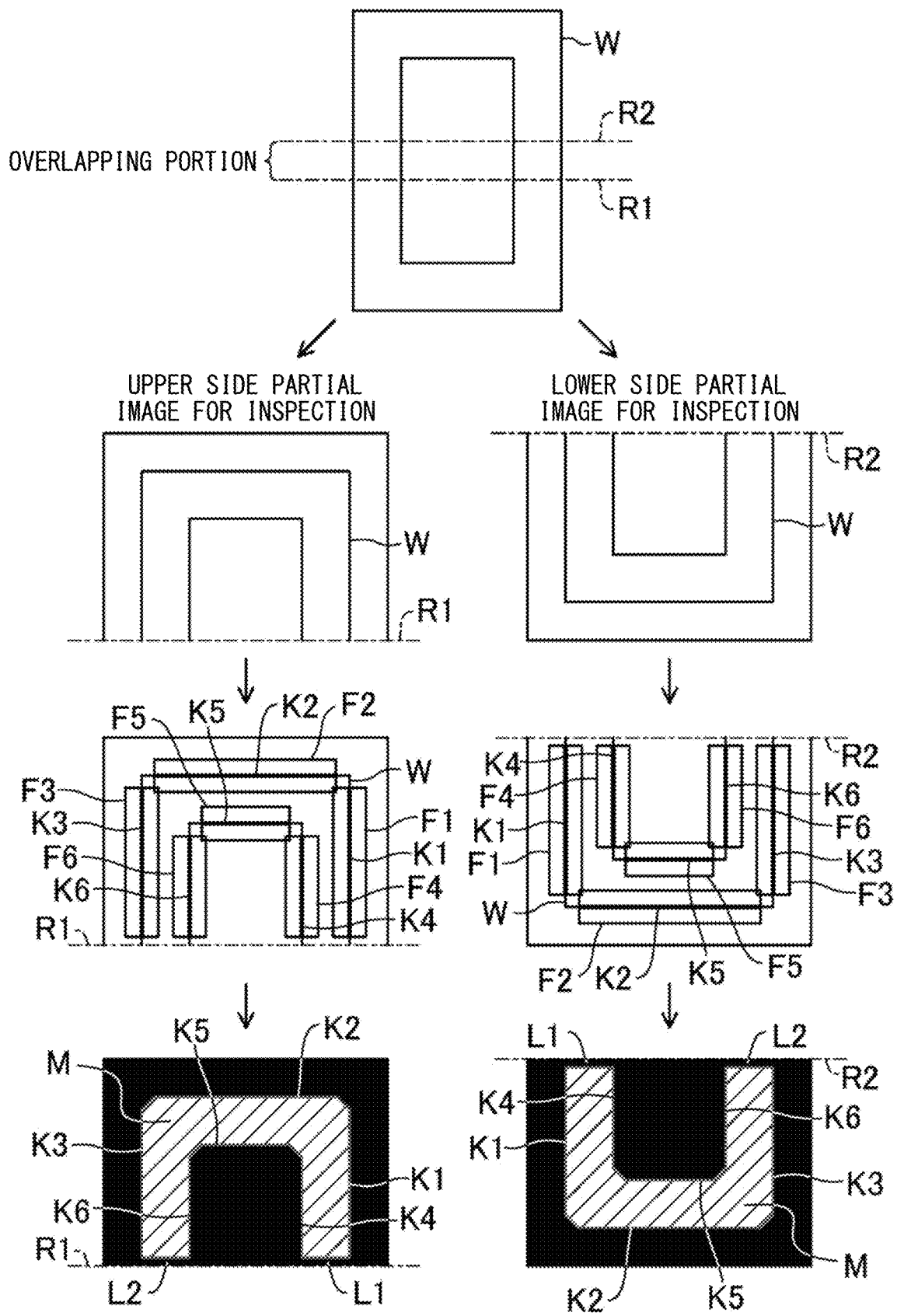
FIG. 54 is a diagram for explaining a procedure for capturing a plurality of partial images for inspection and setting an inspection target region.

FIG. 54 is a diagram for explaining imaging of one work W dividedly performed twice. The imaging section 3 images a portion further on the upper side than an imaging boundary line R1 of the work W to obtain an upper side partial image for inspection (a first partial image for inspection) and images a portion further on the lower side than an imaging boundary line R2 of the work W to obtain a lower side partial image for inspection (a second partial image for inspection). Therefore, a predetermined range between the imaging boundary line R1 and the imaging boundary line R2 in the work W is an overlapping portion included in imaging ranges of both of the upper side partial image for inspection and the lower side partial image for inspection. Note that the setting of the imaging range of the work W is not limited to the example explained above and may be an imaging form for dividing the imaging range in the left-right direction or may be an imaging form for dividing the imaging range into three or more.

In this case, as shown on the left side of FIG. 54, the edge detection regions F1 to F6 are formed in the upper side partial image for inspection. At this time, in the upper side partial image for detection, the work W is present to be in contact with the imaging boundary line R1. However, it is difficult to perform, on the upper side partial image for inspection, operation for extending the lower end portions of the edge detection regions F1, F3, F4, and F6 to nearly come into contact with the imaging boundary line R1. Therefore, when the user performs the operation for extending the lower end portions of the edge detection regions F1, F3, F4, and F6, the user is considered to stop the operation before the lower end portions come into contact with the imaging boundary line R1.

In this respect, in this embodiment, when the lower end portions of the edge detection regions F1, F3, F4, and F6 reach the overlapping portion with the lower side partial image for inspection in the upper side partial image for inspection and the end portions of the contour segments K1, K3, K4, and K6 are located in the overlapping portion, the lower end portion of the contour segment K1 and the lower end portion of the contour segment K4 are connected by the connection line L1 and the lower end portion of the contour segment K3 and the lower end portion of the contour segment K6 are connected by the connection line L2. Consequently, the closed region M can be formed. As shown on the right side of FIG. 54, the same processing can be performed in the lower side partial image for inspection.

That is, when the end portions of a plurality of contour segments (K1, K3, K4, and K6) are located in an overlapping portion with another partial image for inspection (the lower side partial image for inspection) in one partial image for inspection (the upper side partial image for inspection), even if an edge detection region is absent at the end portions of the contour segments, it is possible to automatically perform processing for connecting the end portions of the contour segments with connection lines.

Thereafter, a portion other than the closed region M is blackened and set as non-inspection target region. On the other hand, the closed region M (a hatched region) is whitened and set as an inspection target region. A non-inspection target region and an inspection target region can be set in the same manner in the lower side partial image for inspection. Consequently, even when the work W is dividedly imaged, it is possible to set, with simple operation, as inspection targets, all ranges desired to be inspected.

Action and Effects of the Embodiment

According to the fourth embodiment, when the user sets a plurality of edge detection regions, it is possible to detect pluralities of edge points in the edge detection regions and connect the edge points to form a plurality of contour segments. It is possible to connect the end portions of the contour segments to form a closed region and execute a defect inspection of the work W with the closed region set as an inspection target region.

Other Embodiments

Figure 55:
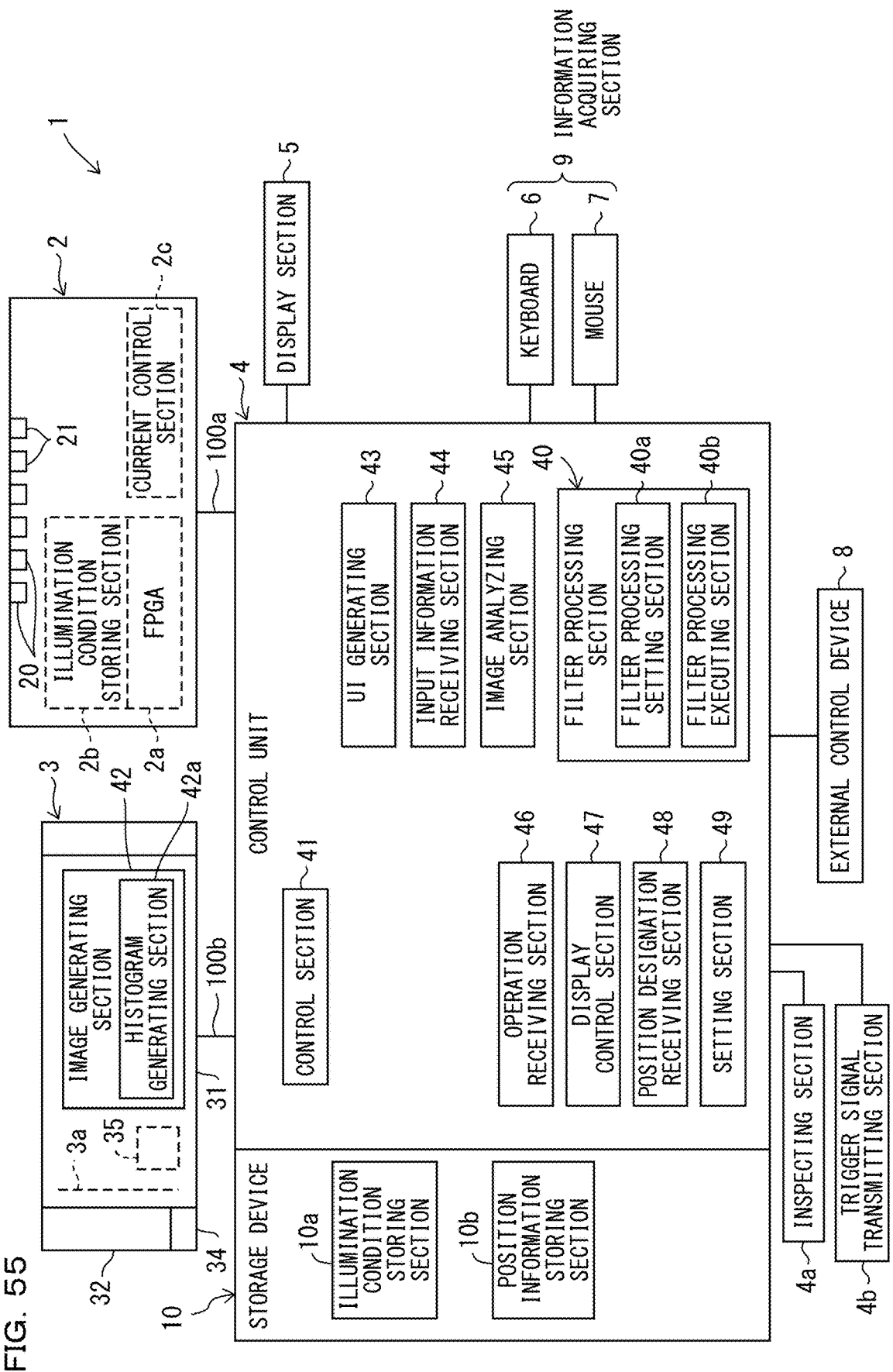
FIG. 55 is a diagram equivalent to FIG. 2 according to a modification 1 of the embodiments.

The present invention is not limited to the first to fourth embodiments. For example, as in a modification 1 shown in FIG. 55, as the configuration of the image inspection apparatus 1, the image generating section 42 can be incorporated in the imaging section 3. Consequently, the imaging section 3 performs the processing up to the creation of an image for inspection by the deflectometry processing. The control unit 4 performs the other processing. That is, the image inspection apparatus 1 can be a smart camera in which an image processing function is imparted to the imaging section 3.

Figure 56:
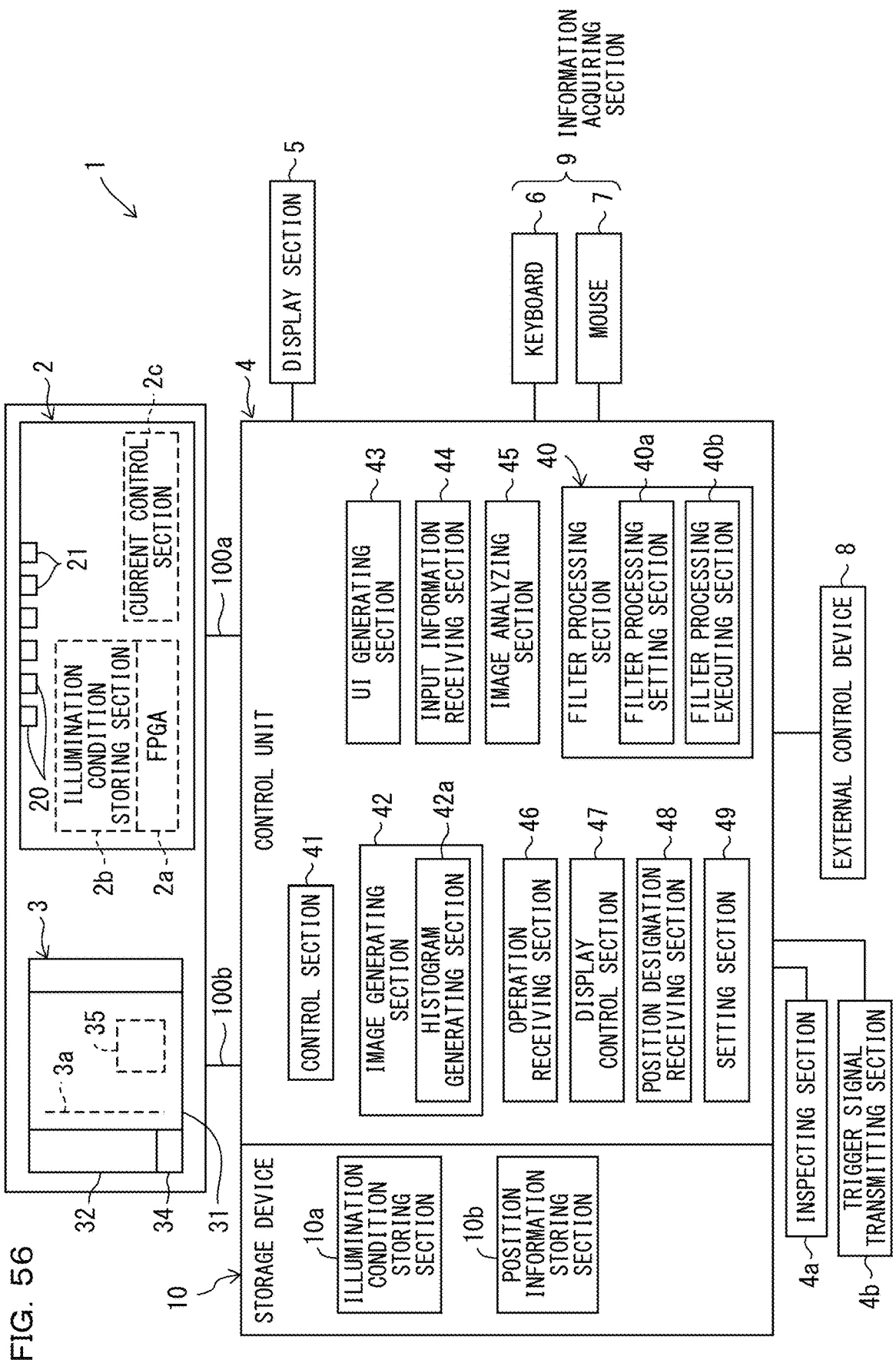
FIG. 56 is a diagram equivalent to FIG. 2 according to a modification 2 of the embodiments.

As in a modification 2 shown in FIG. 56, the pattern light illuminating section 2 and the imaging section 3 can be integrated and the control unit 4 can be separated. In this case, the imaging section 3 can be incorporated in the pattern light illuminating section 2 or the pattern light illuminating section 2 can be incorporated in the imaging section 3.

Figure 57:
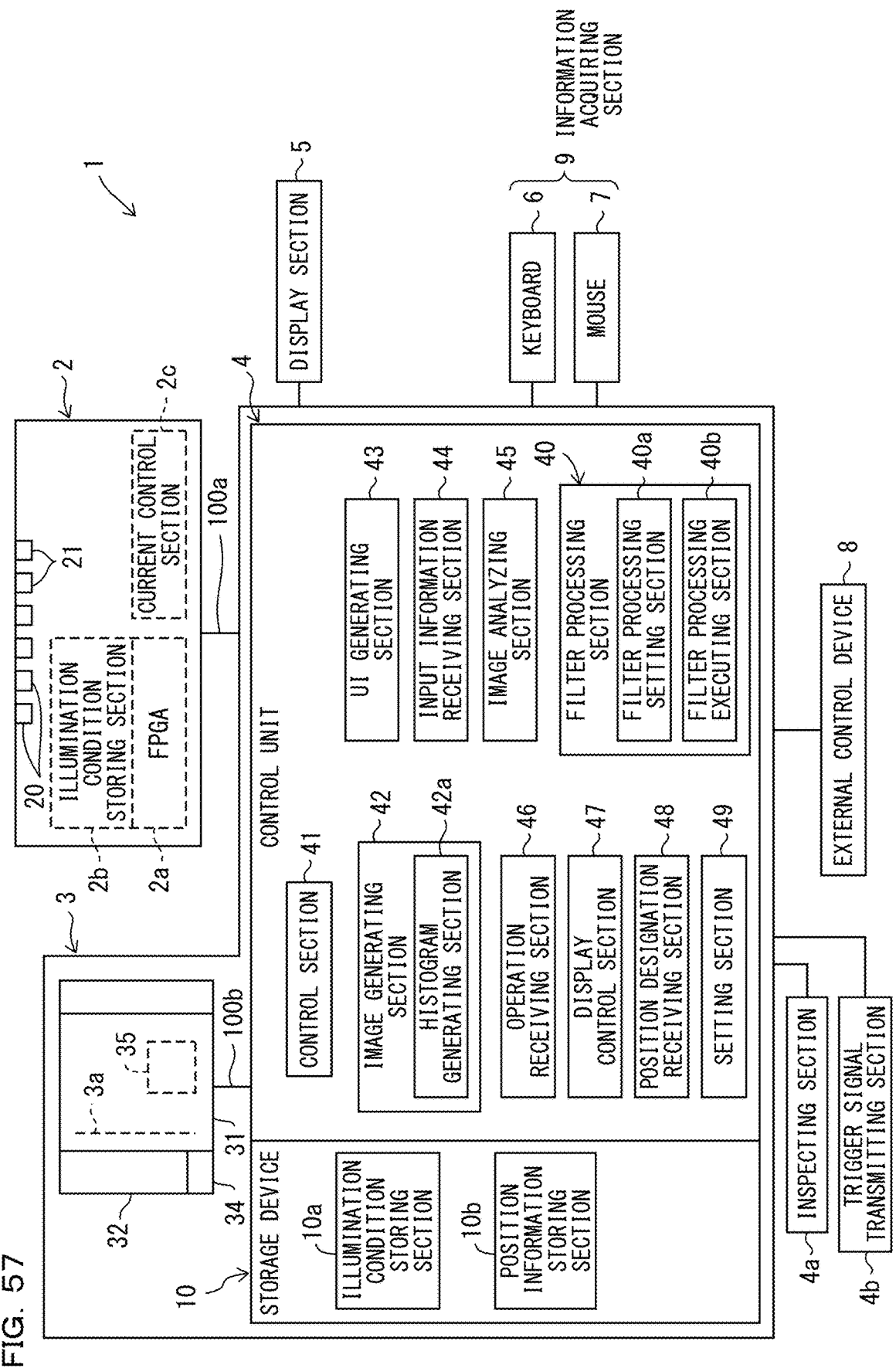
FIG. 57 is a diagram equivalent to FIG. 2 according to a modification 3 of the embodiments.

As in a modification 3 shown in FIG. 57, the imaging section 3 and the control unit 4 can be integrated to incorporate the control unit 4 in the imaging section 3.

All of the pattern light illuminating section 2, the imaging section 3, and the control unit 4 can be integrated.

The embodiments explained above are only illustrations in all aspects and should not be limitedly interpreted. Further, all of modifications and changes belonging to a scope of equivalents of the claims are within the scope of the present invention.

INDUSTRIAL APPLICABILITY

As explained above, the image inspection apparatus according to the present invention can be used when a defect of an inspection target object is inspected using images obtained by imaging various inspection target objects.

What is claimed is:

1. An image inspection apparatus that inspects a defect of an inspection target object using an image obtained by imaging the inspection target object moving in one direction, the image inspection apparatus comprising:
a pattern light illuminating section for irradiating pattern light having a periodic illuminance distribution on the inspection target object;
an imaging section configured to be capable of being set independently from the pattern light illuminating section and including a line camera that includes a plurality of image receiving elements arrayed in a line shape and is capable of being set such that an array direction of the light receiving elements is a direction orthogonal to the moving direction of the inspection target object;
a control section configured to control the pattern light illuminating section and the imaging section to generate a plurality of pattern lights, phases of illuminance distributions of which are shifted in the array direction of the light receiving elements, and a plurality of pattern lights shifted in the moving direction of the inspection target object, sequentially irradiate the pattern lights on the inspection target object, image the inspection target object at timings when the pattern lights are irradiated, and obtain a plurality of luminance images;
an image generating section configured to generate, on the basis of a deflectometry principle, phase data of a surface of the inspection target object from the plurality of luminance images captured by the imaging section and generate, on the basis of the phase data, an image for inspection indicating a shape of the inspection target object; and
an information acquiring section configured to acquire moving direction information concerning the moving direction of the inspection target object with respect to the array direction of the light receiving elements of the line camera and positional relation information concerning a positional relation between the light receiving elements of the line camera and the pattern light illuminating section, wherein
the control section is configured to determine, according to the moving direction information and the positional relation information acquired by the information acquiring section, a phase shift direction of the pattern lights irradiated by the pattern light illuminating section so that a proper direction is acquired to obtain the phase data based on the deflectometry principle.

2. The image inspection apparatus according to claim 1, wherein the positional relation information includes a positional relation of reflected light reception in which the light receiving elements receive the pattern lights irradiated from the pattern light illuminating section and reflected on the inspection target object and a positional relation of transmitted light reception in which the light receiving elements receive the pattern lights irradiated from the pattern light illuminating section and transmitted through the inspection target object.

3. The image inspection apparatus according to claim 1, wherein, when a direction orthogonal to the array direction of the light receiving elements when viewed from a light reception side of the line camera is set as an up-down direction of the line camera, the moving direction information includes the up-down direction of the line camera and the moving direction of the inspection target object.

4. The image inspection apparatus according to claim 1, wherein
the information acquiring section is configured to control, during setting of the image inspection apparatus performed before the image inspection apparatus is operated, the pattern light illuminating section and the imaging section to generate a first image obtained by imaging an irradiation surface on which first pattern light having a periodic illuminance distribution in one direction is irradiated and a second image obtained by imaging an irradiation surface on which second pattern light having a periodic illuminance distribution in a direction orthogonal to the one direction is irradiated, and
the information acquiring section is configured to analyze the first image and the second image to thereby acquire positional relation information concerning a positional relation between the light receiving elements of the line camera and the pattern light illuminating section.

5. The image inspection apparatus according to claim 1, wherein the control section is configured to control the pattern light illuminating section and the imaging section to generate a plurality of pattern lights, phases of illuminance distributions of which are shifted in both directions of the array direction of the light receiving elements and the moving direction of the inspection target object, and sequentially irradiate the pattern lights on the inspection target object and, every time the pattern light is irradiated, image the inspection target object to generate a plurality of luminance images.

6. An image inspection apparatus that inspects a defect of an inspection target object using an image obtained by imaging the inspection target object moving in one direction, the image inspection apparatus comprising:
a pattern light illuminating section for irradiating pattern light having a periodic illuminance distribution on the inspection target object;
an imaging section configured to be capable of being set independently from the pattern light illuminating section and including a line camera that includes a plurality of image receiving elements arrayed in a line shape and is capable of being set such that an array direction of the light receiving elements is a direction orthogonal to the moving direction of the inspection target object;
a control section configured to control the pattern light illuminating section and the imaging section to generate a plurality of pattern lights, phases of illuminance distributions of which are shifted in the array direction of the light receiving elements and the moving direction of the inspection target object, sequentially irradiate the pattern lights on the inspection target object, image the inspection target object at timings when the pattern lights are irradiated, and obtain a plurality of luminance images;
an image generating section configured to generate, on the basis of a deflectometry principle, phase data of a surface of the inspection target object from the plurality of luminance images captured by the imaging section and generate, on the basis of the phase data, an image for inspection indicating a shape of the inspection target object; and
an information acquiring section configured to acquire moving direction information concerning the moving direction of the inspection target object with respect to the array direction of the light receiving elements of the line camera and positional relation information concerning a positional relation between the light receiving elements of the line camera and the pattern light illuminating section, wherein the image generating section is configured to generate, according to the moving direction information and the positional relation information acquired by the information acquiring section, the image for inspection related to the shape of the inspection target object.

* * * * *